(12) United States Patent
Cohen et al.

(10) Patent No.: US 10,234,459 B2
(45) Date of Patent: Mar. 19, 2019

(54) SENSORS AND ASSAYS FOR UBIQUITIN OR UBIQUITIN-LIKE PROTEINS

(71) Applicant: Colorado State University Research Foundation, Fort Collins, CO (US)

(72) Inventors: Robert E. Cohen, Fort Collins, CO (US); Yun-Seok Choi, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 0 days.

(21) Appl. No.: 15/977,727

(22) Filed: May 11, 2018

(65) Prior Publication Data

US 2018/0364250 A1    Dec. 20, 2018

Related U.S. Application Data

(62) Division of application No. 14/266,502, filed on Apr. 30, 2014, now Pat. No. 10,018,634.

(60) Provisional application No. 61/817,517, filed on Apr. 30, 2013.

(51) Int. Cl.
| | |
|---|---|
| *C12N 9/48* | (2006.01) |
| *C07K 14/47* | (2006.01) |
| *G01N 33/68* | (2006.01) |
| *C07K 14/435* | (2006.01) |

(52) U.S. Cl.
CPC ....... *G01N 33/6842* (2013.01); *C07K 14/435* (2013.01); *C07K 14/47* (2013.01); *C12N 9/485* (2013.01); *C12Y 304/19012* (2013.01); *G01N 33/6872* (2013.01); *C07K 2319/00* (2013.01); *C07K 2319/70* (2013.01)

(58) Field of Classification Search
None
See application file for complete search history.

(56) References Cited

U.S. PATENT DOCUMENTS

| 10,018,634 B2 | 7/2018 | Cohen et al. |
| 2010/0151484 A1 | 6/2010 | Vogel et al. |
| 2011/0250613 A1 | 10/2011 | Sims et al. |
| 2012/0009211 A1 | 1/2012 | Tschopp et al. |
| 2014/0322725 A1 | 10/2014 | Cohen et al. |

FOREIGN PATENT DOCUMENTS

| EP | 2096174 A1 | 9/2009 |
| WO | WO 2014/179494 A1 | 11/2014 |

OTHER PUBLICATIONS

Dikic, et al., "Ubiquitin-Binding Domains—from Structures to Functions," Nature Reviews, Molecular Cell Biology (2009); 10: 659-671.
Garner, et al., "Independent Interactions of Ubiquitin-Binding Domains in a Ubiquitin-Mediated Ternary Complex," Biochemistry Including Biophysical Chemistry & Molecular Biology, American Chemical Society Publications (2011); 50: 9076-9087.
International Application No. PCT/US2014/036243, International Search Report and Written Opinion dated Sep. 24, 2014.
International Application No. PCT/US2014/036243, International Preliminary Report on Patentability dated Nov. 3, 2015.
Pai et al., "Solution Structure of the Ubp-M BUZ Domain, a Highly Specific Protein Module that Recognizes the C-terminal Tail of Free Ubiquitin," Journal of Molecular Biology (2007) 370, 290-302.
Penengo et al., "Crystal Structure of the Ubiquitin Binding Domains of Rabex-5 Reveals Two Modes of Interaction with Ubiquitin," Cell, 124, 1183-1195, Mar. 24, 2006.
Raiborg, et al., "A New Side to Ubiquitin," Trends in Biochemical Sciences, Science Direct (2006); 31(10): 541-544.
van der Veen et al., "Ubiquitin-Like Proteins," Annual Review of Biochemistry, 2012. 81:323-57.
Yao and Cohen, "A cryptic protease couples deubiquitination and degradation by the proteasome", Nature (2002); 419(6905): 403-407.

*Primary Examiner* — Paul J Holland

(57) ABSTRACT

The present invention provides compositions comprising chimeric polypeptides that bind to free ubiquitin proteins or free ubiquitin-like proteins with high affinity, as well as chimeric polypeptides that bind to both free and conjugated ubiquitin proteins or free and conjugated ubiquitin-like proteins, and methods of using the chimeric polypeptides to determine the amount of free or total ubiquitin or free or total ubiquitin-like proteins in various types of samples.

Figure 4:
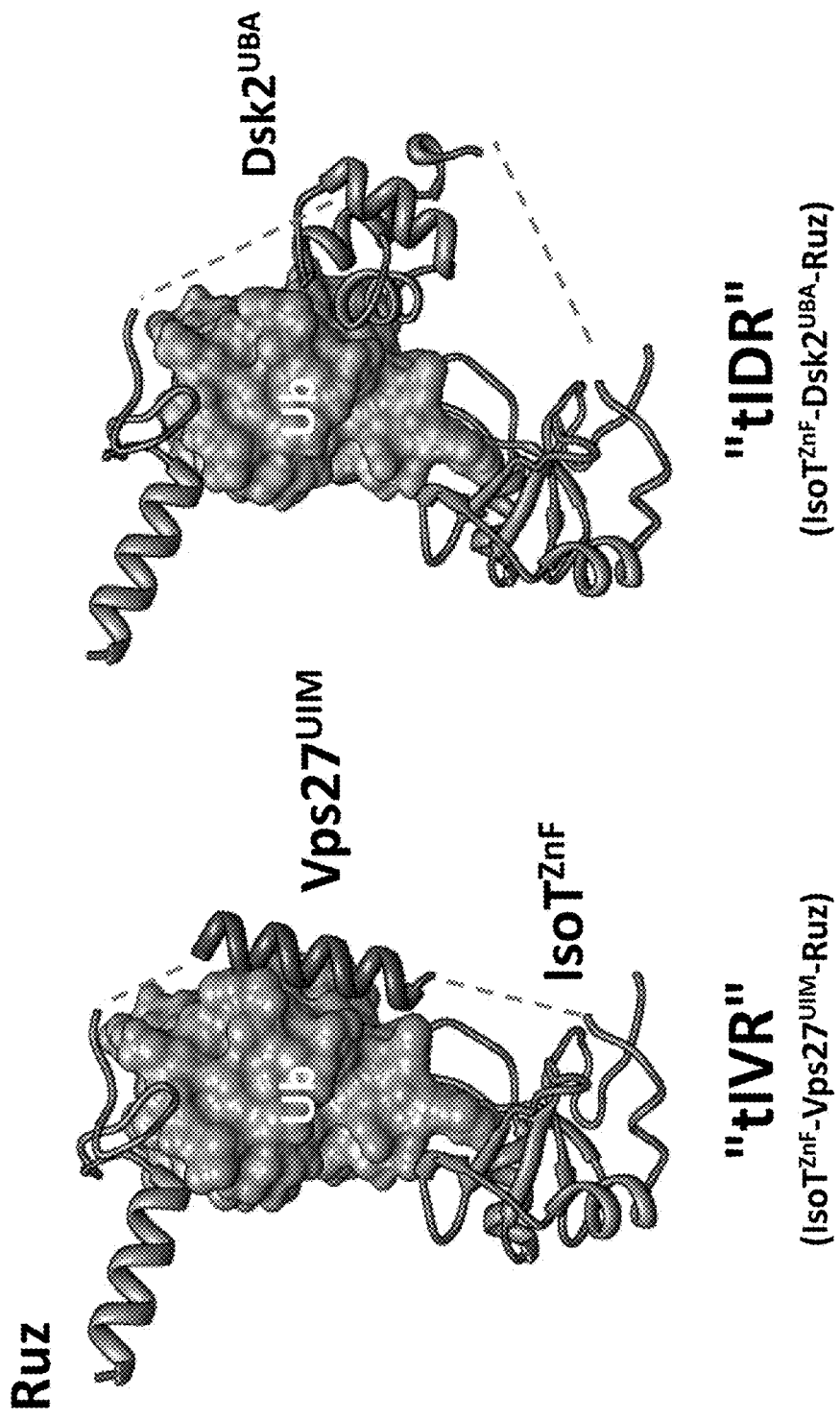

19 Claims, 26 Drawing Sheets
Specification includes a Sequence Listing.

Design concept of sensors for free Ub: link three non-overlapping UBDs

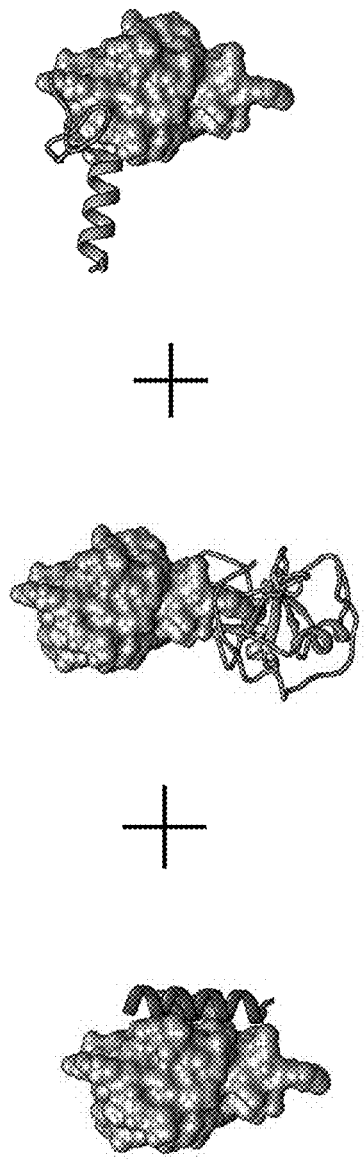

A UIM-type UBD that binds to Ub hydrophobic patch

A ZnF Ubp-type UBD that binds to Ub free C-terminus

A Ruz-domain UBD that binds to the surface around Ub Asp58

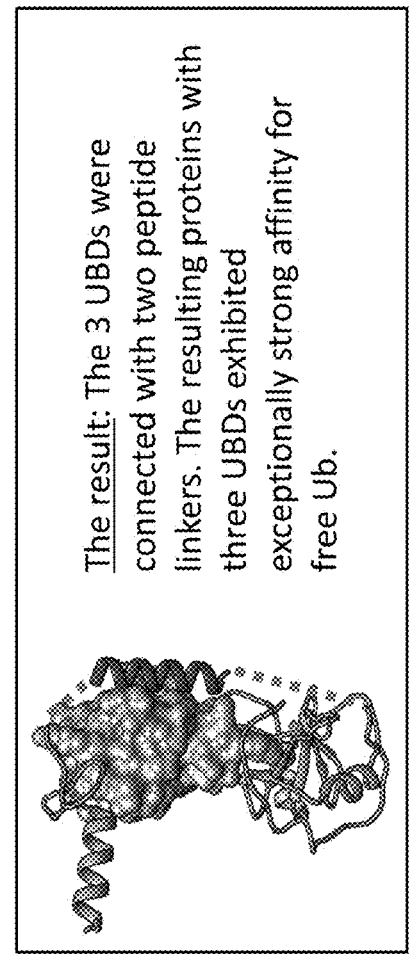

The result: The 3 UBDs were connected with two peptide linkers. The resulting proteins with three UBDs exhibited exceptionally strong affinity for free Ub.

*FIG. 1*

Construction scheme for the sensors

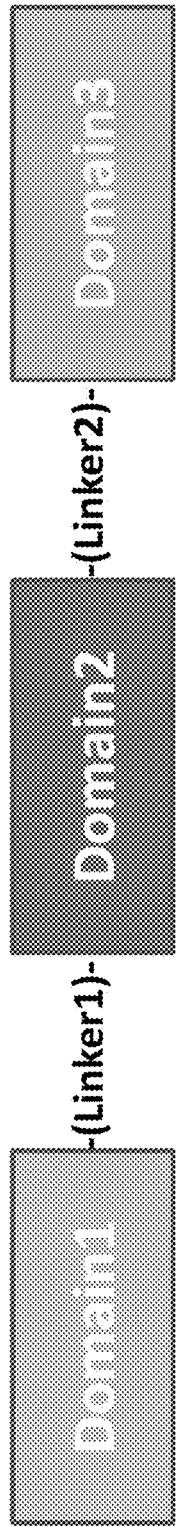

Domain1 -(Linker1)- Domain2 -(Linker2)- Domain3

- Domain 1: Any domain that binds to Ub C-terminus can be used.
  e.g., IsoT$^{ZnF, 163-291}$ (Reyes-Turcu et al. (2006) Cell, vol. 124) and PAZ or Buz domain (Boyault et al. (2006) EMBO Journal, vol. 25; Pai et al. (2007) J. Mol. Biol., vol. 370).

- Domain 2: Any domain that binds to Ub hydrophobic patch and does not clash sterically with the other domains can be used.
  e.g., UIM, DUIM, MIU, UBA, CUE, UBZ, NZF, VHS, PFUC, SH3, UEV, UBM, GAT (see Garner et al. (2011) Biochemistry, vol. 5; Dikic et al. (2009) Nat. Rev. Mol. Cell Biol., vol. 10)

- Domain 3: Any domain that binds to the surface around Ub Asp58 can be used.
  e.g., Rabex$^{Ruz}$ and ZnF216$^{14-44}$ (Garner et al. (2011) Biochemistry, vol. 50)

*FIG. 2*

Two sensor prototypes: tIVR and tIDR

- tIVR: [IsoT^ZnF]-(Linker1)-[Vps27^UIM]-(Linker2)-[Ruz]
- tIDR: [IsoT^ZnF]-(Linker1)-[Dsk2^UBA]-(Linker2)-[Ruz]

Sequences of the different UBDs employed in the above constructs:

tIVR
MGSSHHHHHHSSGLVPRGSHHMKQEVQAWDGEVRQVSKHAFSLKQLDNPARIPPSGWKCSKCDMRENLWLNLTDGSILCGRRYF
DGSGGNNHAVEHYRETGYPLAVKLGTITPDGADVYSYDEDDMVLDPSLAEHLSHFGIDMLKMQKGSAAAEEAELDLKAAIQE
SLREAGGGGSDLLCKKGCGYYGNPAWQGFCSKCWREEYHKARQK (SEQ ID NO:1) (Underline shows each linker.)

tIDR
MGSSHHHHHHSSGLVPRGSHHMKQEVQAWDGEVRQVSKHAFSLKQLDNPARIPPSGWKCSKCDMRENLWLNLTDGSILCGRRY
FDGSGGNNHAVEHYRETGYPLAVKLGTITPDGADVYSYDEDDMVLDPSLAEHLSHFGIDMLKMQKTGGSGGSGGSGPPE
ERYEHQLRQLNDMGFFDFDRNVAALRRSGGSVQGALDSLLNGGGGGSSGGGGSDLLCKKGCGYYGNPAWQGFCSKCWREEY
HKARQK (SEQ ID NO:4) (Underline shows each linker.)

*FIG. 3*

The affinities of the sensors were determined with Ub(S20C) labeled with different fluorophores on residue Cys20

| Sensor | Kd (nM) | | |
|---|---|---|---|
| | Fluorescein-Ub | Atto532-Ub | Alexa488-Ub |
| tIVR | 0.69 ± 0.32 | 0.41 ± 0.07 | 1.05 ± 0.15 |
| tIDR | 1.05 ± 0.56 | n.d. | n.d. |

*n.d.*, not determined

Binding curves for these assay are in the next page.

Ub(S20C) sequence
MQIFVKTLTGKTITLEVEPCDTIENVKAKIQDKEGIPPDQQRLIFAGKQLEDGRTLSDYNIQKESTLHLVLRLRGG
(SEQ ID NO:27) (Residue C20 (bolded) is the fluorophore attachment site.)

*FIG. 5*

The affinities of the sensors were determined with Ub(S20C) labeled with different fluorophores on residue Cys20

Affinity between Fluorescein-Ub(S20C) and tIVR was measured by fluorescence anisotropy

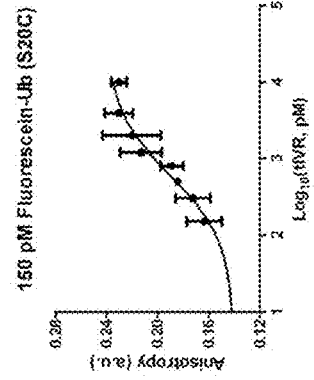

Affinity between Fluorescein-Ub(S20C) and tIDR was measured as the ratio of the association and dissociation rates

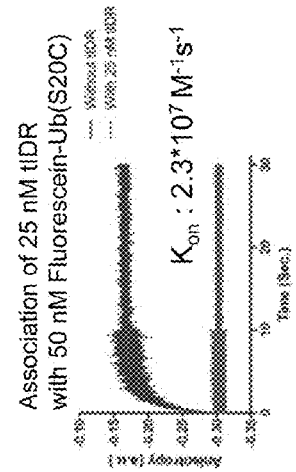

Affinity between Alexa488-Ub(S20C) or Atto532-Ub(S20C) and tIVR was measured by fluorescence intensity change

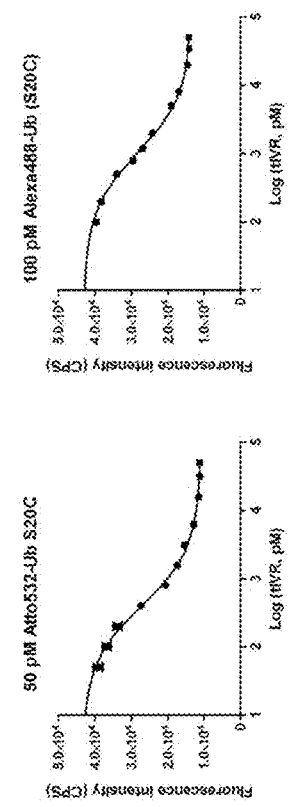

FIG. 6 tIVR has similar binding affinities to free polyUb of different Ub–Ub linkage types

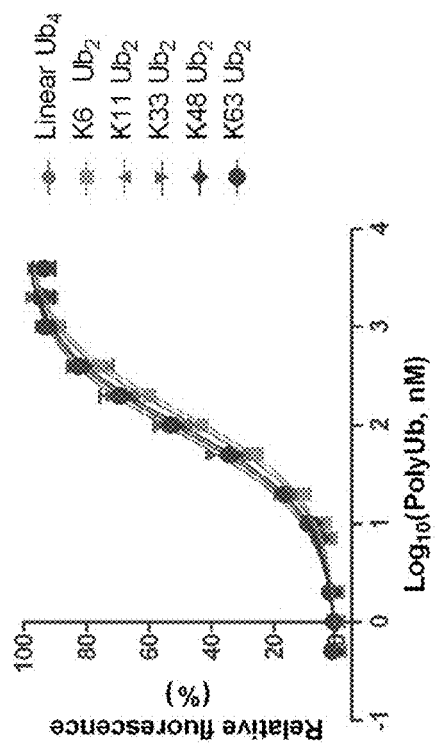

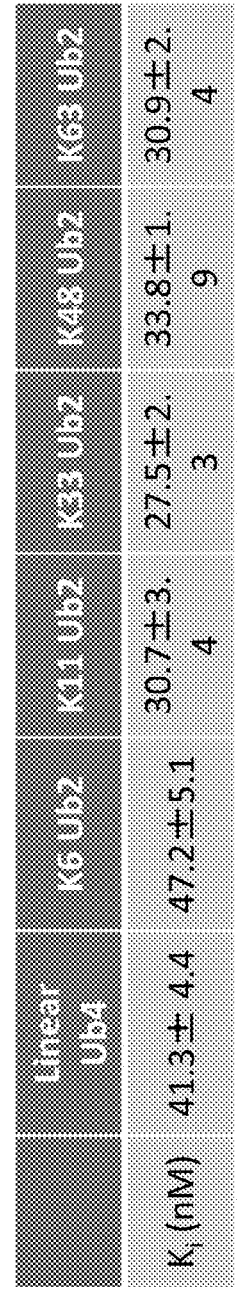

| | Linear Ub4 | K6 Ub2 | K11 Ub2 | K33 Ub2 | K48 Ub2 | K63 Ub2 |
|---|---|---|---|---|---|---|
| $K_i$ (nM) | 41.3±4.4 | 47.2±5.1 | 30.7±3.4 | 27.5±2.3 | 33.8±1.9 | 30.9±2.4 |

Competition assay with 0.8 nM Atto532-Ub S20C, 6 nM tIVR, and the polyUb. Relative fluorescence intensities of Atto532-Ub with tIVR were plotted upon titration with the competitor (upper panel). The table shows $K_i$ values calculated from fitting data in the upper panel to a model of single-site competition.

*FIG. 9*

The length of Linker1 also can contribute the sensor specificity.

- A shortened Linker 1 decreased the sensor affinity for conjugated *vs* free Ub by limiting access of the UIM domain to the Ub surface.

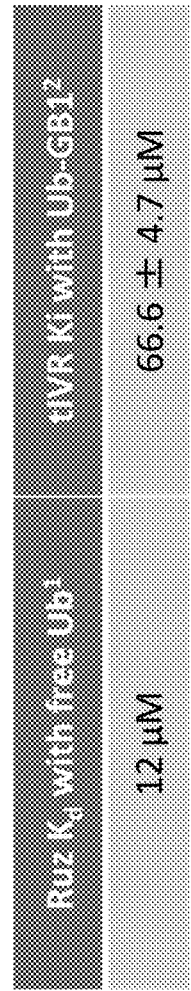

| Ruz Kd with free Ub1 | tlVR Kd with Ub-GB1* |
|---|---|
| 12 µM | 66.6 ± 4.7 µM |

Figure 8:
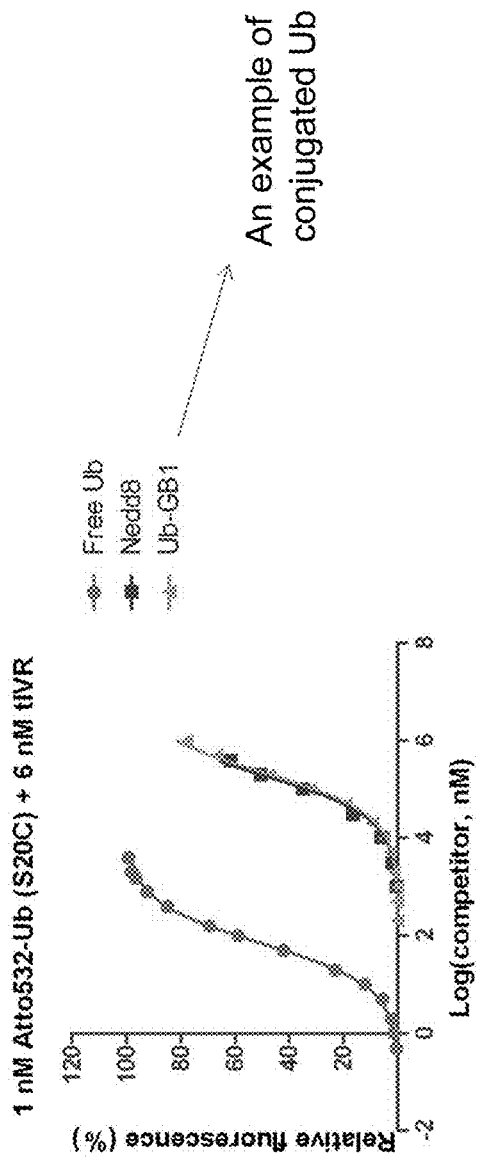

1. Penengo et al., *Cell* vol. 124 (2006)
2. These data are shown in Figure 8

\* tlVR with shortened Linker 1 was used for all experiments shown here except for our use of the tlVR(R218C) construct.

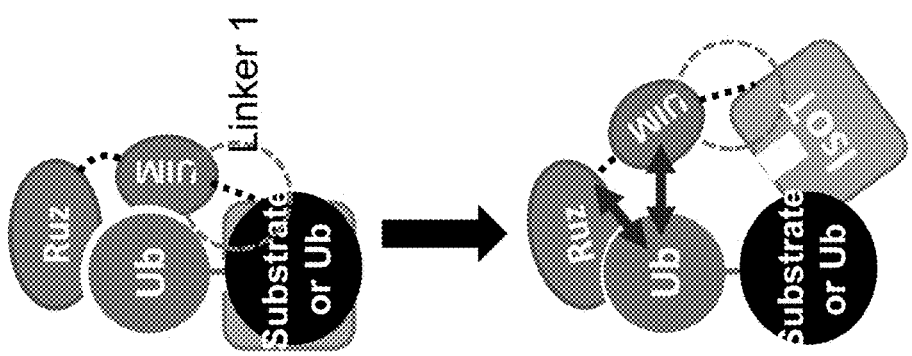

*FIG. 10*

Optimized Linker 1 in tIVR is short and made more rigid by having a high fraction of Ala residues

| tIVR Linker 1 | Affinity with AlexaS32-Ub (Kd, nM) | Affinity with Ub-GB1 (Kd, nM) | Specificity (Ub/Ub-GB1) |
|---|---|---|---|
| AAA (SEQ ID NO: 30) | 3.0 | n.d. | n.d. |
| GSAAA (SEQ ID NO: 13) | 0.4 ± 0.1 | 66600 ± 4700 | 166500 |
| TGGSGGSAAA (SEQ ID NO: 28) | 0.6 | 14900 ± 1200 | 24833 | n.d., not determined

A minimal length for linker 1 helps the free-Ub sensors to achieve better selectivity. tIVR with Linker 1 containing 12 amino acids shows 6.7-fold lower selectivity for free Ub than tIVR with GSAAA as Linker 1. The high fraction of Ala residues in the linker is included to promote rigidity of the linker. Binding curves for these data are in the next slide.

*FIG. 11*

F-Ub(S20C) (left panel) or F-sensors (right panel) show large fluorescence intensity changes upon binding the sensor or free Ub, respectively. Relative fluorescence intensities are shown with fluorescence of the unbound fluorescent-protein scaled to 100%. "L1 Cys" means that the linker between IsoT$^{ZnF}$ and UIM (i.e., Linker 1) has Cys conjugated with the fluorophore.

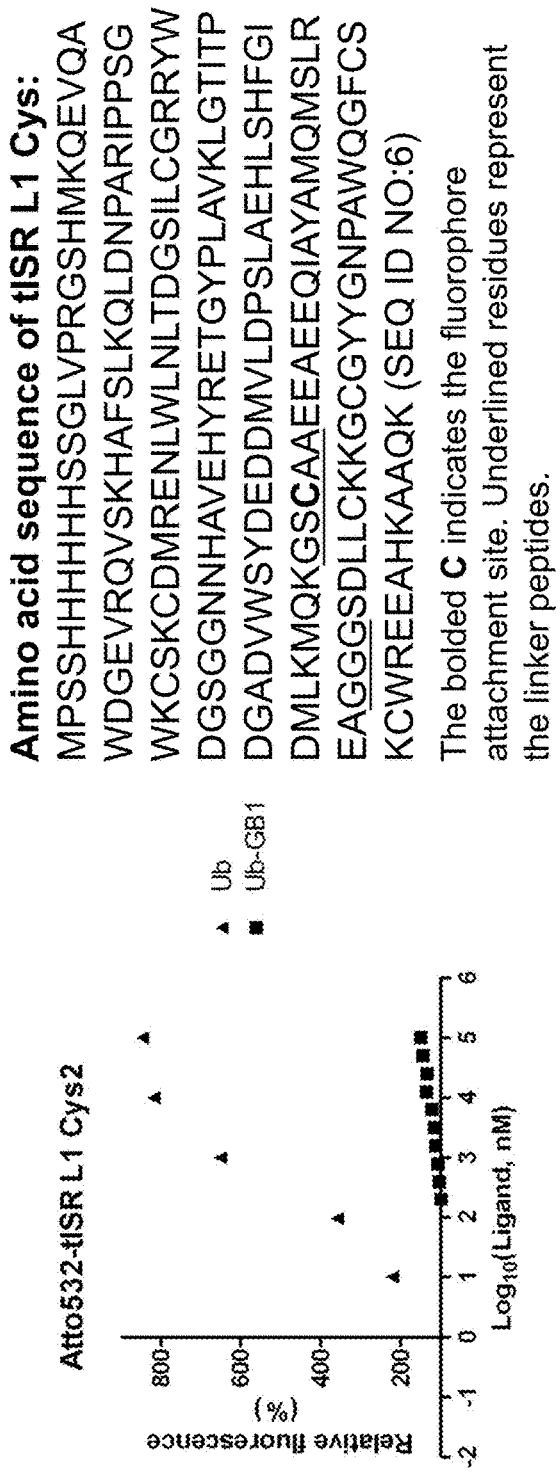

FIG. 15

Atto532-tISR (IsoT^ZnF-S5a^UIM-Rabex^Ruz) L1 Cys2 shows a large fluorescence intensity change (about 800%) upon Ub binding

Amino acid sequence of tISR L1 Cys:
MPSSHHHHHHSSGLVPRGSHMKQEVQA
WDGEVRQVSKHAFSLKQLDNPARIPPSG
WKCSKCDMRENLWLNLTDGSILCGRRYW
DGSGGNNHAVEHYRETGYPLAVKLGTITP
DGADVWSYDEDDMVLDPSLAEHLSHFGI
DMLKMQKGSC**AAEEEAEEQIAYAMQMSLR
EAGGGSDLLCKKGCGYYGNPAWQGFCS
KCWREEAHKAAQK (SEQ ID NO:6)

The bolded C indicates the fluorophore attachment site. Underlined residues represent the linker peptides.

L1 Cys2 means the linker between IsoT^ZnF and the UIM has Cys conjugated with the fluorophore. Relative fluorescence intensity are shown here and fluorescence of fluorescent-protein without a ligand is 100%. Atto532-tISR L1 Cys2 shows little fluorescence increase upon 10 μM conjugated Ub. Strong points of this particular sensor are 1) very large fluorescence change, and 2) relatively broad dynamic range (0-1000 nM Ub).

DUB activity can be monitored continuously

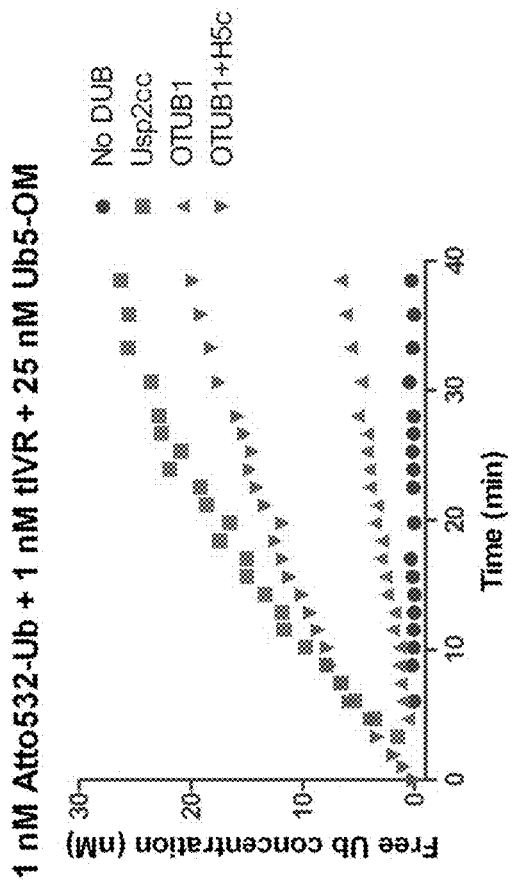

FIG. 21

Real-time DUB assay using Atto532-Ub(S20C) and tIVR. K48-linked $Ub_5$-ovomucoid, a mimic of a polyubiquitinated-protein substrate, was digested with 25 nM Usp2cc or 3 μM OTUB1 with or without 5 μM UbcH5c in presence of 1 nM Atto532-Ub(S20C) and 1 nM tIVR to detect free Ub released by the DUBs. OTUB1 DUB activity is upregulated by UBCH5C (Weiner et al. (2013) Nat Struct Mol Biol., vol. 20).

Atto532-tIV L1 Cys binds to free Nedd8 with a Kd of several μM $K_d$: 9.4 ± 0.3 μM Fluorescence intensity of Atto532-tIV L1 Cys upon Nedd8 binding increases 6-fold. Because of steric clash between the IsoT$^{ZnF}$ domain in tIV L1 Cys and conjugated Nedd8 and the very weak binding of UIM to Nedd8 (Singh et al., 11, 2012, Mol. Cell. Proteomics), conjugated Nedd8 will bind much more weakly (~100-fold) to Atto532-tIV L1 Cys.

Construction scheme for the universal sensors

-(Linker1)-

- Domain 2 : Any domain that binds to Ub hydrophobic patch and doesn't clash sterically with the other domains can be used.
- Domain 3 : Any domain that binds to the surface around Ub Asp58 can be used.
- Linker 1: connects Domains 2 and 3.

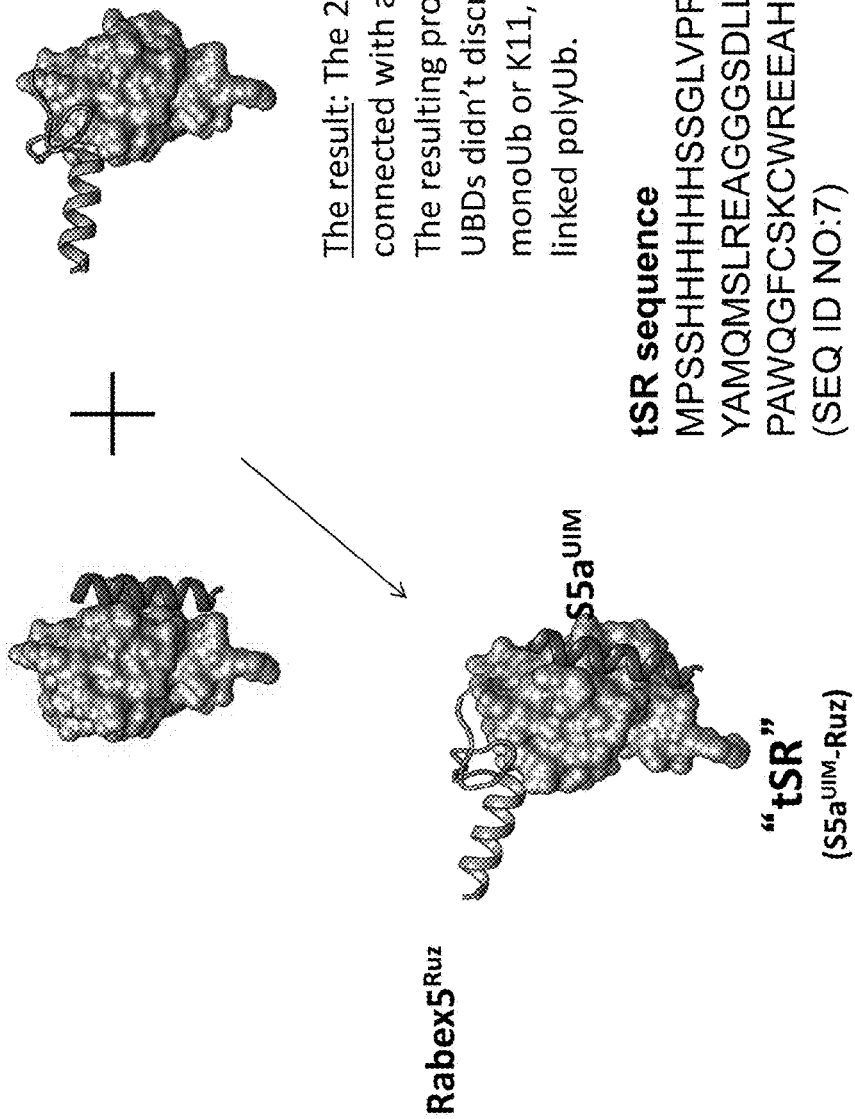

FIG. 24

Design concept of universal sensor: link two non-overlapping UBDs

The result: The 2 UBDs were connected with a peptide linker. The resulting protein with two UBDs didn't discriminate among monoUb or K11, K48, or K63-linked polyUb.

tSR sequence
MPSSHHHHHHSSGLVPRGSHMTEEEQIA
YAMQMSLREAGGGSDLLCKKGCGYYGN
PAWQGFCSKCWREEAHKCAAERAAAE
(SEQ ID NO:7)

Rabex5^Ruz

S5a^UIM

"tSR"
(S5a^UIM-Ruz)

Competition assay with 5 nM Atto532-Ub(S20C), 600 nM tSR, and the competitors. Relative fluorescence intensities of Atto532-Ub (S20C) with tSR were plotted upon the competitor titration. The table shows $K_i$ values calculated from the curve-fitting of the data in upper panel.

Left panel is model structure of Alexa488-labeled tSR with bound Ub. Middle panel shows relative fluorescence intensity change of Alexa488-tSR upon Ub binding. Direct titration of 10 nM Alexa488-tSR with Ub, Ub-GB1, or Nedd8 was performed, and the binding curves were generated by measuring the fluorescence intensities.

SEQUENCE LISTING

<160> NUMBER OF SEQ ID NOS: 42

<210> SEQ ID NO 1
<211> LENGTH: 208

<212> TYPE: PRT
<213> ORGANISM: Artificial Sequence
<220> FEATURE:
<223> OTHER INFORMATION: tIVR - chimeric polypeptide comprising three
      binding domains that bind ubiquitin in non-overlapping regions

<400> SEQUENCE: 1

Met Gly Ser Ser His His His His His Ser Ser Gly Leu Val Pro
1               5                   10                  15

Arg Gly Ser His Met Lys Gln Glu Val Gln Ala Trp Asp Gly Glu Val
            20                  25                  30

Arg Gln Val Ser Lys His Ala Phe Ser Leu Lys Gln Leu Asp Asn Pro
        35                  40                  45

Ala Arg Ile Pro Pro Ser Gly Trp Lys Cys Ser Lys Cys Asp Met Arg
    50                  55                  60

Glu Asn Leu Trp Leu Asn Leu Thr Asp Gly Ser Ile Leu Cys Gly Arg
65                  70                  75                  80

Arg Tyr Phe Asp Gly Ser Gly Gly Asn Asn His Ala Val Glu His Tyr
                85                  90                  95

Arg Glu Thr Gly Tyr Pro Leu Ala Val Lys Leu Gly Thr Ile Thr Pro
            100                 105                 110

Asp Gly Ala Asp Val Tyr Ser Tyr Asp Glu Asp Met Val Leu Asp
        115                 120                 125

Pro Ser Leu Ala Glu His Leu Ser His Phe Gly Ile Asp Met Leu Lys
    130                 135                 140

Met Gln Lys Gly Ser Ala Ala Ala Glu Glu Ala Glu Leu Asp Leu Lys
145                 150                 155                 160

Ala Ala Ile Gln Glu Ser Leu Arg Glu Ala Gly Gly Ser Asp Leu
                165                 170                 175

Leu Cys Lys Lys Gly Cys Gly Tyr Tyr Gly Asn Pro Ala Trp Gln Gly
            180                 185                 190

Phe Cys Ser Lys Cys Trp Arg Glu Glu Tyr His Lys Ala Arg Gln Lys
        195                 200                 205

<210> SEQ ID NO 2
<211> LENGTH: 209
<212> TYPE: PRT
<213> ORGANISM: Artificial Sequence
<220> FEATURE:
<223> OTHER INFORMATION: tIVR tagged with a fluorophore - chimeric
      polypeptide comprising three binding domains that bind ubiquitin
      in non-overlapping regions

<400> SEQUENCE: 2

Met Gly Ser Ser His His His His His Ser Ser Gly Leu Val Pro
1               5                   10                  15

Arg Gly Ser His Met Lys Gln Glu Val Gln Ala Trp Asp Gly Glu Val
            20                  25                  30

Arg Gln Val Ser Lys His Ala Phe Ser Leu Lys Gln Leu Asp Asn Pro
        35                  40                  45

Ala Arg Ile Pro Pro Ser Gly Trp Lys Cys Ser Lys Cys Asp Met Arg
    50                  55                  60

Glu Asn Leu Trp Leu Asn Leu Thr Asp Gly Ser Ile Leu Cys Gly Arg
65                  70                  75                  80

Arg Tyr Phe Asp Gly Ser Gly Gly Asn Asn His Ala Val Glu His Tyr
                85                  90                  95

Arg Glu Thr Gly Tyr Pro Leu Ala Val Lys Leu Gly Thr Ile Thr Pro
            100                 105                 110

Asp Gly Ala Asp Val Tyr Ser Tyr Asp Glu Asp Met Val Leu Asp
            115                 120                 125

Pro Ser Leu Ala Glu His Leu Ser His Phe Gly Ile Asp Met Leu Lys
        130                 135                 140

Met Gln Lys Gly Ser Cys Ala Ala Glu Glu Ala Glu Leu Asp Leu
145                 150                 155                 160

Lys Ala Ala Ile Gln Glu Ser Leu Arg Glu Gly Gly Ser Asp
                165                 170                 175

Leu Leu Cys Lys Lys Gly Cys Gly Tyr Tyr Gly Asn Pro Ala Trp Gln
                180                 185                 190

Gly Phe Cys Ser Lys Cys Trp Arg Glu Glu Tyr His Lys Ala Arg Gln
            195                 200                 205

Lys

<210> SEQ ID NO 3
<211> LENGTH: 220
<212> TYPE: PRT
<213> ORGANISM: Artificial Sequence
<220> FEATURE:
<223> OTHER INFORMATION: tIVR tagged with a fluorophore - chimeric
      polypeptide comprising three binding domains that bind ubiquitin
      in non-overlapping regions

<400> SEQUENCE: 3

Met Gly Ser Ser His His His His His His Ser Ser Gly Leu Val Pro
1               5                   10                  15

Arg Gly Ser His Met Lys Gln Glu Val Gln Ala Trp Asp Gly Glu Val
            20                  25                  30

Arg Gln Val Ser Lys His Ala Phe Ser Leu Lys Gln Leu Asp Asn Pro
        35                  40                  45

Ala Arg Ile Pro Pro Ser Gly Trp Lys Cys Ser Lys Cys Asp Met Arg
    50                  55                  60

Glu Asn Leu Trp Leu Asn Leu Thr Asp Gly Ser Ile Leu Cys Gly Arg
65                  70                  75                  80

Arg Tyr Phe Asp Gly Ser Gly Gly Asn Asn His Ala Val Glu His Tyr
                85                  90                  95

Arg Glu Thr Gly Tyr Pro Leu Ala Val Lys Leu Gly Thr Ile Thr Pro
            100                 105                 110

Asp Gly Ala Asp Val Tyr Ser Tyr Asp Glu Asp Met Val Leu Asp
            115                 120                 125

Pro Ser Leu Ala Glu His Leu Ser His Phe Gly Ile Asp Met Leu Lys
        130                 135                 140

Met Gln Lys Thr Gly Ser Gly Gly Ser Gly Ser Ala Ala Ala Glu
145                 150                 155                 160

Glu Ala Glu Leu Asp Leu Lys Ala Ala Ile Gln Glu Ser Leu Arg Glu
                165                 170                 175

Ala Gly Gly Gly Ser Ser Gly Gly Ser Asp Leu Leu Cys Lys Lys
                180                 185                 190

Gly Cys Gly Tyr Tyr Gly Asn Pro Ala Trp Gln Gly Phe Cys Ser Lys
            195                 200                 205

Cys Trp Arg Glu Glu Tyr His Lys Ala Cys Gln Lys
            210                 215                 220

<210> SEQ ID NO 4
<211> LENGTH: 250
<212> TYPE: PRT

<213> ORGANISM: Artificial Sequence
<220> FEATURE:
<223> OTHER INFORMATION: tIDR - Chimeric polypeptide comprising three
      binding domains that bind ubiquitin in non-overlapping regions

<400> SEQUENCE: 4

Met Gly Ser Ser His His His His His His Ser Ser Gly Leu Val Pro
1               5                   10                  15

Arg Gly Ser His His Met Lys Gln Glu Val Gln Ala Trp Asp Gly Glu
            20                  25                  30

Val Arg Gln Val Ser Lys His Ala Phe Ser Leu Lys Gln Leu Asp Asn
                35                  40                  45

Pro Ala Arg Ile Pro Pro Ser Gly Trp Lys Cys Ser Lys Cys Asp Met
    50                  55                  60

Arg Glu Asn Leu Trp Leu Asn Leu Thr Asp Gly Ser Ile Leu Cys Gly
65                  70                  75                  80

Arg Arg Tyr Phe Asp Gly Ser Gly Gly Asn Asn His Ala Val Glu His
                85                  90                  95

Tyr Arg Glu Thr Gly Tyr Pro Leu Ala Val Lys Leu Gly Thr Ile Thr
            100                 105                 110

Pro Asp Gly Ala Asp Val Tyr Ser Tyr Asp Glu Asp Asp Met Val Leu
        115                 120                 125

Asp Pro Ser Leu Ala Glu His Leu Ser His Phe Gly Ile Asp Met Leu
130                 135                 140

Lys Met Gln Lys Thr Gly Gly Ser Gly Gly Ser Gly Ser Gly Gly Ser
145                 150                 155                 160

Gly Pro Pro Glu Glu Arg Tyr Glu His Gln Leu Arg Gln Leu Asn Asp
                165                 170                 175

Met Gly Phe Phe Asp Phe Asp Arg Asn Val Ala Ala Leu Arg Arg Ser
            180                 185                 190

Gly Gly Ser Val Gln Gly Ala Leu Asp Ser Leu Leu Asn Gly Gly Gly
        195                 200                 205

Gly Gly Ser Ser Gly Gly Gly Ser Asp Leu Leu Cys Lys Lys Gly Cys
    210                 215                 220

Gly Tyr Tyr Gly Asn Pro Ala Trp Gln Gly Phe Cys Ser Lys Cys Trp
225                 230                 235                 240

Arg Glu Glu Tyr His Lys Ala Arg Gln Lys
                245                 250

<210> SEQ ID NO 5
<211> LENGTH: 171
<212> TYPE: PRT
<213> ORGANISM: Artificial Sequence
<220> FEATURE:
<223> OTHER INFORMATION: tIV - Atto532-tagged chimeric polypeptide
      comprising two binding domains that bind ubiquitin in non-
      overlapping regions

<400> SEQUENCE: 5

Met Gly Ser Ser His His His His His His Ser Ser Gly Leu Val Pro
1               5                   10                  15

Arg Gly Ser His Met Lys Gln Glu Val Gln Ala Trp Asp Gly Glu Val
            20                  25                  30

Arg Gln Val Ser Lys His Ala Phe Ser Leu Lys Gln Leu Asp Asn Pro
        35                  40                  45

Ala Arg Ile Pro Pro Ser Gly Trp Lys Cys Ser Lys Cys Asp Met Arg
    50                  55                  60

Glu Asn Leu Trp Leu Asn Leu Thr Asp Gly Ser Ile Leu Cys Gly Arg
65                  70                  75                  80

Arg Tyr Phe Asp Gly Ser Gly Gly Asn Asn His Ala Val Glu His Tyr
                85                  90                  95

Arg Glu Thr Gly Tyr Pro Leu Ala Val Lys Leu Gly Thr Ile Thr Pro
            100                 105                 110

Asp Gly Ala Asp Val Trp Ser Tyr Asp Glu Asp Met Val Leu Asp
            115                 120                 125

Pro Ser Leu Ala Glu His Leu Ser His Phe Gly Ile Asp Met Leu Lys
        130                 135                 140

Met Gln Lys Gly Ser Cys Ala Ala Glu Glu Ala Glu Leu Asp Leu
145                 150                 155                 160

Lys Ala Ala Ile Gln Glu Ser Leu Arg Glu Ala
                165                 170

<210> SEQ ID NO 6
<211> LENGTH: 208
<212> TYPE: PRT
<213> ORGANISM: Artificial Sequence
<220> FEATURE:
<223> OTHER INFORMATION: tISR - Chimeric polypeptide comprising three
      binding domains that bind ubiquitin in non-overlapping regions

<400> SEQUENCE: 6

Met Pro Ser Ser His His His His His Ser Gly Leu Val Pro
1               5                   10                  15

Arg Gly Ser His Met Lys Gln Glu Val Gln Ala Trp Asp Gly Glu Val
                20                  25                  30

Arg Gln Val Ser Lys His Ala Phe Ser Leu Lys Gln Leu Asp Asn Pro
            35                  40                  45

Ala Arg Ile Pro Pro Ser Gly Trp Lys Cys Ser Lys Cys Asp Met Arg
        50                  55                  60

Glu Asn Leu Trp Leu Asn Leu Thr Asp Gly Ser Ile Leu Cys Gly Arg
65                  70                  75                  80

Arg Tyr Trp Asp Gly Ser Gly Gly Asn Asn His Ala Val Glu His Tyr
                85                  90                  95

Arg Glu Thr Gly Tyr Pro Leu Ala Val Lys Leu Gly Thr Ile Thr Pro
            100                 105                 110

Asp Gly Ala Asp Val Trp Ser Tyr Asp Glu Asp Met Val Leu Asp
            115                 120                 125

Pro Ser Leu Ala Glu His Leu Ser His Phe Gly Ile Asp Met Leu Lys
        130                 135                 140

Met Gln Lys Gly Ser Cys Ala Ala Glu Glu Ala Glu Gln Ile Ala
145                 150                 155                 160

Tyr Ala Met Gln Met Ser Leu Arg Glu Ala Gly Gly Ser Asp Leu
                165                 170                 175

Leu Cys Lys Lys Gly Cys Gly Tyr Tyr Gly Asn Pro Ala Trp Gln Gly
            180                 185                 190

Phe Cys Ser Lys Cys Trp Arg Glu Glu Ala His Lys Ala Ala Gln Lys
        195                 200                 205

<210> SEQ ID NO 7
<211> LENGTH: 81
<212> TYPE: PRT
<213> ORGANISM: Artificial Sequence
<220> FEATURE:
<223> OTHER INFORMATION: tSR - chimeric polypeptide comprising two
      binding domains that bind ubiquitin in non-overlapping regions

```
<400> SEQUENCE: 7

Met Pro Ser Ser His His His His His Ser Ser Gly Leu Val Pro
1               5                   10                  15

Arg Gly Ser His Met Thr Glu Glu Gln Ile Ala Tyr Ala Met Gln
            20                  25                  30

Met Ser Leu Arg Glu Ala Gly Gly Ser Asp Leu Leu Cys Lys Lys
        35                  40                  45

Gly Cys Gly Tyr Tyr Gly Asn Pro Ala Trp Gln Gly Phe Cys Ser Lys
50                  55                  60

Cys Trp Arg Glu Glu Ala His Lys Cys Ala Ala Glu Arg Ala Ala Ala
65                  70                  75                  80

Glu

<210> SEQ ID NO 8

<400> SEQUENCE: 8

000

<210> SEQ ID NO 9
<211> LENGTH: 18
<212> TYPE: PRT
<213> ORGANISM: Saccharomyces sp.

<400> SEQUENCE: 9

Glu Glu Ala Glu Leu Asp Leu Lys Ala Ala Ile Gln Glu Ser Leu Arg
1               5                   10                  15

Glu Ala

<210> SEQ ID NO 10
<211> LENGTH: 35
<212> TYPE: PRT
<213> ORGANISM: Homo sapiens

<400> SEQUENCE: 10

Ser Asp Leu Leu Cys Lys Lys Gly Cys Gly Tyr Tyr Gly Asn Pro Ala
1               5                   10                  15

Trp Gln Gly Phe Cys Ser Lys Cys Trp Arg Glu Glu Tyr His Lys Ala
            20                  25                  30

Arg Gln Lys
        35

<210> SEQ ID NO 11
<211> LENGTH: 44
<212> TYPE: PRT
<213> ORGANISM: Saccharomyces sp.

<400> SEQUENCE: 11

Pro Pro Glu Glu Arg Tyr Glu His Gln Leu Arg Gln Leu Asn Asp Met
1               5                   10                  15

Gly Phe Phe Asp Phe Asp Arg Asn Val Ala Ala Leu Arg Arg Ser Gly
            20                  25                  30

Gly Ser Val Gln Gly Ala Leu Asp Ser Leu Leu Asn
        35                  40

<210> SEQ ID NO 12
<211> LENGTH: 18
<212> TYPE: PRT
<213> ORGANISM: Homo sapiens
```

<400> SEQUENCE: 12

Glu Glu Ala Glu Glu Gln Ile Ala Tyr Ala Met Gln Met Ser Leu Arg
1               5                   10                  15
Glu Ala

<210> SEQ ID NO 13
<211> LENGTH: 5
<212> TYPE: PRT
<213> ORGANISM: Artificial Sequence
<220> FEATURE:
<223> OTHER INFORMATION: Peptide linker

<400> SEQUENCE: 13

Gly Ser Ala Ala Ala
1               5

<210> SEQ ID NO 14
<211> LENGTH: 3
<212> TYPE: PRT
<213> ORGANISM: Artificial Sequence
<220> FEATURE:
<223> OTHER INFORMATION: Peptide linker

<400> SEQUENCE: 14

Gly Gly Gly
1

<210> SEQ ID NO 15
<211> LENGTH: 12
<212> TYPE: PRT
<213> ORGANISM: Artificial Sequence
<220> FEATURE:
<223> OTHER INFORMATION: Peptide linker

<400> SEQUENCE: 15

Gly Gly Ser Gly Gly Ser Gly Ser Gly Gly Ser Gly
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Peptide linker

<400> SEQUENCE: 16

Gly Gly Gly Gly Gly Ser Ser Gly Gly Gly
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Peptide linker

<400> SEQUENCE: 17

Gly Ser Cys Ala Ala Ala
1               5

<210> SEQ ID NO 18
<211> LENGTH: 6
<212> TYPE: PRT
<213> ORGANISM: Artificial Sequence
<220> FEATURE:

```
<223> OTHER INFORMATION: Peptide linker

<400> SEQUENCE: 18

Gly Ser Cys Ala Ala Ala
1               5

<210> SEQ ID NO 19
<211> LENGTH: 5
<212> TYPE: PRT
<213> ORGANISM: Artificial Sequence
<220> FEATURE:
<223> OTHER INFORMATION: Peptide linker

<400> SEQUENCE: 19

Gly Ser Cys Ala Ala
1               5

<210> SEQ ID NO 20
<211> LENGTH: 3
<212> TYPE: PRT
<213> ORGANISM: Artificial Sequence
<220> FEATURE:
<223> OTHER INFORMATION: Peptide linker

<400> SEQUENCE: 20

Gly Gly Gly
1

<210> SEQ ID NO 21
<211> LENGTH: 3
<212> TYPE: PRT
<213> ORGANISM: Artificial Sequence
<220> FEATURE:
<223> OTHER INFORMATION: Peptide linker

<400> SEQUENCE: 21

Gly Gly Gly
1

<210> SEQ ID NO 22
<211> LENGTH: 76
<212> TYPE: PRT
<213> ORGANISM: Homo sapiens

<400> SEQUENCE: 22

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 23
<211> LENGTH: 76
<212> TYPE: PRT
<213> ORGANISM: Homo sapiens

<400> SEQUENCE: 23

Met Leu Ile Lys Val Lys Thr Leu Thr Gly Lys Glu Ile Glu Ile Asp
1               5                   10                  15
```

Ile Glu Pro Thr Asp Lys Val Glu Arg Ile Lys Glu Arg Val Glu
        20                   25                  30

Lys Glu Gly Ile Pro Pro Gln Gln Gln Arg Leu Ile Tyr Ser Gly Lys
        35                   40                 45

Gln Met Asn Asp Glu Lys Thr Ala Ala Asp Tyr Lys Ile Leu Gly Gly
50                  55                   60

Ser Val Leu His Leu Val Leu Ala Leu Arg Gly Gly
65                  70                  75

<210> SEQ ID NO 24
<211> LENGTH: 96
<212> TYPE: PRT
<213> ORGANISM: Homo sapiens

<400> SEQUENCE: 24

Ser Asp Gln Glu Ala Lys Pro Ser Thr Glu Asp Leu Gly Asp Lys Lys
1                5                   10                 15

Glu Gly Glu Tyr Ile Lys Leu Lys Val Ile Gly Gln Asp Ser Ser Glu
        20                   25                   30

Ile His Phe Lys Val Lys Met Thr Thr His Leu Lys Lys Leu Lys Glu
        35                   40                 45

Ser Tyr Cys Gln Arg Gln Gly Val Pro Met Asn Ser Leu Arg Phe Leu
50                  55                   60

Phe Glu Gly Gln Arg Ile Ala Asp Asn His Thr Pro Lys Glu Leu Gly
65                  70                   75                  80

Met Glu Glu Glu Asp Val Ile Glu Val Tyr Gln Glu Gln Thr Gly Gly
        85                   90                   95

<210> SEQ ID NO 25
<211> LENGTH: 69
<212> TYPE: PRT
<213> ORGANISM: Homo sapiens

<400> SEQUENCE: 25

Met Ala Asp Glu Lys Pro Lys Glu Gly Val Lys Thr Glu Asn Asn Asp
1                5                   10                 15

His Ile Asn Leu Lys Val Ala Gly Gln Asp Gly Ser Val Val Gln Phe
        20                   25                   30

Lys Ile Lys Arg His Thr Pro Leu Ser Lys Leu Met Lys Ala Tyr Cys
        35                   40                 45

Glu Arg Gln Leu Glu Met Glu Asp Glu Asp Thr Ile Asp Val Phe Gln
50                  55                   60

Gln Gln Thr Gly Gly
65

<210> SEQ ID NO 26
<211> LENGTH: 92
<212> TYPE: PRT
<213> ORGANISM: Homo sapiens

<400> SEQUENCE: 26

Met Ser Glu Glu Lys Pro Lys Glu Gly Val Lys Thr Glu Asn Asp His
1                5                   10                 15

Ile Asn Leu Lys Val Ala Gly Gln Asp Gly Ser Val Val Gln Phe Lys
        20                   25                   30

Ile Lys Arg His Thr Pro Leu Ser Lys Leu Met Lys Ala Tyr Cys Glu
        35                   40                 45

```
Arg Gln Gly Leu Ser Met Arg Gln Ile Arg Phe Arg Phe Asp Gly Gln
         50                  55                  60

Pro Ile Asn Glu Thr Asp Thr Pro Ala Gln Leu Glu Met Glu Asp Glu
 65                  70                  75                  80

Asp Thr Ile Asp Val Phe Gln Gln Gln Thr Gly Gly
                 85                  90
```

<210> SEQ ID NO 27
<211> LENGTH: 76
<212> TYPE: PRT
<213> ORGANISM: Artificial Sequence
<220> FEATURE:
<223> OTHER INFORMATION: Modified (S20C) ubiquitin

<400> SEQUENCE: 27

```
Met Gln Ile Phe Val Lys Thr Leu Thr Gly Lys Thr Ile Thr Leu Glu
 1               5                  10                  15

Val Glu Pro Cys Asp Thr Ile Glu Asn Val Lys Ala Lys Ile Gln Asp
                 20                  25                  30

Lys Glu Gly Ile Pro Pro Asp Gln Gln Arg Leu Ile Phe Ala Gly Lys
             35                  40                  45

Gln Leu Glu Asp Gly Arg Thr Leu Ser Asp Tyr Asn Ile Gln Lys Glu
         50                  55                  60

Ser Thr Leu His Leu Val Leu Arg Leu Arg Gly Gly
 65                  70                  75
```

<210> SEQ ID NO 28
<211> LENGTH: 12
<212> TYPE: PRT
<213> ORGANISM: Artificial Sequene
<220> FEATURE:
<223> OTHER INFORMATION: Peptide linker

<400> SEQUENCE: 28

```
Thr Gly Gly Ser Gly Gly Ser Gly Ser Ala Ala Ala
 1               5                  10
```

<210> SEQ ID NO 29

<400> SEQUENCE: 29

000

<210> SEQ ID NO 30
<211> LENGTH: 3
<212> TYPE: PRT
<213> ORGANISM: Artificial Sequence
<220> FEATURE:
<223> OTHER INFORMATION: Peptide linker

<400> SEQUENCE: 30

```
Ala Ala Ala
 1
```

<210> SEQ ID NO 31
<211> LENGTH: 147
<212> TYPE: PRT
<213> ORGANISM: Artificial Sequence
<220> FEATURE:
<223> OTHER INFORMATION: IsoT ZnF (S227C) - Atto532-tagged chimeric
      polypeptide comprising one ubiquitin binding domain

<400> SEQUENCE: 31

Met Pro Ser Ser His His His His His His Ser Ser Gly Leu Val Pro

```
                1               5                   10                  15
        Arg Gly Ser His Met Lys Gln Glu Val Gln Ala Trp Asp Gly Glu Val
                        20                  25                  30

Arg Gln Val Ser Lys His Ala Phe Ser Leu Lys Gln Leu Asp Asn Pro
                        35                  40                  45

Ala Arg Ile Pro Pro Ser Gly Trp Lys Cys Ser Lys Cys Asp Met Arg
                    50                  55                  60

Glu Asn Leu Trp Leu Asn Leu Thr Asp Gly Ser Ile Leu Cys Gly Arg
        65                  70                  75                  80

Arg Tyr Phe Asp Gly Cys Gly Asn Asn His Ala Val His Tyr
                            85                  90                  95

Arg Glu Thr Gly Tyr Pro Leu Ala Val Lys Leu Gly Thr Ile Thr Pro
                        100                 105                 110

Asp Gly Ala Asp Val Tyr Ser Tyr Asp Glu Asp Met Val Leu Asp
                        115                 120                 125

Pro Ser Leu Ala Glu His Leu Ser His Phe Gly Ile Asp Met Leu Lys
                    130                 135                 140

Met Gln Lys
        145

<210> SEQ ID NO 32
<211> LENGTH: 150
<212> TYPE: PRT
<213> ORGANISM: Artificial Sequence
<220> FEATURE:
<223> OTHER INFORMATION: Conjugated ubiquitin molecule

<400> SEQUENCE: 32

Met Gly Ser Ser His His His His His His Ser Ser Gly Leu Val Pro
        1               5                   10                  15

Arg Gly Ser His Met Gln Ile Phe Val Lys Thr Leu Thr Gly Lys Thr
                        20                  25                  30

Ile Thr Leu Glu Val Glu Pro Ser Asp Thr Ile Glu Asn Val Lys Ala
                        35                  40                  45

Lys Ile Gln Asp Lys Glu Gly Ile Pro Pro Asp Gln Gln Arg Leu Ile
                    50                  55                  60

Phe Ala Gly Lys Gln Leu Glu Asp Gly Arg Thr Leu Ser Asp Tyr Asn
        65                  70                  75                  80

Ile Gln Lys Glu Ser Thr Leu His Leu Val Leu Arg Leu Arg Gly Gly
                            85                  90                  95

Gln Tyr Lys Leu Ala Leu Asn Gly Lys Thr Leu Lys Gly Glu Thr Thr
                        100                 105                 110

Thr Glu Ala Val Asp Ala Ala Thr Ala Glu Lys Val Phe Lys Gln Tyr
                        115                 120                 125

Ala Asn Asp Asn Gly Val Asp Gly Glu Trp Thr Tyr Asp Asp Ala Thr
                    130                 135                 140

Lys Thr Phe Thr Val Thr
        145                 150

<210> SEQ ID NO 33
<211> LENGTH: 147
<212> TYPE: PRT
<213> ORGANISM: Homo sapiens

<400> SEQUENCE: 33

Met Ala Leu Lys Arg Ile Asn Lys Glu Leu Ser Asp Leu Ala Arg Asp
        1               5                   10                  15
```

Pro Pro Ala Gln Cys Ser Ala Gly Pro Val Gly Asp Met Phe His
                20                  25                  30

Trp Gln Ala Thr Ile Met Gly Pro Asn Asp Ser Pro Tyr Gln Gly Gly
            35                  40                  45

Val Phe Leu Thr Ile His Phe Pro Thr Asp Tyr Pro Phe Lys Pro
 50                  55                  60

Pro Lys Val Ala Phe Thr Thr Arg Ile Tyr His Pro Asn Ile Asn Ser
 65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
            100                 105                 110

Pro Asn Pro Asp Asp Pro Leu Val Pro Glu Ile Ala Arg Ile Tyr Lys
            115                 120                 125

Thr Asp Arg Asp Lys Tyr Asn Arg Ile Ser Arg Glu Trp Thr Gln Lys
130                 135                 140

Tyr Ala Met
145

<210> SEQ ID NO 34
<211> LENGTH: 21
<212> TYPE: PRT
<213> ORGANISM: Homo sapiens

<400> SEQUENCE: 34

Leu Gln Glu Glu Glu Leu Gln Leu Ala Leu Ala Leu Ser Gln Ser
1               5                   10                  15

Glu Ala Glu Glu Lys
            20

<210> SEQ ID NO 35
<211> LENGTH: 27
<212> TYPE: PRT
<213> ORGANISM: Homo sapiens

<400> SEQUENCE: 35

Gln Lys Gln Ile Gln Glu Asp Trp Glu Leu Ala Glu Arg Leu Gln Arg
1               5                   10                  15

Glu Glu Glu Glu Ala Phe Ala Ser Ser Gln Ser
            20                  25

<210> SEQ ID NO 36
<211> LENGTH: 41
<212> TYPE: PRT
<213> ORGANISM: Saccharomyces cerevisiae

<400> SEQUENCE: 36

Asp His Glu Ser Lys Leu Ser Ile Leu Met Asp Met Phe Pro Ala Ile
1               5                   10                  15

Ser Lys Ser Lys Leu Gln Val His Leu Leu Glu Asn Asn Asp Leu
            20                  25                  30

Asp Leu Thr Ile Gly Leu Leu Leu Lys
            35                  40

<210> SEQ ID NO 37
<211> LENGTH: 70
<212> TYPE: PRT
<213> ORGANISM: Homo sapiens

<400> SEQUENCE: 37

```
His Thr Leu Glu Glu Val Asn Asn Val Arg Leu Leu Ser Glu Met
1               5                   10                  15

Leu Leu His Tyr Ser Gln Glu Asp Ser Asp Gly Asp Arg Glu Leu
            20                  25                  30

Met Lys Glu Leu Phe Asp Gln Cys Glu Asn Lys Arg Thr Leu Phe
        35                  40                  45

Lys Leu Ala Ser Glu Thr Glu Asp Asn Asp Ser Leu Gly Asp Ile
    50                  55                  60

Leu Gln Ala Ser Asp Asn
65                  70
```

<210> SEQ ID NO 38
<211> LENGTH: 135
<212> TYPE: PRT
<213> ORGANISM: Homo sapiens

<400> SEQUENCE: 38

```
Glu Thr Gly Tyr Thr Tyr Ile Leu Pro Lys Asn Val Leu Lys Lys Phe
1               5                   10                  15

Ile Cys Ile Ser Asp Leu Arg Ala Gln Ile Ala Gly Tyr Leu Tyr Gly
            20                  25                  30

Val Ser Pro Pro Asp Asn Pro Gln Val Lys Glu Ile Arg Cys Ile Val
        35                  40                  45

Met Val Pro Gln Trp Gly Thr His Gln Thr Val His Leu Pro Gly Gln
    50                  55                  60

Leu Pro Gln His Glu Tyr Leu Lys Glu Met Glu Pro Leu Gly Trp Ile
65                  70                  75                  80

His Thr Gln Pro Asn Glu Ser Pro Gln Leu Ser Pro Gln Asp Val Thr
                85                  90                  95

Thr His Ala Lys Ile Met Ala Asp Asn Pro Ser Trp Asp Gly Glu Lys
            100                 105                 110

Thr Ile Ile Ile Thr Cys Ser Phe Thr Pro Gly Ser Cys Thr Leu Thr
        115                 120                 125

Ala Tyr Lys Leu Thr Pro Ser
    130                 135
```

<210> SEQ ID NO 39
<211> LENGTH: 29
<212> TYPE: PRT
<213> ORGANISM: Rattus norvegicus

<400> SEQUENCE: 39

```
Thr Ser Ala Met Trp Ala Cys Gln His Cys Thr Phe Met Asn Gln Pro
1               5                   10                  15

Gly Thr Gly His Cys Glu Met Cys Ser Leu Pro Arg Thr
            20                  25
```

<210> SEQ ID NO 40
<211> LENGTH: 29
<212> TYPE: PRT
<213> ORGANISM: Homo sapiens

<400> SEQUENCE: 40

```
Asp Gln Val Pro Cys Glu Lys Cys Gly Ser Leu Val Pro Val Trp Asp
1               5                   10                  15

Met Pro Glu His Met Asp Tyr His Phe Ala Leu Glu Leu
            20                  25
```

```
<210> SEQ ID NO 41
<211> LENGTH: 19
<212> TYPE: PRT
<213> ORGANISM: Homo sapiens

<400> SEQUENCE: 41

Leu Phe Tyr Asp Asp Tyr Glu Asp Gly Val Glu Glu Ala Asp Ser
1               5                   10                  15

Cys Phe Gly

<210> SEQ ID NO 42
<211> LENGTH: 29
<212> TYPE: PRT
<213> ORGANISM: Homo sapiens

<400> SEQUENCE: 42

Leu Pro Glu Gly Val Asp Gln Glu Val Phe Lys Gln Leu Pro Val Asp
1               5                   10                  15

Ile Gln Glu Glu Ile Leu Ser Gly Lys Ser Arg Glu Lys
                20                  25
```

SENSORS AND ASSAYS FOR UBIQUITIN OR UBIQUITIN-LIKE PROTEINS

CROSS-REFERENCE TO RELATED APPLICATIONS

This application is a divisional of U.S. application Ser. No. 14/266,502, filed Apr. 30, 2014, now issued as U.S. Pat. No. 10,018,634, which application claims benefit under 35 U.S.C. § 119(e) of U.S. provisional patent application No. 61/817,517 filed on Apr. 30, 2013, the contents of which are incorporated herein by reference in their entirety.

This invention was made with government support under Grant No. GM097452 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is CSUV_007_02US_ST25.txt. The text file is 29 KB, created on Sep. 5, 2018, and is being submitted electronically via EFS-Web.

BACKGROUND OF THE INVENTION

Ubiquitin is a small, highly conserved protein that is found in all eukaryotic cells. Ubiquitin proteins and ubiquitin-like proteins regulate diverse and vital processes within cells. Ubiquitin proteins have roles in many cell functions including the mediation of various stress responses, repair of damaged DNA, regulation of differential gene expression, and cell cycle control. One of the best characterized roles of ubiquitin proteins is the regulation of selective protein degradation by the proteasome.

Ubiquitin proteins and ubiquitin-like proteins function through their covalent attachment to other proteins, which is also referred to in the art as conjugation. The conjugation of a ubiquitin protein or a ubiquitin-like protein can influence the target protein in a number of ways which include the signaling of the target protein for degradation by the proteasome, changing the activity of the target protein, or changing the cellular localization of the target protein. When a ubiquitin protein is conjugated to a target protein, the target protein is said to be ubiquitinated.

Since ubiquitin proteins and ubiquitin-like proteins act through their conjugation to other proteins, the pools of unconjugated ubiquitin must be regulated for the proper functions of virtually all ubiquitin-dependent signaling pathways. Despite the importance of ubiquitin and ubiquitin like proteins, few methods to measure free ubiquitin proteins have been described. Typically, these methods have low precision or are difficult to implement for many labs. What is needed in the art is a simple, practical assay for free ubiquitin proteins or ubiquitin-like proteins to be measured.

The present invention addresses such needs, providing novel chimeric polypeptide sensors for detecting free ubiquitin proteins or ubiquitin-like proteins or, alternatively, both free and conjugated ubiquitin proteins or ubiquitin-like proteins, and related methods to use the chimeric polypeptide sensors to determine the amount of free ubiquitin in a sample and/or the total amount of ubiquitin in a sample. This invention also provides sensitive assays for free ubiquitin proteins or ubiquitin-like proteins, or total ubiquitin proteins or ubiquitin-like proteins, in a sample, and can be incorporated in experiments to measure free or total ubiquitin or ubiquitin-like proteins in tissues or extracts, and can be used to monitor ubiquitination or deubiquitinase enzyme activities in real-time assays. Alternatively, variants of the invention this invention can be incorporated into screens to identify agents that modify ubiquitin conjugation.

BRIEF SUMMARY OF THE INVENTION

The present invention provides compositions comprising chimeric polypeptides that bind to ubiquitin proteins or ubiquitin-like proteins with high affinity, and methods of using the chimeric polypeptides to determine the amount of ubiquitin proteins or ubiquitin-like proteins in various types of samples. In various embodiments, the chimeric polypeptides bind to only free ubiquitin proteins or free ubiquitin-like proteins, or bind to both free and conjugated ubiquitin proteins or free and conjugated ubiquitin-like proteins.

In some embodiments, the invention provides a chimeric polypeptide comprising: two or more polypeptide sequences that bind a ubiquitin protein or a ubiquitin-like protein, wherein the sequences bind non-overlapping regions of the same ubiquitin protein or ubiquitin-like protein, and one or more linker(s), wherein each linker connects two or more of the sequences. In some embodiments, the chimeric polypeptide preferentially binds to the free ubiquitin protein or the free ubiquitin-like protein as compared to the conjugated ubiquitin protein or the conjugated ubiquitin-like protein. In some embodiments, the chimeric polypeptide binds free and conjugated ubiquitin.

In some embodiments, the invention comprises a chimeric polypeptide, wherein the chimeric polypeptide comprises three polypeptide sequences that bind to non-overlapping regions of the ubiquitin protein or the ubiquitin-like protein, wherein the three polypeptide sequences are connected by two linkers.

In some embodiments, the invention provides a chimeric polypeptide that comprises, in the following order (amino terminal to carboxy terminal): a first polypeptide sequence that binds to a first region of the ubiquitin protein or the ubiquitin-like protein, a first linker that connects the first polypeptide sequence with a second polypeptide sequence, the second polypeptide sequence, which binds to a second region of the ubiquitin protein or the ubiquitin-like protein, a second linker that connects the second polypeptide sequence with a third polypeptide sequence; and the third polypeptide sequence, which binds to a third region of the ubiquitin protein or the ubiquitin like polypeptide, wherein the regions of the ubiquitin protein or the ubiquitin-like protein bound by the first, second, and third polypeptide sequences are non-overlapping. In some embodiments, the chimeric polypeptide comprises linker(s), wherein the linkers are polypeptides.

In some embodiments, the invention provides the chimeric polypeptide, wherein the sequences comprise a sequence that binds to the ubiquitin C terminus. In some embodiments, the chimeric polypeptide comprises a sequence that binds to the ubiquitin hydrophobic patch. In some embodiments, the chimeric polypeptide comprises a sequence that binds to the surface around Asp58 of ubiquitin. In some embodiments, the chimeric polypeptide comprises a sequence that binds to the ubiquitin C terminus and a sequence that binds to the ubiquitin hydrophobic patch. In some embodiments the chimeric polypeptide comprises a sequence that binds to the ubiquitin C terminus and a sequence that binds the surface around Asp58 of ubiquitin.

In some embodiments, the chimeric polypeptide comprises a sequence that binds to the ubiquitin hydrophobic patch and a sequence that binds to surface around Asp58 of ubiquitin. In some embodiments, the chimeric polypeptide comprises a sequence that binds to the ubiquitin C terminus, a sequence that binds to the ubiquitin hydrophobic patch, and a sequence that binds to the surface around Asp58 of ubiquitin.

In some embodiments, the invention provides a chimeric polypeptide, wherein the sequences comprise the zinc finger binding domain of Isopeptidase T. In some embodiments, the chimeric polypeptide comprises sequences comprising a Ruz domain of Rabex-5. In some embodiments, the chimeric polypeptide comprises sequences comprising a ubiquitin interacting motif of Vps27. In some embodiments, the chimeric polypeptide comprises sequences comprising the ubiquitin associated domain of Dsk2. In some embodiments, the chimeric polypeptide comprises sequences comprising a zinc finger binding domain of Isopeptidase T and the Ruz domain of Rabex-5. In some embodiments, the chimeric polypeptide comprises sequences comprising the zinc finger binding domain of Isopeptidase T and the ubiquitin interacting motif of Vps27. In some embodiments, the chimeric polypeptide comprises sequences comprising a Ruz domain of Rabex-5 and the ubiquitin interacting motif of Vps27. In some embodiments, the invention provides a chimeric polypeptide, wherein the sequences comprise the zinc finger binding domain of Isopeptidase T, the Ruz domain of Rabex-5, and the ubiquitin interacting motif of Vps27.

In some embodiments, the chimeric polypeptide comprises sequences comprising the zinc finger binding domain of Isopeptidase T and the ubiquitin associated domain of Dsk2. In some embodiments, the chimeric polypeptide comprises sequences comprising the Ruz domain of Rabex-5 and the ubiquitin associated domain of Dsk2. In some embodiments, the chimeric polypeptide comprises sequences comprising the zinc finger binding domain of Isopeptidase T, the Ruz domain of Rabex-5, and the ubiquitin associated domain of Dsk2.

In some embodiments, the invention provides the chimeric polypeptide, wherein the sequences bind to non-overlapping regions of the ubiquitin protein. In some embodiments, the chimeric polypeptide comprises sequences bind to non-overlapping regions of the ubiquitin-like protein. In some embodiments, the ubiquitin-like protein is Nedd8. In some embodiments, the ubiquitin-like protein is SUMO.

In some embodiments, the invention provides the chimeric polypeptide comprising a detectable label attached to the polypeptide. In some embodiments, the detectable label is a fluorophore. In some embodiments, the chimeric polypeptide comprises a quencher that is attached to the chimeric polypeptide.

In some embodiments, the invention provides a method of determining an amount of a free ubiquitin protein or a free ubiquitin-like protein in a sample, the method comprising: contacting the sample with a chimeric polypeptide that preferentially binds to the free ubiquitin protein or the free ubiquitin-like protein as compared the conjugated ubiquitin protein or the conjugated ubiquitin-like protein for a period of time, wherein the chimeric polypeptide comprises two or more polypeptide sequences that bind the ubiquitin protein or the ubiquitin-like protein, wherein the sequences bind non-overlapping regions of the ubiquitin protein or ubiquitin-like protein; and one or more linker(s), wherein each linker(s) connect two or more of the sequences; and determining: (i) an amount of the free ubiquitin protein or free ubiquitin-like protein bound to the chimeric polypeptide; or (ii) an amount of a free competitor protein bound to the chimeric polypeptide, wherein if step (ii) is performed, the method further comprises step contacting the sample with the free competitor ubiquitin protein or the free competitor ubiquitin-like protein prior to step determining an amount of free competitor protein bound to the chimeric polypeptide, thereby determining the amount of the free ubiquitin protein or the free ubiquitin-like protein in the sample.

In some embodiments, the method comprises contacting the sample with the chimeric polypeptide for the period of time, and determining the amount of the free ubiquitin protein or free ubiquitin-like protein bound to the chimeric polypeptide.

In some embodiments, the chimeric polypeptide is the chimeric polypeptide is any chimeric peptide disclosed by the invention. In some embodiments, the method the chimeric polypeptide is tagged with a detectable label. In some embodiments, the detectable label is a fluorophore. In some embodiments, the method comprises detecting the detectable label. In some embodiments, the detection comprises measuring fluorescence intensity. In some embodiments, the detection comprises measuring fluorescence anisotropy.

In some embodiments, the method further comprises comparing the amount of the bound free ubiquitin protein or the bound free ubiquitin-like protein to a predetermined value or to a control value.

In some embodiments, the determination of an amount of the free ubiquitin protein or free ubiquitin-like protein bound to the chimeric polypeptide further comprises determining the amount of the free ubiquitin competitor protein or the free ubiquitin-like competitor protein bound to the chimeric polypeptide at two or more time points during the period of time. In some embodiments, determining an amount of the free ubiquitin protein or free ubiquitin-like protein bound to the chimeric polypeptide comprises determining the amount of the free ubiquitin competitor protein or the free ubiquitin-like competitor protein bound to the chimeric polypeptide at two or more regular time points throughout the period of time. In some embodiments, the method further comprises comparing the amount of the bound free ubiquitin protein or the bound free ubiquitin-like protein to a predetermined value or to a control value at two or more time points during the period of time.

In some embodiments, the sample is a biological sample. In some embodiments, the biological sample is derived from cultured cells, optionally eukaryotic cells. In some embodiments, the biological sample is derived from a biological tissue, and wherein the biological tissue optionally comprises eukaryotic cells.

In some embodiments, the method of determining an amount of a free ubiquitin protein or a free ubiquitin-like protein in a sample comprises contacting the sample with the chimeric polypeptide that preferentially binds to the free ubiquitin protein or the free ubiquitin-like protein as compared the conjugated ubiquitin protein or the conjugated ubiquitin-like protein for the period of time, contacting the sample with the free competitor ubiquitin protein or the free competitor ubiquitin-like protein, and determining the amount of the free competitor ubiquitin protein or the free competitor ubiquitin-like protein bound to the chimeric polypeptide.

In some embodiments, the chimeric polypeptide is any chimeric peptide disclosed by the invention. In some embodiments, the method the chimeric polypeptide is tagged with a detectable label. In some embodiments, the detectable label is a fluorophore. In some embodiments, the method comprises detecting the detectable label. In some embodiments, the detection comprises measuring fluorescence intensity. In some embodiments, the detection comprises measuring fluorescence anisotropy.

In some embodiments, the further comprises comparing the amount of the free competitor ubiquitin protein or free competitor ubiquitin-like protein bound to the chimeric polypeptide to a predetermined value or a control value.

In some embodiments, determining the amount of the free competitor ubiquitin protein or the free competitor ubiquitin-like protein bound to the chimeric polypeptide comprises determining the amount of the ubiquitin competitor protein or the ubiquitin-like competitor protein bound to the chimeric polypeptide at two or more time points during the period of time. In some embodiments, determining the amount of the free competitor ubiquitin protein or the free competitor ubiquitin-like protein bound to the chimeric polypeptide comprises determining the amount of the ubiquitin competitor protein or the ubiquitin-like competitor protein bound to the chimeric polypeptide at two or more regular time points throughout the period of time.

In some embodiments, the method further comprises comparing the amount of the ubiquitin competitor protein or the ubiquitin-like competitor protein bound to the chimeric polypeptide to a predetermined value or a control value at two or more time points during the period of time.

In some embodiments, the free ubiquitin competitor protein or the free ubiquitin-like competitor protein is tagged with a first detectable label, and the chimeric polypeptide is tagged with a second detectable label.

In some embodiments, the first detectable label and the second detectable label are suitable for performing fluorescence resonance energy transfer (FRET). In some embodiments the first detectable label and the second detectable label are the same. In some embodiments, the first detectable label and the second detectable label are different. In some embodiments, the first detectable label is a fluorophore. In some embodiments, the second detectable label is a fluorophore. In some embodiments, the first detectable label is a quencher and the second detectable label is a fluorophore. In some embodiments, the first detectable label is a fluorophore and the second detectable label is a quencher. In some embodiments, determining the amount of the free competitor ubiquitin protein or the free competitor ubiquitin-like protein bound to the chimeric polypeptide comprises detecting the detectable labels. In some embodiments, the detection comprises measuring fluorescence intensity. In some embodiments, the detection comprises measuring fluorescence anisotropy.

In some embodiments, the method further comprises comparing the amount of the bound ubiquitin protein or bound ubiquitin-like protein to a predetermined value or a control value. In some embodiments, determining the amount of the free competitor ubiquitin protein or the free competitor ubiquitin-like protein bound to the chimeric polypeptide comprises determining the amount of the free ubiquitin competitor protein or the free ubiquitin-like competitor protein bound to the chimeric polypeptide at two or more time points during the period of time. In some embodiments, determining the amount of the free competitor ubiquitin protein or the free competitor ubiquitin-like protein bound to the chimeric polypeptide comprises determining the amount of the ubiquitin competitor protein or the ubiquitin-like competitor protein bound to the chimeric polypeptide at two or more regular time points throughout the period of time In some embodiments, the method further comprises comparing the amount of the ubiquitin competitor protein or the ubiquitin-like competitor protein bound to the chimeric polypeptide to a predetermined value or a control value at two or more time points during the period of time.

In some embodiments, the invention provides a method of determining a total amount of a ubiquitin protein or a conjugated ubiquitin-like protein in a sample, the method comprising contacting the sample with a chimeric polypeptide that binds to both the free and conjugated ubiquitin protein or both the free and conjugated ubiquitin-like protein for a period of time, wherein the chimeric polypeptide comprises two or more polypeptide sequences that bind the ubiquitin protein or the ubiquitin-like protein, wherein the sequences bind non-overlapping regions of the ubiquitin protein or ubiquitin-like protein, and one or more linker(s), wherein each linker(s) connects two or more of the sequences; and determining: an amount of the ubiquitin protein or ubiquitin-like protein bound to the chimeric polypeptide; or an amount of a competitor ubiquitin protein or a competitor ubiquitin-like protein bound to the chimeric polypeptide, wherein if an amount of a competitor ubiquitin protein or a competitor ubiquitin-like protein bound to the chimeric polypeptide is determined, the method further comprises step contacting the chimeric polypeptide sensor or the sample with the competitor ubiquitin protein or the competitor ubiquitin-like protein prior to step determining an amount of a competitor ubiquitin protein or a competitor ubiquitin-like protein bound to the chimeric polypeptide, thereby determining the total amount of the conjugated ubiquitin protein or the conjugated ubiquitin-like protein in the sample.

In some embodiments, the method comprises contacting the sample with the chimeric polypeptide for the period of time, and determining the amount of the ubiquitin protein or ubiquitin-like protein bound to the chimeric polypeptide.

In some embodiments, the chimeric polypeptide is the chimeric polypeptide is any chimeric peptide disclosed by the invention. In some embodiments, the method the chimeric polypeptide is tagged with a detectable label. In some embodiments, the detectable label is a fluorophore. In some embodiments, the method comprises detecting the detectable label. In some embodiments, the detection comprises measuring fluorescence intensity. In some embodiments, the detection comprises measuring fluorescence anisotropy.

In some embodiments, the method further comprises comparing the amount of the bound ubiquitin protein or the bound ubiquitin-like protein to a predetermined value or to a control value. In some embodiments, the method comprises determining the amount of the bound ubiquitin protein or the bound ubiquitin-like protein at two or more regular time points throughout the period of time. In some embodiments, the method comprises comparing the amount of the bound ubiquitin protein or the bound ubiquitin-like protein to a predetermined value or to a control value at two or more time points during the period of time.

In some embodiments, the sample is a biological sample. In some embodiments, the biological sample is derived from cultured cells, optionally eukaryotic cells. In some embodiments, the biological sample is derived from a biological tissue.

In some embodiments, the method comprises contacting the sample with the chimeric polypeptide for the period of time, determining an amount of the competitor ubiquitin protein or the conjugated competitor ubiquitin-like protein bound to the chimeric polypeptide, and contacting the sample or the chimeric polypeptide sensor with the competitor ubiquitin protein or the conjugated competitor ubiquitin-like protein prior to determining an amount of the competitor ubiquitin protein or the conjugated competitor ubiquitin-like protein bound to the chimeric polypeptide.

In some embodiments, the chimeric polypeptide is any chimeric peptide disclosed by the invention. In some embodiments, the method the chimeric polypeptide is tagged with a detectable label. In some embodiments, the detectable label is a fluorophore. In some embodiments, the method comprises detecting the detectable label. In some embodiments, the detection comprises measuring fluorescence intensity. In some embodiments, the detection comprises measuring fluorescence anisotropy.

In some embodiments, the method further comprises: comparing the amount of the competitor ubiquitin protein or the competitor ubiquitin-like protein bound to the chimeric polypeptide to a predetermined value or a control value.

In some embodiments, determining an amount of the competitor ubiquitin protein or the conjugated competitor ubiquitin-like protein bound to the chimeric polypeptide comprises determining the amount of the competitor ubiquitin protein or the competitor ubiquitin-like protein bound to the chimeric polypeptide at two or more time points during the period of time. In some embodiments, determining an amount of the competitor ubiquitin protein or the conjugated competitor ubiquitin-like protein bound to the chimeric polypeptide comprises determining the amount of the competitor ubiquitin protein or the competitor ubiquitin-like protein bound to the chimeric polypeptide at two or more regular time points throughout the period of time.

In some embodiments, the method further comprises comparing the amount of the competitor ubiquitin protein or the competitor ubiquitin-like protein bound to the chimeric polypeptide to a predetermined value or a control value at two or more time points during the period of time.

In some embodiments, the competitor ubiquitin protein or the competitor ubiquitin-like protein is tagged with a first detectable label, and the chimeric polypeptide is tagged with a second detectable label. In some embodiments, the first detectable label and the second detectable label are suitable for performing fluorescence resonance energy transfer (FRET). In some embodiments, the first detectable label and the second detectable label are the same. In some embodiments, the first detectable label and the second detectable label are different. In some embodiments, the first detectable label is a fluorophore. In some embodiments, the second detectable label is a fluorophore. In some embodiments, the first detectable label is a quencher and the second detectable label is a fluorophore. In some embodiments, the first detectable label is a fluorophore and the second detectable label is a quencher. In some embodiments, the method comprises detecting the detectable labels. In some embodiments, the detection comprises measuring fluorescence intensity. In some embodiments, the detection comprises measuring fluorescence anisotropy.

In some embodiments, the method further comprises comparing the amount of the bound ubiquitin protein or bound ubiquitin-like protein to a predetermined value or a control value. In some embodiments, the method comprises determining the amount of the competitor ubiquitin protein or the competitor ubiquitin-like protein bound to the chimeric polypeptide at two or more time points during the period of time.

In some embodiments, the method comprises determining the amount of the competitor ubiquitin protein or the competitor ubiquitin-like protein bound to the chimeric polypeptide at two or more regular time points throughout the period of time. In some embodiments, the method further comprises comparing the amount of the competitor ubiquitin protein or the competitor ubiquitin-like protein bound to the chimeric polypeptide to a predetermined value or a control value at two or more time points during the period of time.

In some embodiments, the invention provides a method of determining a deubiquitinase activity of a known or candidate deubiquitinase, comprising providing a mixture, comprising a chimeric polypeptide, wherein the chimeric polypeptide preferentially binds to a free ubiquitin protein or a free ubiquitin-like protein as compared to the conjugated ubiquitin protein or the conjugated ubiquitin-like protein comprising two or more polypeptide sequences that bind a ubiquitin protein or a ubiquitin-like protein, wherein the sequences bind non-overlapping regions of the ubiquitin protein or ubiquitin-like protein, and one or more linkers, wherein each linker connects two or more of the sequences; and a conjugated ubiquitin; contacting the mixture with a known or candidate deubiquitinase for a period of time; and determining an amount of free ubiquitin in the mixture, thereby determining the deubiquitinase activity of the known or candidate deubiquitinase.

In some embodiments, the method further comprises, comparing the amount of the free ubiquitin determined to the the amount of the free ubiquitin determined prior to contacting the mixture with a known or candidate deubiquitinase for a period of time or determining the amount of free ubiquitin in a negative control, wherein a greater amount of free ubiquitin after contact with the known or candidate deubiquitinase indicates that the known or candidate deubiquitinase decreases conjugation of the ubiquitin protein or the ubiquitin-like protein, and a lesser amount of free ubiquitin associated with the presence of the known or candidate deubiquitinase indicates that the known or candidate deubiquitinase increases the conjugation of the ubiquitin protein or the ubiquitin-like protein.

In some embodiments, the method further comprises comparing the amount of free ubiquitin determined at a first timepoint to the amount of free ubiquitin determined at one or more subsequent time point(s), wherein a greater amount of free ubiquitin determined at the one or more subsequent time point(s) indicates that the known deubiquitinase or the candidate deubiquitinase is a deubiquitinase of the ubiquitin protein or the ubiquitin-like protein.

In some embodiments, the method comprises, providing a plurality of independently addressable mixtures, each comprising the chimeric polypetide and a different conjugated ubiquitin; contacting each of the mixtures with the known deubiquitinase or the candidate deubiquitinase for a period of time, and determining the amount of the free ubiquitin protein or free ubiquitin-like protein bound to the chimeric polypeptide in each of the mixtures, thereby determining the deubiquinase activity of the known deubiquitinase or candiate deubiquitinase for each of the different ubiquitins in the mixtures.

In some embodiments, the chimeric polypeptide is the chimeric polypeptide is any chimeric peptide disclosed by the invention. In some embodiments, the method the chimeric polypeptide is tagged with a detectable label. In some embodiments, the detectable label is a fluorophore. In some embodiments, the method comprises detecting the detectable label. In some embodiments, the detection comprises measuring fluorescence intensity. In some embodiments, the detection comprises measuring fluorescence anisotropy.

In some embodiments, the method further comprises comparing the amount of the bound free ubiquitin protein or the bound free ubiquitin-like protein to a predetermined value or to a control value. In some embodiments, the method further comprises comparing the amount of the bound free ubiquitin protein or the bound free ubiquitin-like protein to a predetermined value or to a control value at two or more time points during the period of time.

In some embodiments, the chimeric polypeptide is the chimeric polypeptide is any chimeric peptide disclosed by the invention. In some embodiments, the method the chimeric polypeptide is tagged with a detectable label. In some embodiments, the detectable label is a fluorophore. In some embodiments, the method comprises detecting the detectable label. In some embodiments, the detection comprises measuring fluorescence intensity. In some embodiments, the detection comprises measuring fluorescence anisotropy.

In some embodiments, the method further comprises comparing the amount of the competitor ubiquitin protein or the competitor ubiquitin-like protein bound to the chimeric polypeptide to a predetermined value or a control value. In some embodiments, the method further comprises comparing the amount of the competitor ubiquitin protein or the competitor ubiquitin-like protein bound to the chimeric polypeptide to a predetermined value or a control value at two or more time points during the period of time.

In some embodiments, the competitor ubiquitin protein or the competitor ubiquitin-like protein is tagged with a first detectable label, and the chimeric polypeptide is tagged with a second detectable label. In some embodiments, the first detectable label and the second detectable label are suitable for performing fluorescence resonance energy transfer (FRET). In some embodiments, the first detectable label and the second detectable label are the same. In some embodiments, the first detectable label and the second detectable label are different. In some embodiments, the first detectable label is a fluorophore. In some embodiments, the second detectable label is a fluorophore. In some embodiments, the first detectable label is a quencher and the second detectable label is a fluorophore. In some embodiments, the first detectable label is a fluorophore and the second detectable label is a quencher. In some embodiments, the method comprises detecting the detectable labels. In some embodiments, the detection comprises measuring fluorescence intensity. In some embodiments, the detection comprises measuring fluorescence anisotropy.

In some embodiments, the method further comprises comparing the amount of the competitor ubiquitin protein or the competitor ubiquitin-like protein bound to the chimeric polypeptide to a predetermined value or a control value at two or more time points during the period of time.

In some embodiments, the invention provides a method of identifying an agent that modulates the conjugation of a ubiquitin protein or a ubiquitin-like protein to a substrate, the method comprising contacting a mixture comprising a ubiquitin substrate or a ubiquitin-like protein substrate with the ubiquitin protein or the ubiquitin-like protein and a candidate agent for a period of time; contacting the ubiquitin protein or the ubiquitin-like protein with a chimeric polypeptide, wherein the chimeric polypeptide preferentially binds to the free ubiquitin protein or the free ubiquitin-like protein as compared to the conjugated ubiquitin protein or the conjugated ubiquitin-like protein comprising: two or more polypeptide sequences that bind a ubiquitin protein or a ubiquitin-like protein, wherein the sequences bind non-overlapping regions of the ubiquitin protein or ubiquitin-like protein and one or more linkers, wherein each linker connects two or more of the sequences; determining an amount of the free ubiquitin protein or free ubiquitin-like protein bound to the chimeric polypeptide; or an amount of a competitor ubiquitin protein or a competitor ubiquitin-like protein bound to the chimeric polypeptide, wherein if an amount of a competitor ubiquitin protein or a competitor ubiquitin-like protein bound to the chimeric polypeptide is determined, the method further comprises contacting the chimeric polypeptide sensor with the competitor ubiquitin protein or the competitor ubiquitin-like protein prior determining the amount of a competitor ubiquitin protein or a competitor ubiquitin-like protein bound to the chimeric polypeptide.

In some embodiments, the method comprises contacting the mixture comprising the ubiquitin substrate or the ubiquitin-like protein substrate with the ubiquitin protein or the ubiquitin-like protein and the candidate agent, contacting the ubiquitin protein or the ubiquitin-like protein with the chimeric polypeptide, determining an amount of the free ubiquitin protein or free ubiquitin-like protein bound to the chimeric polypeptide; and comparing the amount of the free ubiquitin determined to the amount of the free ubiquitin determined when using a negative control instead of the candidate agent, wherein a greater amount of free ubiquitin associated with the presence of the candidate agent indicates that the candidate agent decreases conjugation of the ubiquitin protein or the ubiquitin-like protein, and wherein a lesser amount of free ubiquitin associated with the presence of the candidate agent indicates that the candidate agent increases the conjugation of the ubiquitin protein or the ubiquitin-like protein.

In some embodiments, the method comprises contacting the mixture comprising the ubiquitin substrate or the ubiquitin-like protein substrate with the ubiquitin protein or the ubiquitin-like protein and the candidate agent; contacting the ubiquitin protein or the ubiquitin-like protein with the chimeric polypeptide; determining an amount of the competitor ubiquitin protein or the competitor ubiquitin-like protein bound to the chimeric polypeptide; and contacting the chimeric polypeptide sensor with the competitor ubiquitin protein or the competitor ubiquitin-like protein prior to determining an amount of the competitor ubiquitin protein or the competitor ubiquitin-like protein bound to the chimeric polypeptide; comparing the amount of the bound competitor protein determined to the amount of the bound competitor protein determined when using a negative control instead of the candidate agent, wherein a greater amount of the bound competitor protein associated with the presence of the candidate agent indicates that the candidate agent increases conjugation of the ubiquitin protein or the ubiquitin-like protein, and wherein a lesser amount of the bound competitor protein associated with the presence of the candidate agent indicates that the candidate agent decreases the conjugation of the ubiquitin protein or the ubiquitin-like protein.

In some embodiments, the chimeric polypeptide is the chimeric polypeptide is any chimeric peptide disclosed by the invention. In some embodiments, the method the chimeric polypeptide is tagged with a detectable label. In some embodiments, the detectable label is a fluorophore. In some embodiments, the method comprises detecting the detectable label. In some embodiments, the detection comprises measuring fluorescence intensity. In some embodiments, the detection comprises measuring fluorescence anisotropy.

In some embodiments, the method comprises determining the amount of the competitor ubiquitin protein or the competitor ubiquitin-like protein bound to the chimeric polypeptide at two or more time points during the period of time. In some embodiments, the method comprises determining the amount of the competitor ubiquitin protein or the competitor ubiquitin-like protein bound to the chimeric polypeptide at two or more regular time points throughout the period of time.

In some embodiments, the competitor ubiquitin protein or the competitor ubiquitin-like protein is tagged with a detectable label. In some embodiments, the detectable label is a fluorophore. In some embodiments, the method comprises detecting the detectable label. In some embodiments, the detecting comprises measuring fluorescence intensity. In some embodiments, the detecting comprises measuring fluorescence anisotropy.

In some embodiments, the competitor ubiquitin protein or the competitor ubiquitin-like protein is tagged with a first detectable label, and the chimeric polypeptide is tagged with a second detectable label. In some embodiments, the first detectable label and the second detectable label are suitable for performing fluorescence resonance energy transfer (FRET). In some embodiments, the first detectable label and the second detectable label are the same. In some embodiments, the first detectable label and the second detectable label are different. In some embodiments, the first detectable label is a fluorophore. In some embodiments, the second detectable label is a fluorophore. In some embodiments, the first detectable label is a quencher and the second detectable label is a fluorophore. In some embodiments, the first detectable label is a fluorophore and the second detectable label is a quencher. In some embodiments, the method comprises detecting the detectable labels. In some embodiments, the detection comprises measuring fluorescence intensity. In some embodiments, the detection comprises measuring fluorescence anisotropy.

In some embodiments, the method comprises determining the amount of the competitor ubiquitin protein or the competitor ubiquitin-like protein bound to the chimeric polypeptide at two or more time points during the period of time. In some embodiments, the method comprises determining the amount of the competitor ubiquitin protein or the competitor ubiquitin-like protein bound to the chimeric polypeptide at two or more regular time points throughout the period of time.

In some embodiments, the invention provides a method of determining an amount of an intact extracellular ubiquitin protein in a sample containing serum, the method comprising: contacting the sample with a chimeric polypeptide that preferentially binds to the intact extracellular ubiquitin protein, wherein the chimeric polypeptide comprises: two or more polypeptide sequences that bind the ubiquitin protein or the ubiquitin-like protein, wherein the sequences comprise a sequence that binds to the ubiquitin C-terminus or the ubiquitin-like protein C-terminus and wherein the sequences bind non-overlapping regions of the ubiquitin protein or the ubiquitin-like protein; and one or more linker(s), wherein the linker(s) connect two or more of the sequences; and determining an amount of the intact extracellular ubiquitin protein bound to the chimeric polypeptide; or an amount of a competitor ubiqutin protein or a competitor ubiquitin-like protein bound to the chimeric polypeptide, wherein if the amount of a competitor ubiqutn protein or a competitor ubiquitin-like protein bound to the chimeric polypeptide is determined, the method further comprises contacting the sample with the competitor ubiquitin protein or the competitor ubiquitin-like protein prior to determining an amount of a competitor ubiqutn protein or a competitor ubiquitin-like protein bound to the chimeric polypeptide, thereby determining the amount of the intact extracellular ubiquitin protein in the sample.

In some embodiments, the method comprises contacting the sample with the chimeric polypeptide for the period of time; and determining the amount of the intact extracellular ubiquitin protein bound to the chimeric polypeptide.

In some embodiments, the method the chimeric polypeptide is tagged with a detectable label. In some embodiments, the detectable label is a fluorophore. In some embodiments, the method comprises detecting the detectable label. In some embodiments, the detection comprises measuring fluorescence intensity. In some embodiments, the detection comprises measuring fluorescence anisotropy.

In some embodiments, the method further comprises comparing the amount of the bound intact extracellular ubiquitin protein to a predetermined value or to a control value. In some embodiments, the method comprises contacting the sample with the chimeric polypeptide for the period of time determining the amount of the competitor protein bound to the chimeric polypeptide.

In some embodiments, the competitor ubiquitin protein or the competitor ubiquitin-like protein is tagged with a detectable label. In some embodiments, the detectable label is a fluorophore. In some embodiments, the method comprises detecting the detectable label. In some embodiments, the detecting comprises measuring fluorescence intensity. In some embodiments, the detecting comprises measuring fluorescence anisotropy.

In some embodiments, the method further comprises, comparing the amount of the competitor ubiquitin protein or competitor ubiquitin-like protein bound to the chimeric polypeptide to a predetermined value or a control value.

In some embodiments, the competitor ubiquitin protein or the competitor ubiquitin-like protein is tagged with a first detectable label, and the chimeric polypeptide is tagged with a second detectable label. In some embodiments, the first detectable label and the second detectable label are suitable for performing fluorescence resonance energy transfer (FRET). In some embodiments, the first detectable label and the second detectable label are the same. In some embodiments, the first detectable label and the second detectable label are different. In some embodiments, the first detectable label is a fluorophore. In some embodiments, the second detectable label is a fluorophore. In some embodiments, the first detectable label is a quencher and the second detectable label is a fluorophore. In some embodiments, the first detectable label is a fluorophore and the second detectable label is a quencher. In some embodiments, the method comprises detecting the detectable labels. In some embodiments, the detection comprises measuring fluorescence intensity. In some embodiments, the detection comprises measuring fluorescence anisotropy.

In some embodiments, the method further comprises comparing the amount of the bound ubiquitin protein or bound ubiquitin-like protein to a predetermined value or a control value.

Other objects, features, and advantages of the present invention will be apparent to one of skill in the art from the following detailed description and figures.

DESCRIPTIONS OF THE FIGURES

FIG. 1 provides a schematic illustration of the design concept for the chimeric polypeptide sensors for free ubiquitin. Ubiquitin is depicted interacting with three binding domains that bind non-overlapping regions of ubiquitin (top). An example chimeric polypeptide comprising three domains connected by two linkers is depicted binding to ubiquitin at three non-overlapping sites (bottom).

FIG. 2 provides a construction scheme for the chimeric polypeptide. Here, the depicted polypeptide has 3 domains, a domain that binds the ubiquitin C terminus, a domain that binds the ubiquitin hydrophobic patch, and a domain that binds to the surface of ubiquitin near Asp58, that are connected by two linkers.

FIG. 3 provides schematic diagrams of two prototype chimeric polypeptides comprising three binding domains that bind ubiquitin in non-overlapping regions. Both prototype polypeptides contain a domain that binds the ubiquitin C terminus, a domain that binds the ubiquitin hydrophobic patch, and a domain that binds to the surface of ubiquitin near Asp58. The binding domains are connected by polypeptide linkers. In the first prototype (tIVR) the domain that binds to the C terminus of ubiquitin is the zinc finger domain of Isopeptidase T ($IsoT^{ZnF}$), the domain that binds to the ubiquitin hydrophobic patch is the ubiquitin-interaction motif from the Vps27 protein ($Vps27^{UIM}$), and the domain that binds to the surface of ubiquitin near Asp58 is the Rabex-5 ubiquitin binding zinc finger (Ruz). In the second prototype (tIDR), the $IsoT^{ZnF}$ and Ruz domains are linked to the ubiquitin associated (UBA) domain of the Dsk2 protein ($Dsk2^{UBA}$), which binds to the ubiquitin hydrophobic patch. Below the schematics, the amino acid sequences of $Vps27^{UIM}$, Ruz, $IsoT^{ZnF}$, and $Dsk2^{UBA}$ are shown in the tIVR and tIDR chimeric polypeptides.

FIG. 4 shows structural models of tIVR and tIDR bound to ubiquitin.

FIG. 5 provides the affinities of tIVR and tIDR to fluorophore-tagged ubiquitin. The values were calculated from assays incorporating fluorophore-labeled ubiquitin. Experiments were performed with fluorescein, Atto532, and Alexa488-tagged ubiquitin tagged with the indicated fluorophore at residue 20. The experimentally determined $K_d$ values are presented in the table.

FIG. 6 shows the binding curves of tIVR and tIDR to free ubiquitin. Affinity of tIVR to free ubiquitin was measured by detecting fluorescence anisotropy. Different concentrations of free ubiquitin were added to 150 pM (top, left). Affinity between Alexa488-tagged ubiquitin and Atto532-tagged was measured by detecting change in fluorescence intensity. Different concentrations of tIVR were added to 50 pM Atto532-tagged ubiquitin or 100 pM Alexa488-tagged tagged ubiquitin (bottom, left). Binding between fluorescein tagged ubiquitin and tIDR also was measured as the ratio of association and dissociation rates (right panel). Changes in fluorescence anisotropy of 50 nM fluorescein tagged ubiquitin were measured with and without 26 nM tIDR to measure association. Dissociation of 50 nM tIDR from 50 nM fluorescein tagged ubiquitin was measured by detecting change in fluorescence anisotropy.

Figure 7:
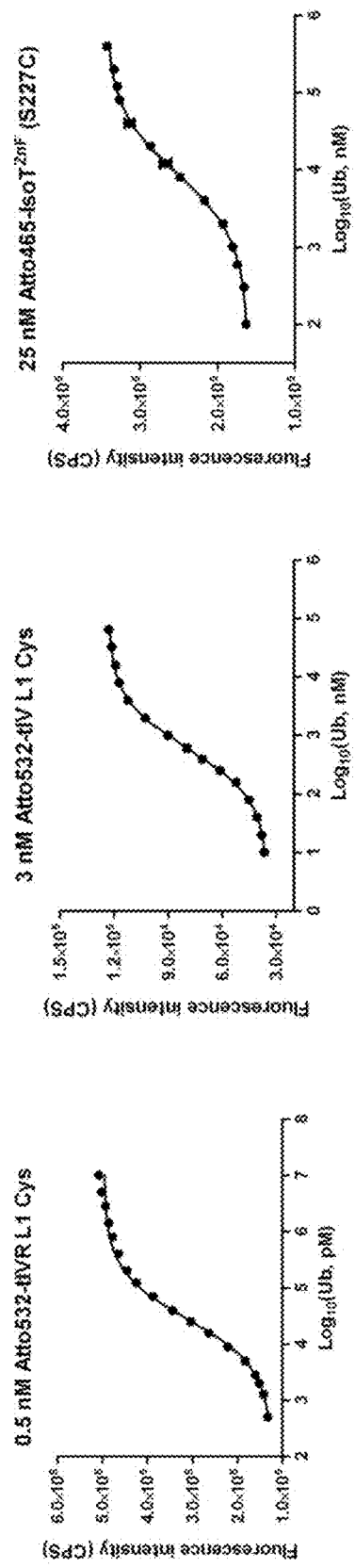

FIG. 7 shows a table and graphs showing that various chimeric polypeptide sensors with different ubiquitin binding domains have different affinities for free ubiquitin. The affinities (as $K_d$ values) of Atto532-tagged chimeric polypeptides comprising one, two, or three ubiquitin binding domains are displayed in the table (top). The graphs show the fluorescence intensities of mixtures of the Atto532-tagged chimeric peptides measured as a function of free ubiquitin concentration; the lines are fits to single-site binding isotherms (bottom). Curves generated from experiments such as these can be used as a calibration standard in assays to measure free ubiquitin proteins in complex biological samples.

FIG. 8 provides a graph and a table showing the affinity of tIVR to free ubiquitin, conjugated ubiquitin and Nedd8. The tIVR polypeptide has an approximately 3000-fold higher affinity for free ubiquitin than for conjugated ubiquitin or free Nedd8. A competition assay was performed to determine the binding affinity of tIVR to free ubiquitin, conjugated ubiquitin, or Nedd8 (top). When bound to tIVR, the Atto532-tagged ubiquitin display reduced fluorescent intensity when stimulated compared to Atto532-tagged ubiquitin that is unbound to tIVR. Fluorescence intensity at 551 nm was measured in counts per second (CPS). The competitor proteins, free ubiquitin (circles), conjugated ubiquitin (triangles), or Nedd8 (squares) were added to a 10 nM tIVR and 10 nM Atto532-tagged ubiquitin mixture. Since Atto532-tagged ubiquitin displaced from tIVR has enhanced fluorescence emission, increased fluorescence intensity indicates binding of competitor proteins to tIVR. A table lists the $K_i$ values for tIVR for free ubiquitin, conjugated ubiquitin, and Nedd8 (bottom).

FIG. 9 provides a graph and a table showing that tIVR has similar binding affinities for different kinds of conjugated free ubiquitin. A competition assay was performed testing 0.8 nM Atto532 tagged ubiquitin and 6 nM tIVR. Fluorescence intensity was measured as different concentrations of different linkage types of conjugated ubiquitin proteins were added (top). The binding affinities, shown as Ki values, of each linkage type of di- or poly-ubiquitin are listed in the table (bottom).

FIG. 10 provides a diagram of tIVR with normal length or shortened linker and binding with conjugated ubiquitin and a table reporting the binding properties of tIVR with a shortened linker. Reducing the length of the linker connecting the domain that binds the ubiquitin C terminus with the domain that binds the ubiquitin hydrophobic patch increases the binding specificity of tIVR to free ubiquitin compared to conjugated ubiquitin.

FIG. 11 provides a table demonstrating that an optimized linker 1 in tIVR is short and made more rigid by having a high fraction of Ala residues. The table lists $K_d$ to Atto532-tagged ubiquitin and Ub-GB1 a model of conjugated ubiquitin, and ratio of affinities for free ubiquitin over conjugated ubiquitin, for a short tIVR linker 1 (SEQ ID NO: 30), a different short linker 1 for tIVR (SEQ ID NO: 13), or a long tIVR linker 1 (SEQ ID: 28).

Figure 12:
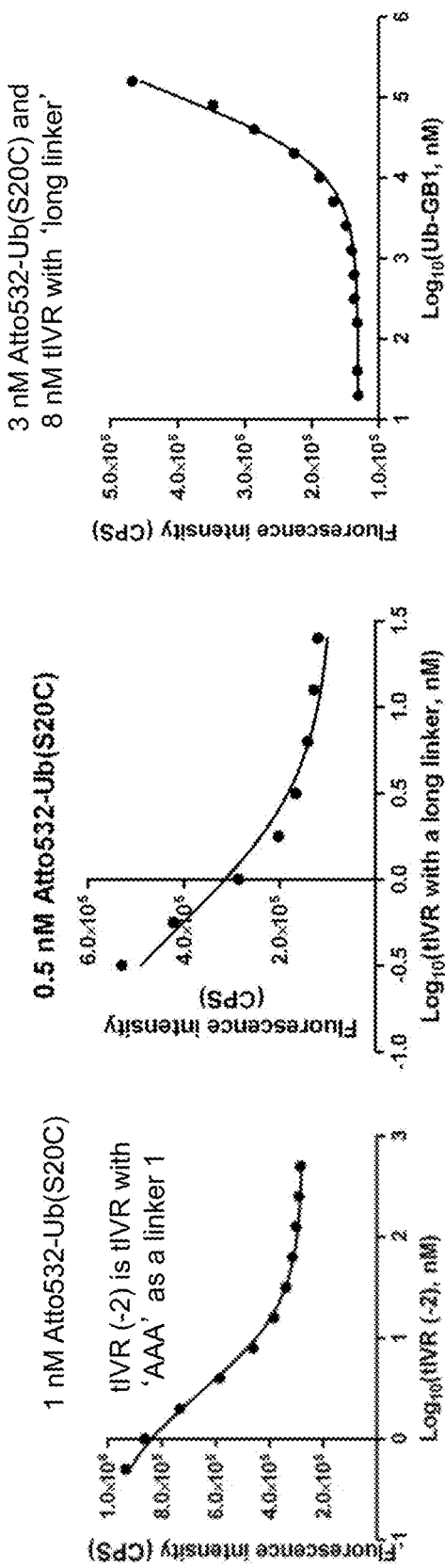

FIG. 12 provides graphs that evaluate the binding of Atto532-tagged ubiquitin and Ub-GB1 to tIVR with linker 1 variants. Different concentrations of tIVR with a short linker 1 (SEQ ID NO: 30) are added to a mixture containing 1 nM atto532 tagged ubiquitin (left). Different concentrations of tIVR containing a long linker 1 (SEQ ID NO: 28) are added to a mixture containing 0.5 nM Atto532-tagged ubiquitin (middle). Different concentrations of Ub-GB1 are added to a mixture containing 3 nM Atto532-tagged ubiquitin and 8 nM tIVR with a long linker 1 (SEQ ID NO: 28; right).

Figure 13:
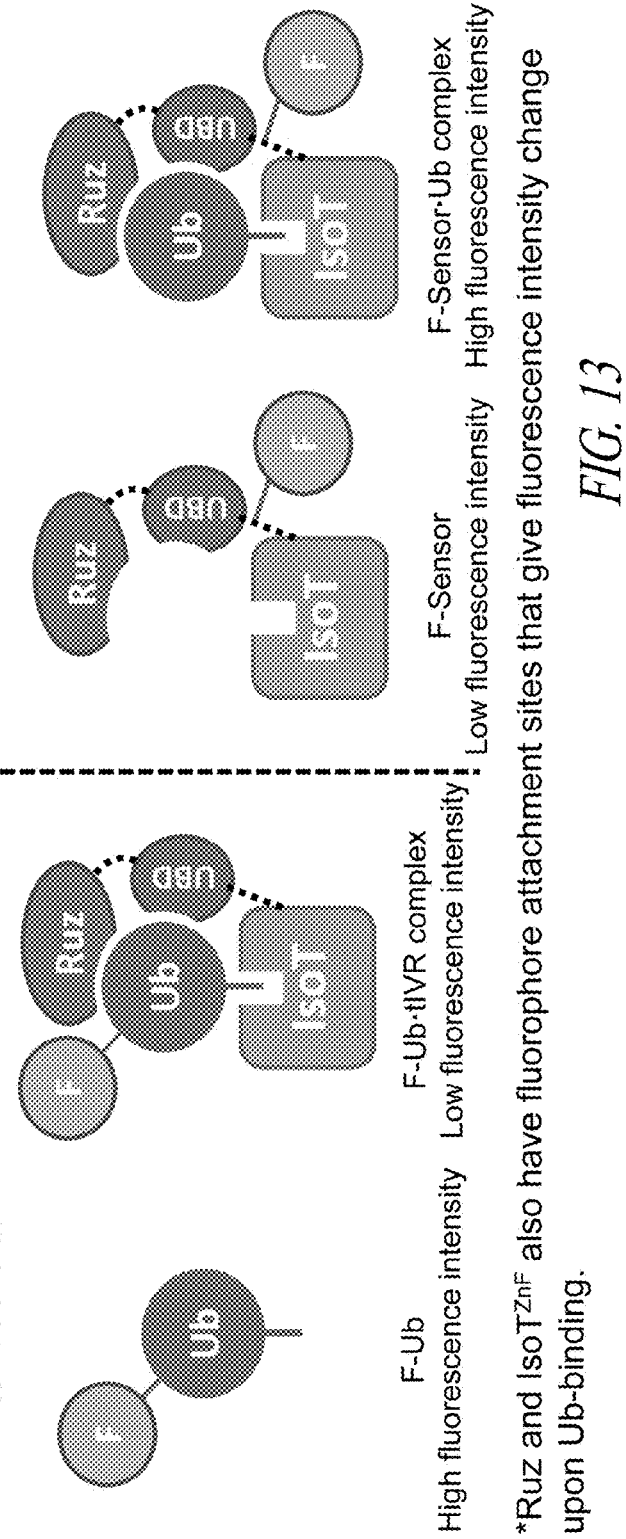

FIG. 13 provides illustrations of how the chimeric peptide sensors can be used with assays that measure fluorescence intensity. When chimeric polypeptide sensors bind a fluorophore-tagged ubiquitin protein, the fluorescence intensity is reduced compared to when the fluorophore-tagged ubiquitin is unbound (left). When a fluorophore-tagged chimeric polypeptide sensor is bound to a ubiquitin protein, the fluorescence intensity is increased compared to when the chimeric polypeptide is unbound (right).

Figure 14:
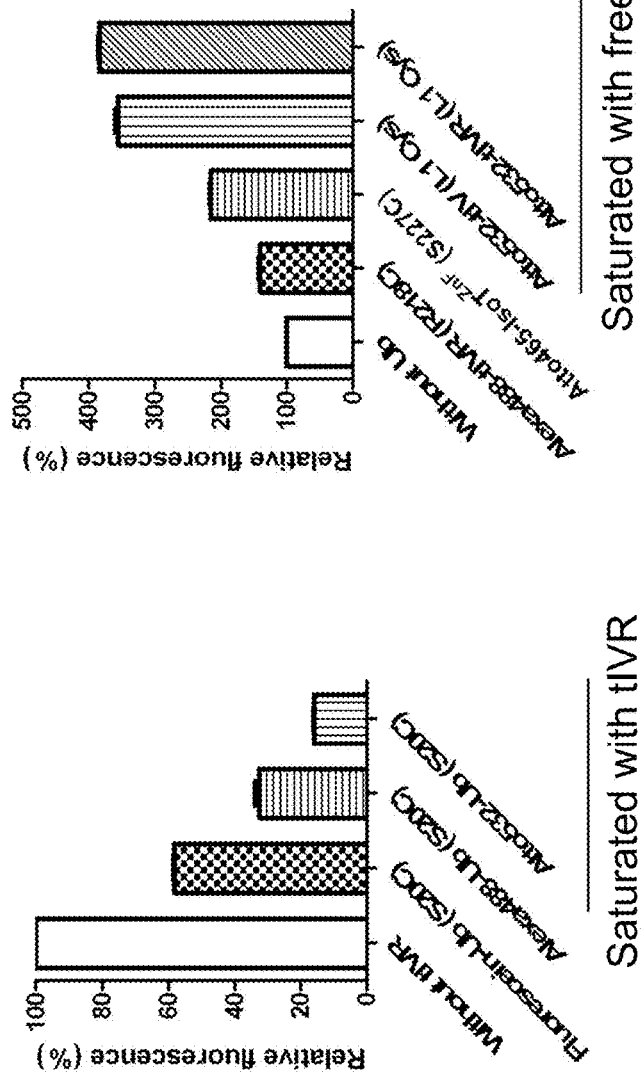

FIG. 14 provides graphs showing that unbound fluorophore-tagged ubiquitins have altered fluorescence intensity compared to fluorophore-tagged ubiquitin bound to tIVR. The percentage decrease of the fluorescence intensity of fluorescein, Alexa488, or Atto532-tagged ubiquitin in the presence of tIVR compared to the absence of tIVR is graphed (left). The percentage change of fluorescence intensity of Alexa586, Atto532, and Alexa488-tagged chimeric polypeptide sensors with three, two, or one ubiquitin binding domains upon binding free ubiquitin is graphed (right).

FIG. 15 provides a graph showing that Atto532-tISR L1 Cys2 shows a large fluorescence intensity change upon binding to ubiquitin. In this chimeric polypeptide sensor, the L1 Cys2, the linker between the IsoT$^{ZnF}$ and the UIM, has a Cys conjugated with the fluorophore. Relative fluorescence intensity of Atto532-tISR L1 Cys2 is shown with different concentrations of free ubiquitin proteins (triangles) or conjugated ubiquitin proteins.

Figure 16:
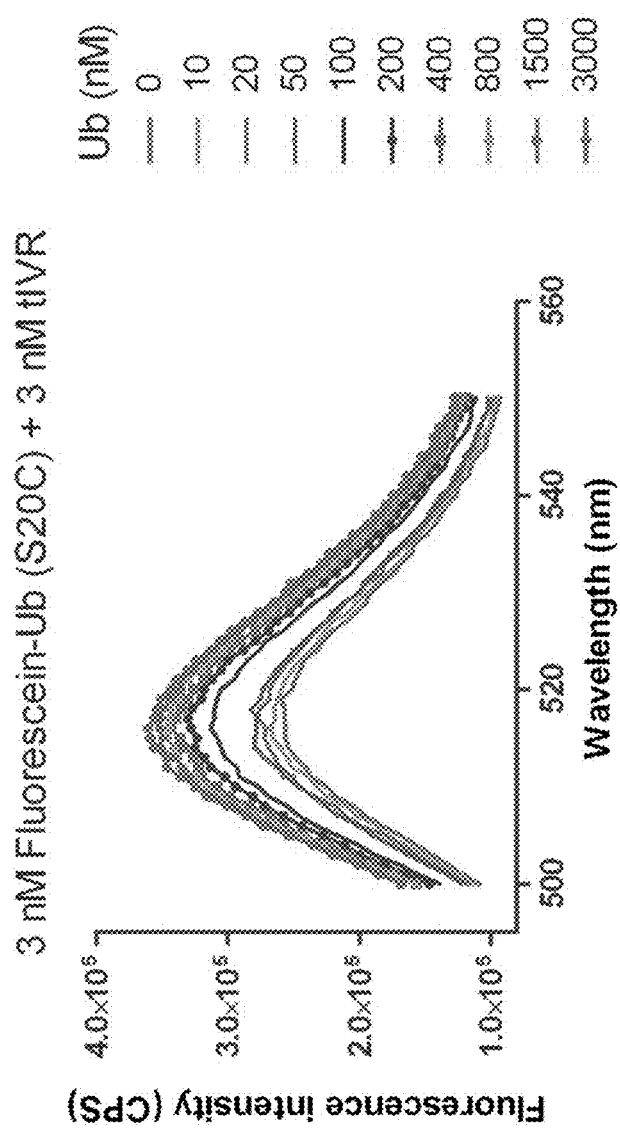

FIG. 16 provides a graph showing that fluorescence intensity changes with increasing amounts of free untagged ubiquitin. Fluorescence intensities of emissions across 500 nm to 550 nm wavelengths of 3 nM fluorescein-tagged ubiquitin with 3 nM tIVR was measured. Concentrations ranging from 0 to 3000 nM of free untagged ubiquitin were added to the mixture. Fluorescence intensity increased with higher concentrations of free ubiquitin. Further, there was no shift observed in the fluorescence emission wavelength due to binding of free ubiquitin.

Figure 17:
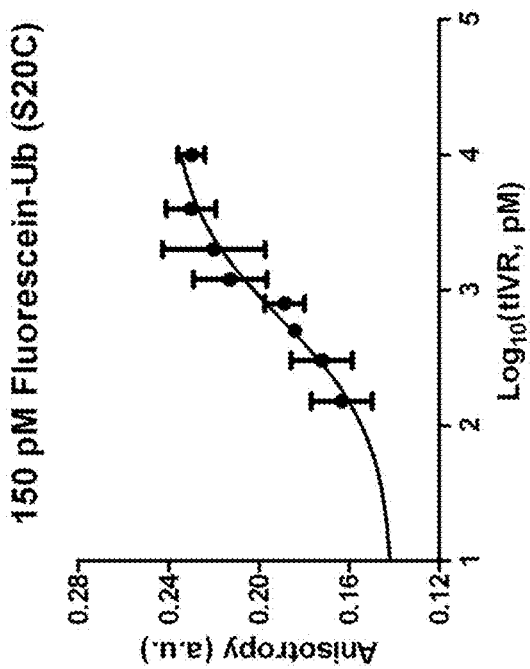

FIG. 17 provides a graph showing that anisotropy of fluorescein-tagged ubiquitin proteins is changed when bound by tIVR. Anisotropy of mixtures with 150 pM fluorescein-tagged ubiquitin proteins was measured and concentrations of tIVR (0-10 nM) were added. Fluorescence was stimulated with polarized light at a 492 nm wavelength and polarized light emission was measured at 518 nm. Increasing the concentration of tIVR increased the anisotropy measured in the mixtures.

Figure 18:
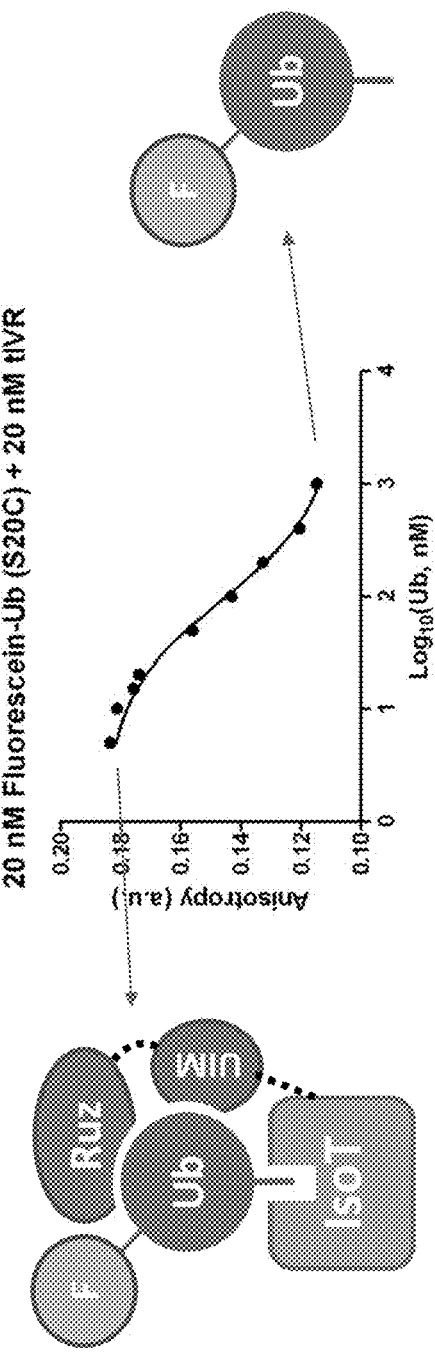

FIG. 18 provides a diagram of fluorophore-tagged ubiquitin proteins bound and unbound to tIVR, and a graph showing that anisotropy of fluorophore-tagged ubiquitin proteins decreases when they are released from tIVR. Anisotropy of a mixture of 20 nM fluoroscein-tagged ubiquitin proteins and 20 nM tIVR was measured. Adding free ubiquitin proteins to the mixture displaced fluorophore-tagged ubiquitin proteins and reduced the anisotropy measured from the mixture. The curve generated from this experiment can be used as a calibration standard in assays to measure free ubiquitin proteins in complex biological samples.

Figure 19:
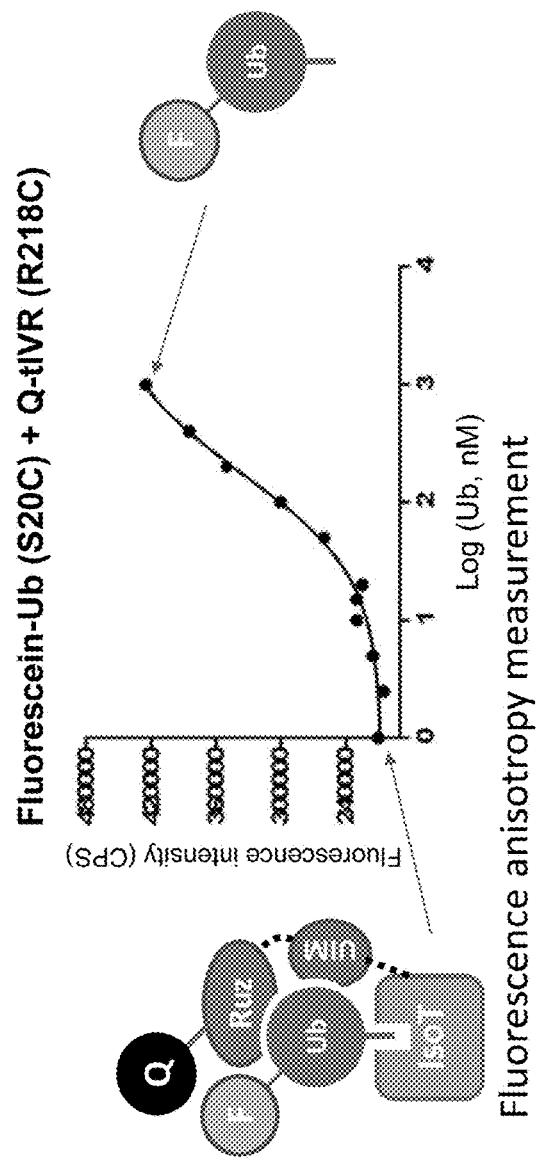

FIG. 19 provides a graph showing that free ubiquitin proteins change the amount of quenching due to FRET between quencher-tagged tIVR and fluorophore-tagged ubiquitin proteins. When the tagged ubiquitin protein is bound to the tIVR, the fluorescence of the tagged ubiquitin protein is reduced by the quencher conjugated to the tIVR. Since free ubiquitin proteins disrupt the binding of the fluorophore-tagged ubiquitin proteins and tIVR tagged with the quencher, increasing levels of free ubiquitin proteins results in greater fluorescence intensity. This change in fluorescence depends not only on FRET, but also by the quenching induced by the interaction between tIVR and fluorophore-tagged ubiquitin proteins. The curve generated from this experiment can be used as a calibration standard in assays to measure free ubiquitin proteins in complex biological samples.

Figure 20:
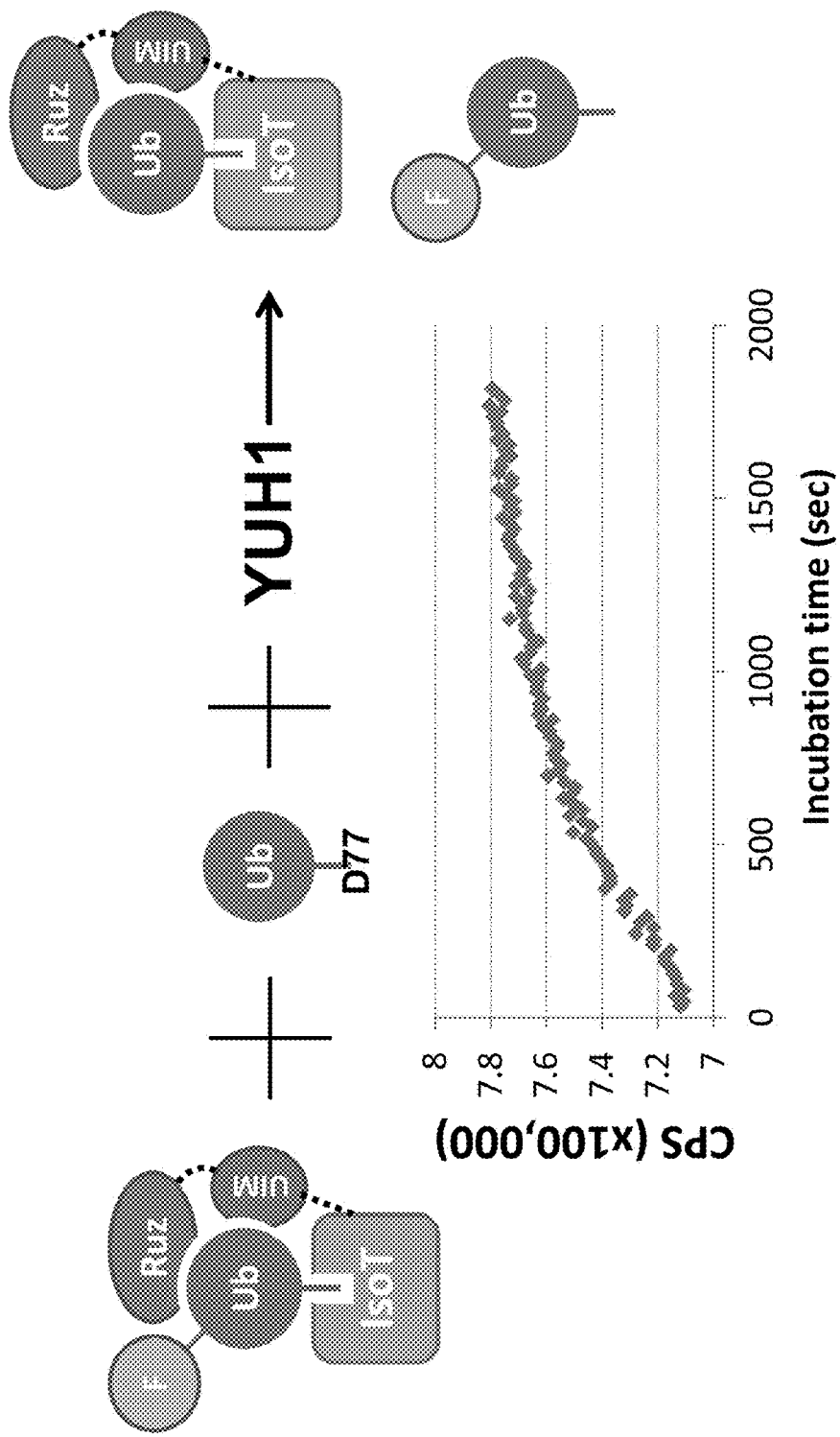

FIG. 20 provides a graph showing that deubiquitinase enzyme activity can be measured in a real-time assay. Release of ubiquitin by YUH1, a deubiquitinase enzyme, was measured as a fluorescence intensity change. Fluorescence intensity of a mixture containing YUH1, 500 nM of ubiquitin-D77 (i.e., ubiquitin conjugated to aspartic acid) as substrate, 10 nM fluorescence-tagged ubiquitin, and 10 nM tIVR was measured over time.

FIG. 21 provides a graph showing that deubiquitinase activity can be monitored continuously. A real-time deubiquitinase assay using Atto532-tagged ubiquitin proteins and tIVR is graphed. A mimic of polyubiquitinated-protein substrate, was digested with 25 nM Usp2cc or 3 μM OTUB1 with or without UbcH5c in presence of 1 nM Atto532-tagged ubiquitin protein and 1 nM tIVR to detect free ubiquitin released by the deubiquitinases. OTUB1 activity is unregulated by UbcH5c.

Figure 22:
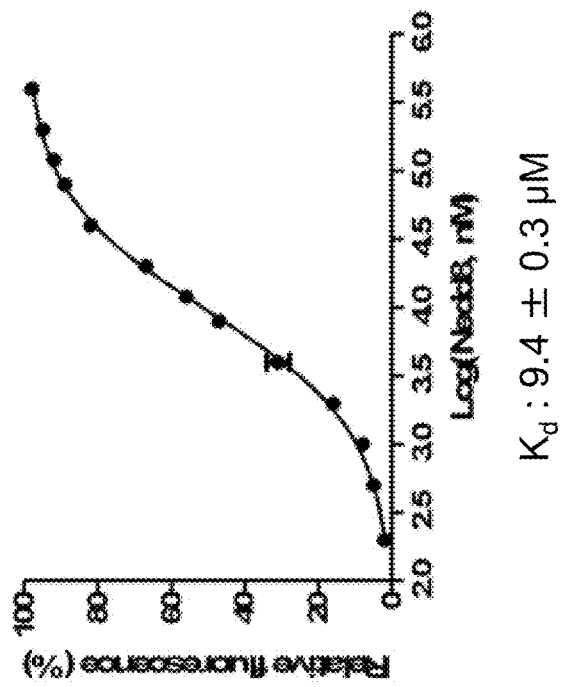

FIG. 22 provides a graph showing that Atto532-tagged tIV L1 Cys binds to free Nedd8 with a $K_d$ of several μM.

Figure 23:

FIG. 23 provides the construction scheme for the universal sensors. A chimeric polypeptide comprising a domain that binds to the hydrophobic patch of ubiquitin protein and a domain that binds the surface around ubiquitin are depicted. A linker connects these domains.

FIG. 24 provides a schematic illustration of the design concept for the chimeric polypeptide universal sensor for free ubiquitin. Ubiquitin is depicted interacting with two binding domains that bind non-overlapping regions of ubiquitin (top). An example chimeric polypeptide comprising two domains connected by two linkers is depicted binding to ubiquitin at the two non-overlapping sites (bottom).

Figure 25:
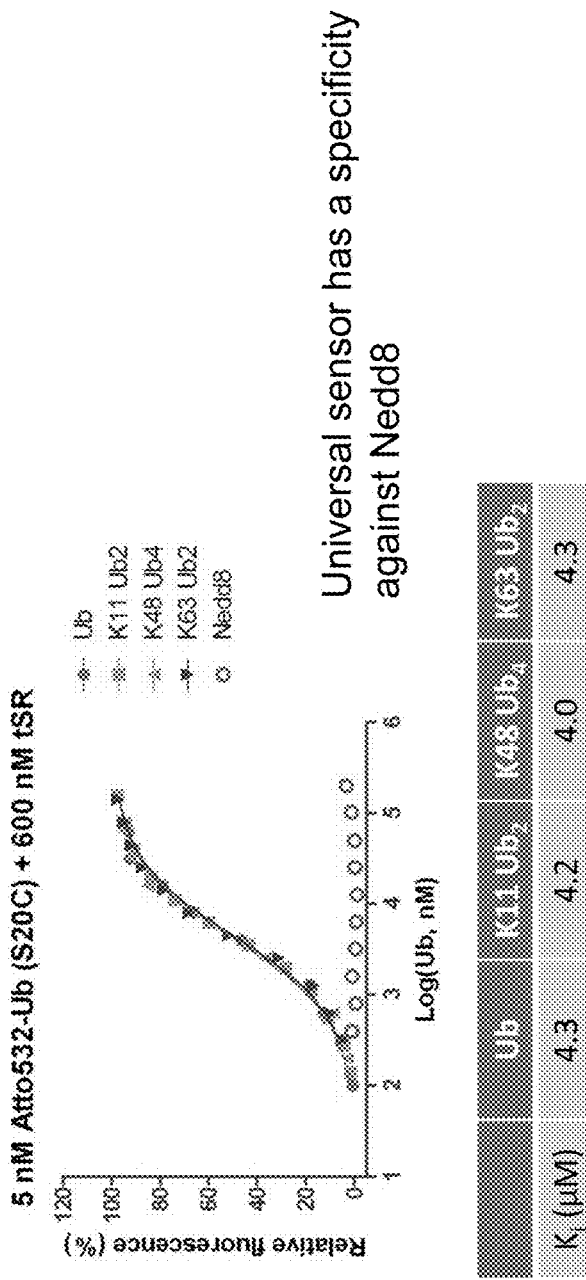

FIG. 25 provides a graph and table showing that the tSR chimeric peptide universal sensor does not discriminate among ubiquitin protein. A competition assay was performed where unconjugated free ubiquitin proteins, different kinds of conjugated free ubiquitin proteins, and Nedd8 were added to mixtures of 5 nM Atto532-tagged ubiquitin protein and 600 nM tSR. The relative fluorescence was measured. While tSR had similar binding affinities for unconjugated ubiquitin proteins and conjugated ubiquitin proteins, tSR displayed specificity against Nedd8 (top). The Ki values for unconjugated ubiquitin proteins and the different kinds of conjugated free ubiquitin proteins are provided in a table (bottom).

Figure 26:
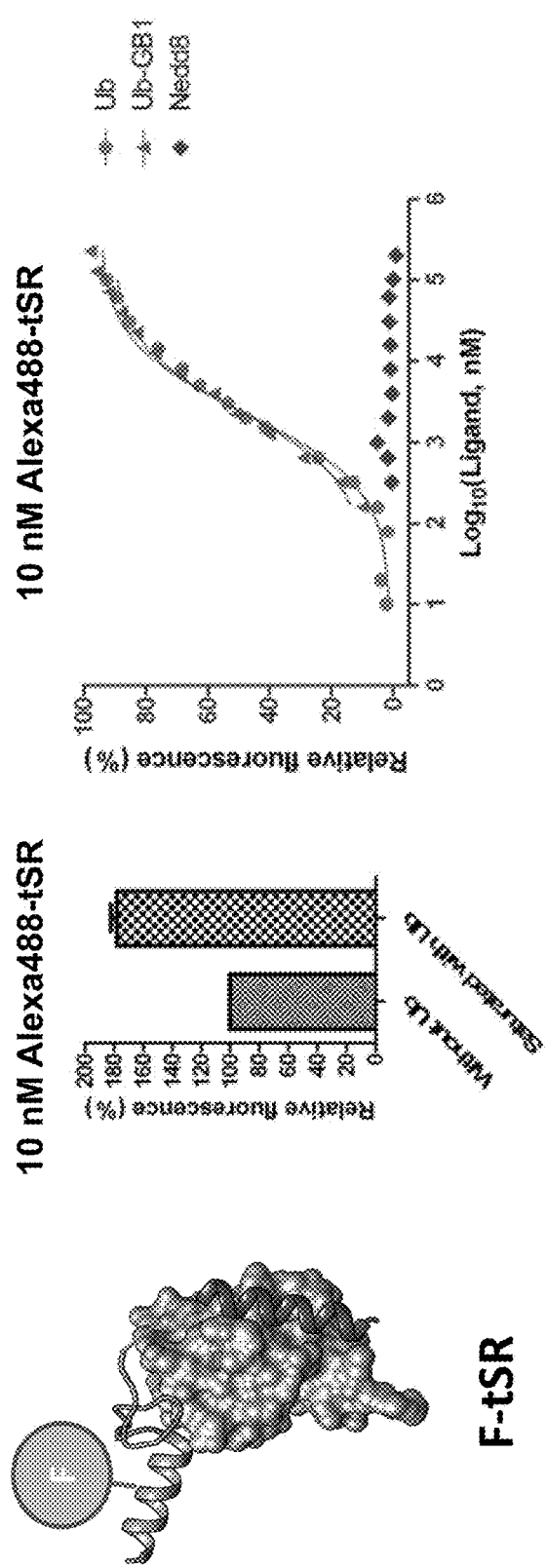

FIG. 26 provides an illustration and graphs demonstrating that tSR can be used for direct titration experiments. An illustration shows fluorophore-tagged tSR is shown binding to ubiquitin (left). The relative fluorescence intensity changes of Alexa488-tagged tSR when ubiquitin is added is shown (middle). The relative fluorescence of 10 nM Alexa488 tSR when different concentrations of unconjugated ubiquitin protein, conjugated ubiquitin protein, or Nedd8 are added (right).

DESCRIPTIONS OF THE SEQUENCES

SEQ ID NO: 1 is the amino acid sequence of the tIVR chimeric polypeptide sensor.

SEQ ID NO: 2 is the amino acid sequence of the tIVR L1 Cys chimeric polypeptide sensor.

SEQ ID NO: 3 is the amino acid sequence of the tIVR (R218C) chimeric polypeptide sensor.

SEQ ID NO: 4 is the amino acid sequence of the tIDR chimeric polypeptide sensor.

SEQ ID NO: 5 is the amino acid sequence of the tIVL1 Cys chimeric polypeptide sensor.

SEQ ID NO: 6 is the amino acid sequence of the tISR chimeric polypeptide sensor.

SEQ ID NO: 7 is the amino acid sequence of the tSR chimeric polypeptide sensor.

SEQ ID NO: 8 is the amino acid sequence of the Iso T$^{ZnF}$ ubiquitin binding domain.

SEQ ID NO: 9 is the amino acid sequence of the Vps27$^{UIM}$ ubiquitin binding domain.

SEQ ID NO: 10 is the amino acid sequence of the Ruz ubiquitin binding domain.

SEQ ID NO: 11 is the amino acid sequence of the Dsk$^{UBA}$ ubiquitin binding domain.

SEQ ID NO: 12 is the amino acid sequence of the S5a$^{UIM}$ ubiquitin binding domain.

SEQ ID NO: 13 is the amino acid sequence of the tIVR linker 1.

SEQ ID NO: 14 is the amino acid sequence of the tIVR linker 2.

SEQ ID NO: 15 is the amino acid sequence of the tIDR linker 1.

SEQ ID NO: 16 is the amino acid sequence of the tIDR linker 2.

SEQ ID NO: 17 is the amino acid sequence of the tIVR linker 1 with a Cys addition.

SEQ ID NO: 18 is the amino acid sequence of the tIV linker 1 with a Cys addition.

SEQ ID NO: 19 is the amino acid sequence of the tISR linker 1.

SEQ ID NO: 20 is the amino acid sequence of the tISR linker 2.

SEQ ID NO: 21 is the amino acid sequence of the tSR linker 1.

SEQ ID NO: 22 is the amino acid sequence of human ubiquitin protein.

SEQ ID NO: 23 is the amino acid sequence of the human Nedd8 protein.

SEQ ID NO: 24 is the amino acid sequence of the human SUMO1 protein.

SEQ ID NO: 25 is the amino acid sequence of the human SUMO2 protein.

SEQ ID NO: 26 is the amino acid sequence of the human SUMO3 protein.

SEQ ID NO: 27 is the amino acid sequence of ubiquitin (S20C).

SEQ ID NO: 28 is the amino acid sequence of a long tIVR linker 1.

SEQ ID NO: 29 is the amino acid sequence of OTUB1.

SEQ ID NO: 30 is the amino acid sequence of a short tIVR linker 1.

SEQ ID NO: 31 is the amino acid sequence of the IsoT$^{ZnF}$ (S227C) ubiquitin binding domain.

SEQ ID NO: 32 is the amino acid sequence of Ub-GB1.

SEQ ID NO: 33 is the amino acid sequence of UBCH5C.

SEQ ID NO: 34 is the amino acid sequence of the DUIM ubiquitin binding domain.

SEQ ID NO: 35 is the amino acid sequence of the MIU ubiquitin binding domain.

SEQ ID NO: 36 is the amino acid sequence of the CUE ubiquitin binding domain.

SEQ ID NO: 37 is the amino acid sequence of the GAT ubiquitin binding domain.

SEQ ID NO: 38 is the amino acid sequence of the Jab1/MPN ubiquitin binding domain.

SEQ ID NO: 39 is the amino acid sequence of the NZF ubiquitin binding domain.

SEQ ID NO: 40 is the amino acid sequence of the UBZ ubiquitin binding domain.

SEQ ID NO: 41 is the amino acid sequence of the UBS ubiquitin binding domain.

SEQ ID NO: 42 is the amino acid sequence of the UBM ubiquitin binding domain.

DETAILED DESCRIPTION OF THE INVENTION

The present invention provides new chimeric polypeptides that selectively bind to ubiquitin proteins or ubiquitin-like proteins, and new methods to detect amounts of ubiquitin proteins or ubiquitin-like proteins. These methods can be tailored to detect a distinct target ubiquitin proteins or ubiquitin-like proteins, including total ubiquitin proteins, free ubiquitin proteins, conjugated ubiquitin proteins, total ubiquitin-like proteins, free ubiquitin-like proteins, or conjugated ubiquitin proteins. The methods also include a novel deubiquitinase assay. Further, the present invention can be utilized to screen for agents that alter ubiquitin protein or ubiquitin-like protein conjugation.

In certain embodiments, the chimeric polypeptides (also may also be referred to as "sensors") include two or more binding domains that bind to a ubiquitin protein or a ubiquitin-like protein. The binding domains are connected by one or more linker(s). In particular embodiments, the binding domains of a chimeric polypeptide bind to non-overlapping regions within a single ubiquitin protein or ubiquitin-like polypeptide, and the binding domains can bind the ubiquitin protein or ubiquitin-like protein simultaneously. This results in the chimer polypeptide having greater binding affinity and specificity than any of the binding domains alone.

In related embodiments, the present invention provides new methods to detect and measure amounts of free ubiquitin proteins, free ubiquitin-like proteins, conjugated ubiquitin proteins, or conjugated ubiquitin-like proteins. In various embodiments, the chimeric polypeptides of the present invention can be used in direct titration assays, competitive binding assays, fluorescence resonance energy transfer (FRET), and deubiquitination assays to determine an amount of a free ubiquitin protein, a free ubiquitin-like protein, a conjugated ubiquitin protein, or a conjugated ubiquitin-like protein. The methods and assays of the present invention may also be used to determine the total amount of a ubiquitin protein or a ubiquitin-like protein, as well as the percentage the total ubiquitin protein that is free or conjugated. The present invention allows for the detection of free ubiquitin proteins, free ubiquitin-like proteins, conjugated ubiquitin proteins, or conjugated ubiquitin-like proteins by measurement of detectable signals, by means including fluorescence intensity or fluorescence anisotropy. The chimeric polypeptides can be used to detect ubiquitin protein or ubiquitin-like protein in vitro, as well in biological samples, including extracts from cell cultures or tissues.

The present invention has several advantages. Despite the importance and abundance of the ubiquitin system, few methods exist for detecting an amount of free ubiquitin protein or ubiquitin-like protein or determining the amount of a total ubiquitin protein or ubiquitin-like protein that is in free or conjugated. Methods that do exist can be inaccessible to many laboratories. In one embodiment, the present invention provides novel methods of detecting free ubiquitin proteins or free ubiquitin-like proteins, and it does so without the use of high performance liquid chromatography, mass spectrometry, heavy-isotope standards, antibodies, film, or gel electrophoresis. Furthermore, only one other method has been described that is able to specifically measure ubiquitin that has an intact free C-terminus, but unlike the present invention, that method is unsuitable for complex biological samples such as cell or tissue lysates, requires use of radioactive ATP, and is not amenable to high-throughput assays. The present invention provides novel chimeric polypeptides that bind to ubiquitin proteins or ubiquitin-like proteins with high affinity and specificity. These chimeric polypeptides can be used to measure ubiquitin protein or ubiquitin-like protein in vitro, and can be used with complex cell or tissue extracts. The methods of the present invention can also be used in assays to identify or evaluate proteasome inhibitors, deubiquitinating enzymes (deubiquitinases, or "DUBs"), and DUB inhibitors, or other ubiquitin pathway modulators (e.g., agonists or inhibitors) for their effects on the amount of free ubiquitin. The present invention also can be used in quantitative, real-time assays of DUB activities that, unlike existing assay formats, can use any form of conjugated ubiquitin as the substrate.

I. Ubiquitin Sensors

The present invention provides chimeric polypeptides, i.e., chimeric polypeptide sensors, that comprise two or more sequences that bind to a ubiquitin protein or a ubiquitin-like protein, and methods comprising the use of the chimeric polypeptide sensors to detect an amount of a ubiquitin protein or a ubiquitin-like protein in a sample or mixture. In one aspect, the present invention comprises a chimeric polypeptide sensor comprising two or more polypeptide sequences that bind a ubiquitin protein or a ubiquitin-like protein wherein the sequences bind non-overlapping regions of the ubiquitin protein or ubiquitin like protein; and one or more linker(s), wherein the linker(s) connect the two or more sequences.

In certain embodiments, the chimeric polypeptide sensors bind to the ubiquitin proteins or the ubiquitin-like proteins in both their "free" state, (i.e., not conjugated to a non-ubiquitin protein) and in their "conjugated" state (i.e., conjugated to a non-ubiquitin protein), e.g., with approximately the same or similar affinity. As used herein, "free" ubiquitin proteins and "free" ubiquitin-like proteins include ubiquitin protein monomers and ubiquitin-like protein monomers, as well as "polyubiquitins" and "polyubiquitin-like proteins," which comprise or consist of two or more ubiquitins or two or more ubiquitin-like proteins, respectively. "Total" ubiquitin protein refers to combined free ubiquitin protein and conjugated ubiquitin protein. "Total" ubiquitin-like protein refers to combined free ubiquitin-like protein and conjugated ubiquitin-like protein. In some embodiments, the chimeric polypeptide sensors preferentially bind to a free ubiquitin protein or a free ubiquitin-like protein as compared to the corresponding conjugated ubiquitin protein or conjugated ubiquitin-like protein (i.e., the same protein conjugated to a non-ubiquitin or non-ubiquitin-like protein), e.g., with an affinity at least 1.5-fold greater, 2.0-fold greater, 3.0-fold greater, at least 4.0-fold greater, at least 5.0-fold greater, at least 10-fold greater, at least 20-fold greater, at least 30-fold greater, at least 50-fold greater, or at least 100-fold greater.

In some embodiments, the chimeric polypeptide sensor preferentially binds to the target ubiquitin protein or the target ubiquitin-like protein as compared to another ubiquitin protein or ubiquitin-like protein. In certain embodiments, a chimeric polypeptide has an affinity for a target protein at least 1.5-fold greater, 2.0-fold greater, 3.0-fold greater, at least 4.0-fold greater, at least 5.0-fold greater, at least 10-fold greater, at least 20-fold greater, at least 30-fold greater, at least 50-fold greater, or at least 100-fold greater than its affinity for another ubiquitin or ubiquitin-like protein. In some embodiments, the chimeric polypeptide sensor preferentially binds to a ubiquitin protein as compared to a ubiquitin-like protein. In some embodiments, the chimeric polypeptide sensor preferentially binds to total ubiquitin protein as compared to total ubiquitin-like protein. In other embodiments, the chimeric polypeptide sensor preferentially binds to a ubiquitin-like protein as compared to a ubiquitin protein. In some embodiments, the chimeric polypeptide sensor preferentially binds to total ubiquitin-like protein as compared to total ubiquitin protein.

In some embodiments, the chimeric polypeptide sensor preferentially binds to a free ubiquitin as compared to the conjugated ubiquitin. In some embodiments, the chimeric polypeptide sensor preferentially binds to a free ubiquitin-like protein as compared to the conjugated ubiquitin-like protein. In some embodiments, the chimeric polypeptide sensor preferentially binds to free ubiquitin-like protein compared to conjugated ubiquitin-like proteins and ubiquitin proteins. It will be understood by those in the art that preferential binding to a particular ubiquitin protein or a particular ubiquitin-like protein means preferential binding compared to other proteins that are not the particular ubiquitin protein or the particular ubiquitin-like protein.

The term "polypeptide" as used herein interchangeably with the term "protein" describes linear molecular chains of amino acids, including single chain proteins or their fragments, containing multiple amino acids. Furthermore, peptidomimetics of such proteins/polypeptides where amino acid(s) and/or peptide bond(s) have been replaced by functional analogues are also encompassed by the invention. Such functional analogues include all known amino acids other than the 20 gene-encoded amino acids, such as selenocysteine. The terms "polypeptide" and "protein" also refer to naturally modified polypeptides/proteins where the modification is effected e.g. by glycosylation, acetylation, phosphorylation and similar modifications which are well known in the art. The terms "terminal" and "terminus" are well understood in the art and are used here interchangeably.

The recitations "sequence identity", "percent identity", "percent homology", or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using an NWSgapdna.CMP matrix and a gap weight of 40, 50, 60, 70, or 80 and a length weight of 1, 2, 3, 4, 5, or 6. Another exemplary set of parameters includes a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

The peptide sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (Nucleic Acids Res. 25:3389-3402, 1997). When utilizing BLAST and Gapped BLAST programs, the default parameters of the respective programs (e.g., XBLAST and NBLAST) can be used.

In certain embodiments, the invention comprises a chimeric polypeptide sensor that binds to a free ubiquitin protein with high affinity and selectivity compared to total ubiquitin protein and compared to ubiquitin-like proteins. In some embodiments, the chimeric polypeptide comprises more than one ubiquitin binding domain, e.g., two or three ubiquitin binding domains, wherein the binding domains bind to non-overlapping regions of the ubiquitin protein. In some embodiments, the chimeric polypeptide sensor binds to the ubiquitin protein with higher affinity and specificity than a polypeptide comprising a single binding domain.

In certain embodiments, the invention comprises a chimeric polypeptide sensor that binds to free ubiquitin-like protein with high affinity and specificity. In some embodiments, the chimeric peptide sensor comprises more than one ubiquitin-like protein binding domain, e.g., two or three ubiquitin-like protein binding domains, wherein the binding domains bind to non-overlapping regions of the ubiquitin-like protein. In some embodiments, the chimeric polypeptide sensor binds to the ubiquitin-like protein with higher affinity and specificity than a polypeptide comprising a single binding domain.

In particular embodiments, the ubiquitin protein binding domains and ubiquitin-like protein binding domains are polypeptide sequences that bind to the ubiquitin protein or the ubiquitin-like protein, including any of those described herein.

In particular embodiments, a chimeric polypeptide of the present invention comprises or consists of two polypeptide sequences that bind non-overlapping regions of the same ubiquitin protein or ubiquitin-like protein and one or more linker moiety. In one embodiment, the chimeric polypeptide includes one linker moiety that connects the two polypeptide sequences.

In particular embodiments, a chimeric polypeptide of the present invention comprises or consists of three polypeptide sequences that bind non-overlapping regions of the same ubiquitin protein or ubiquitin-like protein and one, two or more linker moieties. In one embodiment, the chimeric polypeptide includes one linker moiety that connects all three polypeptide sequences. For example, the linker may be a linker capable of binding to three polypeptide sequences. In one embodiment, the chimeric polypeptide includes two linker moieties, each of which connects two of the polypeptide sequences.

In some embodiments, the invention comprises a chimeric polypeptide that binds to a ubiquitin protein or a ubiquitin-like protein, comprising in the following order: a first polypeptide sequence that binds to a first region of the ubiquitin protein or the ubiquitin-like protein; a first linker that connects the first polypeptide sequence to a second polypeptide sequence that binds to a second region of the ubiquitin protein or the ubiquitin-like protein, a second linker that connects the second polypeptide sequence to a third polypeptide sequence that binds to a third region of the ubiquitin protein or the ubiquitin-like protein, whereas the first, second and third regions of the ubiquitin protein or the ubiquitin-like protein bound by the first, second, and third polypeptide sequences are non-overlapping. In some embodiments of the invention, the chimeric polypeptide sensor comprises more than three ubiquitin protein or ubiquitin-like protein binding domains that bind to non-overlapping regions of the ubiquitin protein or the ubiquitin-like protein.

Nucleotide and amino acid sequences of ubiquitin proteins are known in the art. In certain embodiments, a ubiquitin protein according to the invention has at least 80%, at least 85%, at least 90%, at least 95%, at least 98%, or at least 99% identity to a known ubiquitin protein, such as the human ubiquitin protein. In some embodiments, the ubiquitin protein is the human ubiquitin protein. In other embodiments, the ubiquitin according to the invention includes naturally occurring or engineered variants of ubiquitin. The amino acid sequence of the human ubiquitin protein is provided in SEQ ID NO: 22.

Ubiquitin proteins also include naturally occurring alleles and human engineered variants of a known ubiquitin protein. In some embodiments, a ubiquitin protein comprises the sequence of a known ubiquitin protein, but with one or more amino acid deletion, addition, or substitution, for example, for the purposes of generating a site on the ubiquitin protein to conjugate a detectable label. In some embodiments, the ubiquitin protein comprises a substitution of the serine at amino acid position 20 with a cysteine (S20C) to allow for covalent attachment of a detectable label to the ubiquitin protein SEQ ID NO 27].

In certain embodiments, a ubiquitin binding domain, according to the invention, has at least 75, least 80%, at least 85%, at least 90%, at least 95%, at least 98%, at least 99% identity, or 100% amino acid sequence identity to a known ubiquitin binding domain. Ubiquitin binding domains refer to a diverse family of dissimilar protein modules that bind ubiquitin. Many ubiquitin binding domains have been described in the art, and they include at least 19 different binding domains. These ubiquitin binding domains include, but are not limited to, the UBA (Ubiquitin Associated domain), UIM (Ubiquitin Interacting Motif), MIU (Motif Interacting with Ubiquitin; SEQ ID NO: 35) domain, DUIM (double-sided ubiquitin-interacting motif; SEQ ID NO: 34), CUE (coupling of ubiquitin conjugation to ER degradation; SEQ ID NO: 36) domain, NZF (Np14 zinc finger; SEQ ID NO: 39), A20 ZnF (zinc finger), Ruz (RABEX-5 zinc finger), UBP ZnF or BUZ (ubiquitin-specific processing protease zinc finger), UBZ (ubiquitin-binding zinc finger; SEQ ID NO: 40), UEV (ubiquitin-conjugating enzyme E2 variant), PFU (PLAA family ubiquitin binding), GLUE (GRAM-like ubiquitinbinding in EAP45), GAT (Golgi-localized, Gamma-ear-containing, Arf-binding; SEQ ID NO: 37), Jab1/MPN (Jun kinase activation domain binding/ Mpr1p and Pad1p N-termini; SEQ ID NO: 38), WD40 βPrps (WD40 β-propellers), UBM (Ubiquitin binding motif; SEQ ID NO: 42), UBS (Ubiquitin binding surface; SEQ ID NO: 41), UBR (ubiquitin binding region), and Ubc (ubiquitin-conjugating enzyme). UBDs are structural motifs, many as short as 20-40 amino acids long, with low sequence conservation, that are found in all eukaryotes. These binding domains bind to specific regions of ubiquitin.

In some embodiments of the present invention, the chimeric polypeptide sensor comprises a ubiquitin binding domain that binds to the ubiquitin C-terminus. In some embodiments, the chimeric polypeptide sensor comprises a ubiquitin binding domain that binds to the surface hydrophobic patch of a ubiquitin protein. In other embodiments, the chimeric polypeptide comprises a ubiquitin binding domain that binds to the ubiquitin protein at the surface near Asp58.

The ubiquitin C-terminus is known in the art as a site of attachment where a ubiquitin protein can be conjugated to a non-ubiquitin protein; thus, this C-terminus is exposed in free ubiquitin. When a ubiquitin protein is conjugated to a non-ubiquitin protein at the ubiquitin C terminus, the non-ubiquitin protein is referred to in the art as being "ubiquitinated". Without wishing to be bound to any particular theory, it is believed that chimeric polypeptide sensors that include a sequence that binds to a ubiquitin C-terminal domain have greater binding affinity for a free ubiquitin protein (including free polyubiquitin) than for a conjugated ubiquitin protein. Known ubiquitin binding domains that can bind ubiquitin protein at the ubiquitin C-terminus include ZnF UBP and Ubc. Accordingly, in certain embodiments, chimeric polypeptide sensors of the present invention comprise a sequence that binds to a ubiquitin C-terminal domain, and these sensors preferentially bind to a free ubiquitin protein as compared to the same ubiquitin protein when it is conjugated. In certain embodiments, these chimeric polypeptide sensors bind to the free ubiquitin protein with at least 1.5-fold, two-fold, three-fold, four-fold, five-fold or ten-fold greater affinity than they bind to the conjugated ubiquitin protein.

The surface near the ubiquitin Asp58 amino acid residue is a region of ubiquitin protein that can interact with proteins containing certain ubiquitin binding domains. Known ubiquitin binding domains that can bind ubiquitin protein at the surface near the ubiquitin Asp58 include Ruz.

The ubiquitin hydrophobic patch is a region of ubiquitin that can interact with proteins containing certain ubiquitin binding domains. The ubiquitin hydrophobic patch is located on the ubiquitin protein near the ubiquitin Ile44 residue. Typically, ubiquitin binding domains that comprise an alpha helix can interact with mono-ubiquitin proteins at the ubiquitin hydrophobic patch. Known ubiquitin binding domains that can bind ubiquitin protein at the ubiquitin hydrophobic patch include UBA, UIM, DUIM, MIU, CUE, GAT, Jab1/MPN, NZF, UBZ, UBS, and UBM.

In some embodiments, the invention comprises a chimeric polypeptide comprising two or more polypeptide sequences that bind a ubiquitin protein or a ubiquitin-like protein, wherein the sequences bind non-overlapping regions of the ubiquitin protein or ubiquitin-like protein, and one or more linker(s), wherein the linker(s) connects the two or more polypeptide sequences. In some embodiments, the invention comprises a chimeric polypeptide wherein the sequences comprise a sequence that binds to the ubiquitin C terminus and a sequence that binds to the ubiquitin hydrophobic patch. In some embodiments, the invention comprises a chimeric polypeptide wherein the sequences comprise a sequence that binds to the ubiquitin C terminus and a sequence that binds the surface around Asp58 of ubiquitin. In some embodiments, the invention comprises a chimeric polypeptide, wherein the sequences comprise a sequence that binds to the ubiquitin hydrophobic patch and a sequence that binds to surface around Asp58 of ubiquitin. In some embodiments, the invention comprises a chimeric polypeptide comprising a sequence that binds to the ubiquitin C terminus, a sequence that binds to the ubiquitin hydrophobic patch, and a sequence that binds to the surface around Asp58 of ubiquitin.

In some embodiments of the invention, a chimeric polypeptide comprising a ubiquitin binding domain that binds to a ubiquitin protein at a particular binding site will have similar binding affinities and specificities (e.g., with respect to targets of ubiquitin protein) as another chimeric polypeptide sensor comprising a different ubiquitin binding region that binds to the same binding site of the ubiquitin protein. Thus, in certain embodiments of the invention, any of the specific ubiquitin binding domains that bind to sites on the ubiquitin protein are interchangeable with other ubiquitin binding domains from other proteins that contain the same kind of ubiquitin binding domain (e.g., binds to the same site on the ubiquitin protein), and ubiquitin binding domains that bind to the same sites on the ubiquitin protein may be swapped to achieve a chimeric polypeptide sensor with similar binding affinity and selectivity to a target ubiquitin protein. Further, in certain embodiments of the invention, the specific ubiquitin binding domains that bind to sites on the ubiquitin protein are interchangeable with other ubiquitin binding domains that bind to ubiquitin at the same sites on the ubiquitin protein, and may be interchanged to achieve a chimeric polypeptide sensor with similar binding affinity and selectivity to a target ubiquitin protein. The same concept holds true for chimeric polypeptide sensors that bind to a ubiquitin-like protein. Thus, the present invention is not restricted to specific polypeptide domains that bind to a ubiquitin protein or a ubiquitin-like protein on multiple sites, but rather, the present invention encompasses chimeric polypeptide sensors that comprise any ubiquitin binding domains that bind the ubiquitin or ubiquitin-like protein on the same sites.

In some embodiments in the present invention, the chimeric polypeptide comprises an order, from N-terminal to C-terminal, of an arrangement of non-overlapping ubiquitin protein binding domains or ubiquitin-like protein binding domains. In some embodiments, the order of the binding domains, from N-terminal to C-terminal is interchangeable. Thus, in some embodiments, a chimeric polypeptide comprising an order of a first, a second, and a third binding domain will have similar binding affinities and specificities for target ubiquitin proteins or ubiquitin-like proteins as a chimeric polypeptide sensor comprising an order of the third, the second, and the first binding domain, and will have similar binding affinities and specificities as a chimeric polypeptide sensor comprising an order of the second, the third, and the first binding domain, and will have the similar binding affinities as a chimeric polypeptide sensor comprising an order of the first, the third, and the second binding domain. Thus, in some embodiments, properties of the chimeric polypeptide sensor do not depend on the order the ubiquitin or ubiquitin-like protein binding domains are arranged. Further, in some embodiments of the invention, the properties of a chimeric polypeptide sensor that binds to a ubiquitin protein or a ubiquitin-like protein with high affinity comprising two or more ubiquitin protein or ubiquitin-like protein binding domains does not depend on the order the ubiquitin protein or ubiquitin-like protein binding domains are arranged.

In certain embodiments of the invention, a linker moiety (or "linker") is a moiety that connects two ubiquitin protein or ubiquitin-like protein binding domains. In some embodiments, the linker must be an appropriate length to allow the binding domains to simultaneously bind to the same ubiquitin protein or ubiquitin-like protein. In certain embodiments, a linker moiety is a chemical moiety or a polypeptide. A variety of linker moieties are known and available in the art. In certain embodiments, linkers comprise at least one amino acid. In some embodiments, linkers comprise more than two amino acids. In some embodiments, linkers comprise more than three amino acids, more than four amino acids, more than five amino acids, more that ten amino acids, more than 20 amino acids, or more than 30 amino acids. In some embodiments, linkers comprise between two and 30 amino acids. In some embodiments, linkers comprise between three and 30 amino acids, between three and 15 amino acids, between three and twelve amino acids, between four and twelve amino acids, between five and twelve amino acids, between five and ten amino acids, between five and 15 amino acids, between four and 30 amino acids, between five and 30 amino acids, between ten and 30 amino acids, between 20 and 30 amino acids, or between 10 and 50 amino acids. In certain embodiments, a linker includes less than or equal to 100, 50, 40, 30, 20, 15, twelve, ten, nine, eight, seven, six, five, four, three, or two amino acid residues. In some embodiments, linkers are comprised of or consist of one or more amino acid(s) selected from the group of glycine, serine, or alanine residues. In some embodiments, linkers further comprise a cysteine residue. In some embodiments, linkers are comprised of or consist of one or more amino acid(s) selected from the group of glycine, serine, alanine and cysteine residues. In some embodiments, the cysteine residue is conjugated to a detectable label. In particular embodiments, a linker moiety comprises or consists of any of the amino acid sequences set forth in SEQ ID NOs: 13, 15, 16, 17, 19, and 28. Examples of illustrative linkers and polypeptide sensors of the present invention are also provided in the accompanying Examples. In some embodiments, the binding affinity of the chimeric polypeptide sensor to a target ubiquitin protein or ubiquitin-like protein is influenced by length of the linker(s). One of skill in the art will appreciate that a linker connecting two or more ubiquitin binding domains should be of sufficient length and flexibility to allow the ubiquitin binding domains to contact and bind the regions of the ubiquitin protein that they bind, while these ubiquitin binding domains are connected via the linker. Accordingly, the length of the linker may be determined based, in part, on knowledge of the regions of the ubiquitin protein (or ubiquitin-like protein) bound by the two binding domains connected via the linker.

In some embodiments, the invention comprises a chimeric polypeptide sensor that comprises or consists of two or more ubiquitin or ubiquitin-like protein binding domains and at least one linker.

In some embodiments, the invention comprises a chimeric polypeptide wherein the sequences comprise the ZnF UBP binding domain from Isopeptidase T. In some embodiments, the invention comprises a chimeric polypeptide wherein the sequences comprise the Ruz domain from Rabex-5. In some embodiments, the invention comprises a chimeric polypeptide wherein the sequences comprise the ubiquitin interacting motif (UIM) from Vps27. In some embodiments, the invention comprises a chimeric polypeptide wherein the sequences comprise the ubiquitin associated (UBA) domain from Dsk2.

In some embodiments, the invention comprises a chimeric polypeptide sensor, wherein the sequences comprise or consist of the ZnF UBP binding domain from Isopeptidase T and the Ruz domain from Rabex-5. In some embodiments, the invention comprises a chimeric polypeptide sensor, wherein the sequences comprise or consist of the ZnF UBP binding domain from Isopeptidase T and the ubiquitin interacting motif from Vps27. In some embodiments, the invention comprises a chimeric polypeptide, wherein the sequences comprise or consist of the Ruz domain from Rabex-5 and the ubiquitin interacting motif from Vps27. In some embodiments, the invention comprises a chimeric polypeptide sensor, wherein the sequences comprise or consist of the ZnF UBP binding domain from Isopeptidase T, the Ruz domain from Rabex-5, and the ubiquitin interacting motif from Vps27.

In some embodiments, the invention comprises a chimeric polypeptide sensor that comprises or consists of two or more ubiquitin or ubiquitin-like protein binding domains and at least one linker, wherein the chimeric polypeptide sensor does not comprise a binding domain that binds the ubiquitin protein or ubiquitin-like protein at its C-terminus or C-terminal domain. In certain embodiments, such a chimeric polypeptide sensor binds with approximately the same affinity and/or specificity to a free ubiquitin protein or free ubiquitin-like protein as compared to the same ubiquitin protein or ubiquitin-like protein when conjugated.

In some embodiments of the invention, a ZnF UBP binding domain from Isopeptidase T according to the invention has at least 80%, at least 85%, at least 90%, at least 95%, at least 98%, at least 99%, or 100% identity to a known zinc finger binding domain from Isopeptidase T protein, such as the from the human Isopeptidase T protein. In some embodiments of the invention, a zinc finger binding domain from Isopeptidase T has at least 80%, at least 85%, at least 90%, at least 95%, at least 98%, at least 99%, or 100% identity to SEQ ID NO: 8.

In some embodiments, a Ruz domain from Rabex-5, according to the invention has at least 80%, at least 85%, least 90%, at least 95%, at least 98%, at least 99%, or 100% identity to a known Ruz domain from Rabex-5, such as from the human Rabex-5 protein. In some embodiments of the invention, a Ruz domain from Rabex-5 has at least 80%, at least 85%, at least 90%, at least 95%, at least 98%, at least 99%, or 100% identity to SEQ ID NO:10.

In some embodiments, a ubiquitin interacting motif from Vps27 according to the invention has at least 80%, at least 85%, at least 90%, at least 95%, at least 98%, at least 99%, or 100% identity to a known ubiquitin interacting motif from Vps27, such as from a yeast Vps27 protein. In some embodiments of the invention, a ubiquitin interacting motif from Vps2 has at least 80%, at least 85%, at least 90%, at least 95%, at least 98%, at least 99%, or 100% identity to SEQ ID NO: 9.

In some embodiments, a ubiquitin associated domain from Dsk2 according to the invention has at least 80%, at least 85%, at least 90%, at least 95%, at least 98%, at least 99%, or 100% identity to a known ubiquitin associated domain from Dsk2, such as a yeast Dsk2 protein. In some embodiments of the invention, ubiquitin associated domain from Dsk2 has at least 80%, at least 85%, at least 90%, at least 95%, at least 98%, at least 99%, or 100% identity to SEQ ID NO: 11.

In some embodiments, ubiquitin interacting motif from the S5a subunit of the proteasome according to the invention has at least 80%, at least 85%, at least 90%, at least 95%, at least 98%, at least 99%, or 100% identity to a known ubiquitin interacting motif from the S5a subunit of the proteasome, such as the human S5a protein. In some embodiments of the invention, a ubiquitin interacting motif from the S5a subunit of the proteasome has at least 80%, at least 85%, at least 90%, at least 95%, at least 98%, at least 99% or 100% identity to SEQ ID NO: 12.

In some embodiments, the invention comprises a chimeric polypeptide sensor comprising the ZnF UBP binding domain from Isopeptidase T, the Ruz domain from Rabex-5, the ubiquitin interacting motif from Vps27, and a first polypeptide linker and a second polypeptide linker. In some embodiments, the chimeric polypeptide sensor comprises the sequence of SEQ ID NO: 1 and is termed tIVR. In some embodiments, tIVR has a high binding affinity and specificity for free ubiquitin, as compared to conjugated ubiquitin and compared to ubiquitin-like proteins. In some embodiments, tIVR is tagged with a detectable label. In some embodiments, tIVR is tagged with a fluorophore. In some embodiments, the tIVR is tagged with a fluorophore at R218C (SEQ ID NO:3). In some embodiments, the tIVR is tagged with a fluorophore at the first polypeptide linker. In some embodiments, the tIVR is tagged with a fluorophore at the first polypeptide linker and comprises the sequence SEQ IS NO: 2. In some embodiments, the tIVR has at least 80%, at least 85%, at least 90%, at least 95%, at least 98%, at least 99%, or 100% identity to SEQ ID NO: 1.

In some embodiments, the invention comprises a chimeric polypeptide sensor comprising the ZnF UBP binding domain from Isopeptidase T and the ubiquitin associated domain from Dsk2. In some embodiments, the chimeric polypeptide sensor comprises the Ruz domain from Rabex-5 and the ubiquitin associated domain from Dsk2. In some embodiments, the chimeric polypeptide sensor comprises the ZnF UBP binding domain from Isopeptidase T, the Ruz domain from Rabex-5, and the ubiquitin associated domain from Dsk2. In some embodiments, the chimeric polypeptide sensor comprises the sequence of SEQ ID NO: 4. and is termed tIDR. In some embodiments, tIDR has a high binding affinity and specificity for free ubiquitin protein, as compared to conjugated ubiquitin protein and compared to ubiquitin-like protein. In some embodiments, tIDR is tagged with a detectable label. In some embodiments, tIDR is tagged with a fluorophore. In some embodiments, the tIDR has at least 80%, at least 85%, at least 90%, at least 95%, at least 98%, at least 99%, or 100% identity to SEQ ID NO: 4.

In some embodiments, the invention comprises a chimeric polypeptide sensor comprising the ZnF UBP binding domain from Isopeptidase T, the Ruz domain from Rabex-5, the ubiquitin interacting motif from S5a, and a first polypeptide linker and a second polypeptide linker. In some embodiments, the chimeric polypeptide sensor comprises the sequence of SEQ ID NO:6 and is termed tISR. In some embodiments, tISR has a high binding affinity and specificity for free ubiquitin, as compared to conjugated ubiquitin and compared to ubiquitin-like proteins. In some embodiments, tISR is tagged with a detectable label. In some embodiments, tISR is tagged with a fluorophore. In some embodiments, the tISR is tagged with a fluorophore on a cysteine on linker 2. In some embodiments, the tISR is tagged with a fluorophore at the second polypeptide linker and comprises the sequence SEQ ID NO: 6. In some embodiments, the tISR has at least 80%, at least 85%, at least 90%, at least 95%, at least 98%, at least 99%, or 100% identity to SEQ ID NO: 6.

In some embodiments, the invention comprises a chimeric polypeptide sensor comprising the Ruz domain from Rabex-5 and the ubiquitin interacting motif from the S5a subunit of the proteasome. In some embodiments, the chimeric polypeptide sensor comprises the sequence of SEQ ID NO: 7. wherein the chimeric polypeptide sensor is termed tSR. In some embodiments, the tSR has a high binding affinity and specificity for total ubiquitin protein, compared to ubiquitin-like proteins. In some embodiments, the tSR has similar binding affinities to conjugated ubiquitin protein and free ubiquitin protein. In some embodiments, tSR is tagged with a detectable label. In some embodiments, tSR is tagged with a fluorophore. In some embodiments, the tSR has at least 80%, at least 85%, at least 90%, at least 95%, at least 98%, at least 99%, or 100% identity to SEQ ID NO: 7.

In some embodiments, the invention comprises a chimeric polypeptide wherein the sequences bind to non-overlapping regions of a ubiquitin-like protein. In some embodiments, the invention comprises a chimeric polypeptide wherein the sequences bind to non-overlapping regions of Nedd8. In some embodiments, the invention comprises a chimeric polypeptide wherein the sequences bind to non-overlapping regions of SUMO.

In some embodiments, a ubiquitin-like protein according to the invention is a protein having properties that are similar to those of ubiquitin. Like ubiquitin, other members of the ubiquitin-protein family can be conjugated to non-ubiquitin-like proteins, and can form polyubiquitin-like protein chains comprising non-ubiquitin proteins. Thus, like ubiquitin, other members of the ubiquitin-like protein family can be free or conjugated. Members of the ubiquitin-like protein family are well known in the art, and regulate diverse biological processes. Examples of ubiquitin-like proteins include Nedd8, SUMO-1, SUMO-2, SUMO-3, NUB1, PIC1, UBL3, UBL5, FAT10 and ISG15.

As used herein, the terms "Nedd8" and "neuronal precursor cell expressed developmentally down-regulated protein 8" refer to a member of the family of ubiquitin-like proteins that is covalently attached to target proteins. The human, mouse, and rat Nedd8 sequences are each 81 amino acids in length and are about 6 kDa. The terms "Nedd8" and "neuronal precursor cell expressed developmentally down-regulated protein 8" also refer to the yeast Rubl protein. Nucleotide and amino acid sequences of NEDD8 proteins are known in the art.

In certain embodiments, a Nedd8 protein according to the invention has at least 80%, at least 85%, at least 90%, at least 95%, at least 98%, at least 99%, or 100% identity to a known Nedd8 protein, such as the human Nedd8 protein. In some embodiments, the Nedd8 protein has at least 80%, at least 85%, at least 90%, at least 95%, at least 98%, at least 99%, or 100% identity to the human Nedd8 protein SEQ ID NO: 23. In some embodiments, the Nedd8 protein is the human Nedd8 protein. In other embodiments, the Nedd8 protein according to the invention includes naturally occurring or engineered variants of Nedd8. Also encompassed by "Nedd8" are naturally occurring alleles and human engineered variants of a known Nedd8 protein. In some embodiments, Nedd8 comprises the sequence in SEQ ID NO: 23 with an amino acid substitution, for example for the purposes of generating a site on the Nedd8 protein to conjugate a detectable label.

In some embodiments, the invention comprises a chimeric polypeptide sensor comprising two or more polypeptide sequences that bind a Nedd8 protein wherein the sequences bind non-overlapping regions of the Nedd8 protein; and one or more linkers, wherein the linkers connect two or more of the sequences. In some embodiments, the invention comprises the chimeric polypeptide sensor wherein the chimeric polypeptide has three polypeptide sequences that bind to non-overlapping regions of Nedd8 proteins connected by two linkers. In some embodiments, the chimeric polypeptide sensor has a selective binding affinity for free Nedd8 protein compared to conjugated Nedd8 protein. In some embodiments, the chimeric polypeptide sensor has a selective binding affinity conjugated Nedd8 protein compared to free Nedd8 protein. In some embodiments, the chimeric polypeptide sensor has a selective binding affinity for Nedd8 compared to ubiquitin proteins or other ubiquitin-like proteins.

In certain embodiments, the invention comprises a chimeric polypeptide sensor comprising the ZnF UBP binding domain from Isopeptidase T and the ubiquitin interacting motif from Vps27. In some embodiments, chimeric polypeptide sensor comprising the zinc finger binding domain from Isopeptidase T and the ubiquitin interacting motif from Vps27 comprises the sequence listed in SEQ ID NO: 5. wherein the chimeric polypeptide sensor is termed tIV. In some embodiments, the tIV comprises a selective binding affinity for free Nedd8 compared to conjugated Nedd8. In some embodiments, tIV is tagged with a fluorophore. In some embodiments, tIV is tagged with a fluorophore connected at a linker. In some embodiments, the tIV has at least 80%, at least 85%, at least 90%, at least 95%, at least 98%, at least 99%, or 100% identity to SEQ ID NO: 5.

Small ubiquitin-like modifier (SUMO) proteins are a group of small proteins that bind lysine residues of target proteins and thereby modify target protein activity, stability, and sub-cellular localization. SUMO2 and SUMO3 proteins share a high degree of similarity (95% sequence identity), but are relatively distinct from SUMO1 (only 50% sequence identity). SUMO conjugation (or "sumoylation") is a highly volatile process, with various enzymes involved in the conjugation. A large portion of SUMO conjugation targets are transcription factors and other nuclear proteins involved in gene expression.

In certain embodiments of the invention, a SUMO protein according to the invention has at least 80%, at least 85%, at least 90%, at least 95%, at least 98%, at least 99%, or 100% identity to a known SUMO protein, such as the human SUMO1, SUMO2, or SUMO3 proteins. In some embodiments, the SUMO protein has at least 80%, at least 85%, at least 90%, at least 95%, at least 98%, at least 99%, or 100% identity to the human SUMO proteins set forth in SEQ ID NO: 24-26. In some embodiments, the SUMO protein is one of the human SUMO proteins. In other embodiments, the SUMO protein according to the invention includes naturally occurring or engineered variants of SUMO. Also encompassed by "SUMO" are naturally occurring alleles and human engineered variants of a known SUMO protein. In some embodiments, SUMO comprises a sequence set forth in SEQ ID NO: 24-26 with an amino acid substitution, for example for the purposes of generating a site on the SUMO protein to conjugate a detectable label.

In some embodiments, the invention comprises a chimeric polypeptide comprising two or more polypeptide sequences that bind a SUMO protein wherein the sequences bind non-overlapping regions of the SUMO proteins; and one or more linkers, wherein the linkers connect two or more of the sequences. In some embodiments, the invention comprises the chimeric polypeptide wherein the chimeric polypeptide has three polypeptide sequences that bind to non-overlapping regions of SUMO proteins connected by two linkers. In some embodiments, the chimeric polypeptide sensor has a selective binding affinity for free SUMO protein compared to conjugated SUMO protein. In some embodiments, the chimeric polypeptide sensor has a selective binding affinity conjugated SUMO protein compared to free SUMO protein. In some embodiments, the chimeric polypeptide sensor has a selective binding affinity for SUMO compared to ubiquitin proteins or other ubiquitin-like proteins.

The chimeric polypeptide sensors of the present invention can be designed to selectively bind to one or a subset of a group of ubiquitin proteins and ubiquitin-like proteins. The selective qualities of the chimeric polypeptides can depend on the sequences that bind to ubiquitin or ubiquitin-like proteins of which they are comprised, as well as the linkers that connect the sequences. For example, a chimeric polypeptide sensor can be designed to selectively bind to free ubiquitin protein compared to conjugated ubiquitin protein, and compared to ubiquitin-like proteins. In some embodiments, this can be achieved by linking three, non-overlapping ubiquitin binding domains with two linkers (see Examples 1 and 2). The tIVR, tIDR, and tISR chimeric polypeptide sensors are examples of chimeric polypeptide sensors that selectivity bind to free ubiquitin as compared to conjugated ubiquitin or ubiquitin-like proteins. Both of these chimeric polypeptide sensors bind to three, non-overlapping regions of ubiquitin protein. However, the tIVR chimeric polypeptide sensor can be tailored to have a greater affinity for conjugated ubiquitin by increasing the length of a linker region (see Example 2, FIGS. 10-12). Thus, both the sequences that bind to the ubiquitin or ubiquitin-like protein and the linker length determine the binding characteristics of the chimeric polypeptide sensor. The chimeric polypeptide receptor tSR is an example of a chimeric polypeptide receptor that can bind to a subset of ubiquitin proteins or ubiquitin-like proteins. The tSR comprises two sequences that bind to ubiquitin protein and one linker. The tSR is a shorted tISR, both chimeric polypeptide sensors comprise the S5a$^{UIM}$ and Ruz domains, but tSR lacks the IsoT$^{ZnF}$ domain. The tSR shows a similar binding affinity to free and conjugated ubiquitin protein (see example 8). Yet while tSR does not seem to distinguish between free and conjugated ubiquitin protein, tSR does show a greater affinity for ubiquitin protein than for non-ubiquitin proteins. This demonstrates that the number of sequences that bind to a ubiquitin or ubiquitin-like protein included can influence the properties of a binding protein. Another example of a chimeric polypeptide sensor that recognizes a subset of ubiquitin proteins or ubiquitin-like proteins is tIVL1 Cys. tIVL1 Cys shares the IsoT$^{ZnF}$ domain and Vps27$^{UIM}$ domain of tIVR, but lacks the Ruz binding domain. The tIVL1 Cys chimeric polypeptide selectively binds to free ubiquitin and free Nedd8 compared to conjugated ubiquitin protein and conjugated ubiquitin-like protein (see FIG. 7, example 2). Thus, different chimeric polypeptide sensors can be constructed to selectively bind to one or a subset of a group of ubiquitin proteins and ubiquitin like proteins.

In certain embodiments, chimeric polypeptides of the present invention are tagged with a detectable marker, including any of those described herein or known in the art. In particular embodiments, the detectable marker is a fluorophore or a quencher. In particular embodiments, the detectable marker is linked to a cysteine residue in the chimeric polypeptide.

Chimeric polypeptide sensors and competitor proteins of the present invention may be produced recombinantly using conventional molecular and cellular biology techniques known and available in the art. Accordingly, the present invention includes recombinant chimeric polypeptide sensors and chimeric competitor proteins, including any of those described herein.

Methods for Determining Amounts of Ubiquitin Protein and Ubiquitin-Like Protein

The present invention provides chimeric polypeptide sensors that can be used in a variety of assays, including assays for determining the presence of, an amount of, or a concentration of a ubiquitin protein or a ubiquitin-like protein in a sample. In some embodiments, the assays detect total ubiquitin protein, free ubiquitin protein, or conjugated ubiquitin protein, or two or more of these. In some embodiments, the assays detect total ubiquitin-like protein, free ubiquitin-like protein, or conjugated ubiquitin-like protein, or two or more of these. The present invention also provides chimeric polypeptide sensors that can be used to detect increases or decreases in the amounts of a ubiquitin protein or ubiquitin-like protein, e.g., a free or conjugated ubiquitin protein or ubiquitin-like protein. The present invention also provides chimeric polypeptide sensors that can be used in deubiquitinase assays and other assays to measure a deconjugation or release of a ubiquitin protein or a ubiquitin-like protein from a ubiquitin conjugate substrate. The present invention also provides chimeric polypeptides that can be used to screen for agents that increase or decrease amounts of either free or conjugated ubiquitin protein or free or conjugated ubiquitin-like protein.

In some embodiments, the invention comprises methods to quantify a ubiquitin protein or ubiquitin-like protein in vitro. In some embodiments, the total amount of the ubiquitin or the ubiquitin-like protein is quantified, whereas in other embodiments, the free and/or conjugated ubiquitin protein or ubiquitin-like protein is quantified.

In various embodiments of methods of the present invention, total target ubiquitin protein or total target ubiquitin-like protein is assayed using a chimeric polypeptide sensor that binds to both the free and conjugated target ubiquitin protein or both the free and conjugated target ubiquitin-like protein. In various embodiments of methods of the present invention, free target ubiquitin protein or free target ubiquitin-like protein is assayed using a chimeric polypeptide sensor that preferentially binds to the free target ubiquitin protein or the free target ubiquitin-like protein. One of skill in the art will appreciate that amounts of conjugated target ubiquitin protein or conjugated target ubiquitin-like protein may be readily determined based on a determination of the amount of free and total ubiquitin protein or ubiquitin-like protein, i.e., conjugated protein=total protein−free protein. Accordingly, certain assays described herein include determining both the amount of free and the total amount of a ubiquitin protein or a ubiquitin-like protein. As used herein, a "target" protein refers to the ubiquitin protein or ubiquitin-like protein being assayed. In particular instances, one portion of a sample is assayed using a chimeric polypeptide sensor that binds a both free and conjugated ubiquitin protein or a both free and conjugated ubiquitin-like protein to determine a total amount or concentration of the ubiquitin or ubiquitin-like protein in the sample, and another portion of the sample is assayed using a chimeric polypeptide sensor that preferentially binds to a free ubiquitin protein or a free ubiquitin-like protein to determine an amount of the free ubiquitin protein or free ubiquitin-like protein in the sample. The concentration of free/total ubiquitin protein or free/total ubiquitin-like protein can be determined based on the results of these two assays. In addition, the amount or concentration of conjugated ubiquitin protein or ubiquitin-like protein can also be extrapolated.

In various embodiments, methods of the present invention are used to determine an amount of a ubiquitin protein or a ubiquitin-like protein present in a sample. In particular embodiments, the sample is a biological sample. Biological samples include samples obtained from any living cell, tissue, organ or organism, including but not limited to, blood, serum, cells, tissues, a tissue biopsy, lung effluent, urine, or cell lysate. In certain embodiments, a cell lysate is obtained from cultured cells, e.g., cultured eukaryotic cells.

In various embodiments, methods or assays of the present invention are performed by measuring the direct binding of a chimeric polypeptide sensor to a ubiquitin protein or ubiquitin-like protein. In other embodiments, methods or assays of the present invention are performed by indirectly determining the binding of a chimeric polypeptide sensor to a ubiquitin protein or ubiquitin-like protein. In some embodiments, the present invention comprises a measurement of the displacement of a competitor ubiquitin protein or a competitor ubiquitin-like protein from the chimeric polypeptide sensor. As used herein, a "competitor" ubiquitin protein or ubiquitin-like protein refers to a ubiquitin protein or ubiquitin-like protein that is exogenous to the sample being assayed, i.e., it is not present in the sample being assayed. In certain embodiments, the competitor ubiquitin protein or ubiquitin-like protein competes with the ubiquitin protein or ubiquitin-like protein present in the same for binding to the chimeric polypeptide.

In various embodiments, a competitor ubiquitin protein or competitor ubiquitin-like protein is chosen from any ubiquitin protein or ubiquitin-like protein that can bind to a chimeric polypeptide sensor employed in a competition assay, regardless of the identity of the target ubiquitin protein or ubiquitin-like protein. In some embodiments the competitor ubiquitin protein or ubiquitin-like protein is tagged with a detectable label. In some embodiments, the competitor ubiquitin protein or competitor ubiquitin-like protein is the same protein as the target ubiquitin protein or target ubiquitin-like protein to be detected. For example, in Example 1 (see, FIG. 8) concentrations of free ubiquitin protein (the target ubiquitin protein) are measured in a competition assay using a free ubiquitin protein tagged with a fluorophore (competitor protein). In some embodiments, the target ubiquitin or ubiquitin like proteins are different. For example, in Example 2 (see FIG. 9) the target ubiquitin protein or target ubiquitin-like protein included free ubiquitin protein, conjugated ubiquitin protein, and Nedd8, but all three were measured in the presence of a free ubiquitin-tagged by a fluorophore. Conjugated ubiquitin and Nedd 8 (the targets) could be detected by the chimeric polypeptide sensor when the competitor was a free ubiquitin protein. These examples illustrate that the specific competitor protein does not need to be identical to a target protein, so long as both the target and the competitor can bind to the same sensor, and so long as the sensor can bind either the target or the competitor at a given time, but not both simultaneously.

In some embodiments, the present invention provides method for the detection of total ubiquitin proteins, free ubiquitin proteins, conjugated ubiquitin proteins, total ubiquitin-like proteins, free ubiquitin-like proteins, or conjugated ubiquitin-like proteins through the detection of a detectable label. In some embodiments, the chimeric polypeptide is tagged with a detectable label. In some embodiments, the detectable label is a fluorophore. In some embodiments, a competitor ubiquitin protein or a competitor ubiquitin-like protein is tagged with a detectable label, e.g., a fluorophore. In some embodiments, the detection comprises measuring fluorescence intensity. In some embodiments, the detection comprises measuring fluorescence anisotropy. In particular embodiments, both the chimeric polypeptide sensor and a competitor ubiquitin protein or a competitor ubiquitin-like protein are labeled with a detectable label. For example, one may be labeled with a fluorescence emitter and the other labeled with a fluorescence quencher, e.g., as used in FRET. In certain embodiments, the detection occurs at a single point in time, e.g., upon completion of the assay. In other embodiments, the detection occurs at two or more time points, or at two or more regular time intervals, during the assay.

The use of detectable labels is well known in the art. Detectable labels may be used according to the invention. Methods for conjugating polypeptides and detectable labels are well known in the art, as are methods for imaging using detectable labels. Chimeric polypeptide sensors tagged with a detectable label may be employed in a wide variety of assays, employing a wide variety of labels. In some embodiments of the present invention, detection of a species of ubiquitin protein or ubiquitin like protein can facilitated by attaching a detectable label to the chimeric polypeptide sensor. In some embodiments, detection of a species of ubiquitin protein or species of ubiquitin like protein can be facilitated by attaching a detectable label to a competitor ubiquitin protein or a competitor ubiquitin-like protein.

Examples of detectable labels include but are not limited to radionucleotides, enzymes, coenzymes, fluorescers, chemiluminescers, chromogens, enzyme substrates or cofactors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin, coumarin, Alexa488, Oregon green 488, rhodamine green, Alexa 532, Cy3, Bodipy 588/586, Alexa586, TAMRA, Rox, Alexa 594, Texas red, Bodipy 630/650, Cy5, Alexa647, IR Dye 680, IR Dye 680, IR Dye 700 DX, Cy5.5, Alexa 750, IR Dye 800CW, IR Dye 800, Atto 532, Atto 465; an example of a luminescent material is luminol; examples of bioluminescent materials include luciferase, luciferin, and aequorin; and examples of suitable radioactive material include 125 I, 131 I, 35 S, or 3 H. In some embodiments, the detectable labels include fluorescent proteins. Suitable fluorescent proteins include TagBFP, mTagBFP2, Azurite, EBFP2, mK$_d$lamal, Sirius, Sapphire, T-Sapphire, ECFP, Cerulean, SCFP3A, mTurquoise, mTurquoise2, monomeric Midoriishi-cyan, TagCFP, mTFP1, GFP, EGFP, Emeral, Superfolder GFP, monomeric Azami Green, TagGFP2, mUKG, mWasabi, Clover, mNeonGreen, EYFP, YFP, Citrine, Venus, SYFP2, TagYFP, monomeric Kusabira. Orange, MKOK, mKO2, mOrange, mOrange2, mRaspberry, mCherry, mStrawberry, mTangerine, tdTomato, TagRFP, TagRFP1, mApple, mRuby, mRuby2, TagRFP675, IFP14, iFRP, mKeima Red, LSS-mKate1, LSS-mKate2, mBeRFP, PA-GFP, PAmCherry 1, PATagRFP, K$_d$ ede green, K$_d$ ede red, KikGR1 green, KikGR1 red, PS-CFP2, mEos2 green, mEos2 red, mEos3.2 green, mEos3.2 red, PSmOrange. In some embodiments of the present invention, detectable labels also include quenchers suitable for fluorescence resonance energy transfer (FRET) pairings. Examples of suitable quenchers include Dabcyl, BHQ1, BHQ2, BHQ3, CY5Q, CY7Q, Iowablack FQ, Iowablack RQ, IR Dye QC-1, QSY35, QSKY7, QXL570, QXL610, QXL680.

In certain embodiments, the amount of a ubiquitin protein or a ubiquitin-like protein in a sample is determined indirectly by contacting a polypeptide sensor with a sample in the presence of a detectably-labeled competitor ubiquitin protein or ubiquitin-like protein, and the amount of the ubiquitin protein or the ubiquitin-like protein in the sample is assayed by measuring the displacement of the competitor protein from the polypeptide sensor. Thus, in some embodiments, the present invention includes assays to measure a detectable label tagged to a competitor ubiquitin protein or a competitor ubiquitin-like protein, wherein a property of the detectable label changes when the competitor ubiquitin protein or the competitor ubiquitin-like protein is bound to a chimeric polypeptide sensor as compared to when the ubiquitin protein or ubiquitin-like protein is not bound to the chimeric polypeptide. Examples of such competitor ubiquitin proteins are described herein and include, e.g., fluorescein-tagged ubiquitin (S20C), Atto532-tagged ubiquitin (S20C), and Alexa488-tagged ubiquitin (S20C).

In certain embodiments, the amount of a ubiquitin protein or a ubiquitin-like protein in a sample is determined either directly by contacting a detectably-labeled polypeptide sensor with a sample, and the amount of the ubiquitin protein or the ubiquitin-like protein in the sample is assayed by measuring a change in the detectable label. Thus, in some embodiments, the present invention includes assays to measure a detectable label tagged to a chimeric polypeptide sensor, wherein a property of the detectable label changes when the chimeric polypeptide sensor is bound to a ubiquitin protein or a ubiquitin-like protein as compared to when the chimeric polypeptide sensor is not bound to the ubiquitin protein or the ubiquitin-like protein. Examples of such chimeric polypeptide sensors are described herein and include, e.g., Atto532-tagged tIVR L1 Cys, Atto532-tagged tIV L1 Cys, Alexa488-tagged tIVR (R218C), and Atto532-tISRL1 Cys.

In some embodiments, the present invention comprises methods of detecting a ubiquitin protein or ubiquitin-like protein (e.g., total or free), using a chimeric polypeptide sensor in assays that measure fluorescence intensity. In some embodiments, the chimeric polypeptide sensor binds a fluorophore-tagged competitor ubiquitin protein or a fluorophore-tagged competitor ubiquitin-like protein, wherein the fluorescence intensity from the fluorophore-tagged competitor ubiquitin protein or fluorophore-tagged competitor ubiquitin-like protein is different when the fluorophore-tagged competitor ubiquitin or fluorophore-tagged competitor ubiquitin-like protein is bound to the chimeric polypeptide as compared to when the fluorophore-tagged competitor ubiquitin protein or fluorophore-tagged competitor ubiquitin-like protein is not bound to the chimeric polypeptide. In some embodiments, the binding of the chimeric polypeptide decreases the fluorescence intensity of the fluorophore-tagged competitor ubiquitin protein or fluorophore-tagged competitor ubiquitin-like protein. In some embodiments, the binding to the chimeric polypeptide increases the fluorescence intensity of the fluorophore-tagged competitor ubiquitin protein or fluorophore-tagged competitor ubiquitin-like protein.

In other related embodiments, the chimeric polypeptide sensors are fluorophore-tagged, and the fluorescence intensity from the fluorophore-tagged chimeric polypeptide sensor is different when bound to a ubiquitin protein or ubiquitin-like protein as compared to when it is not bound to the ubiquitin protein or ubiquitin-like protein. In some embodiments, the binding of the chimeric polypeptide decreases its fluorescence intensity. In some embodiments, the binding of the chimeric polypeptide increases its fluorescence intensity.

Fluorescent probes are widely used in the art and are incorporated into a wide array of techniques to study biological and biochemical processes. Fluorescence intensity has been widely applied over the last two decades due to the vast development of new fluorophores. Typically, an optical system illuminates and excites the sample at a specific wavelength selected by a high performance optical filter. As a result, the sample emits light and a second optical system collects the emitted light. Usually, the emitted light is of lower energy and thus is composed of a longer wavelength than the excitation light. Commercial instruments to measure fluorescence intensity are widely available, and many different products are available to measure fluorescence intensity in different experimental settings. Fluorescence may be measured by any means known or available in the art, including but not limited to fluorescence intensity, fluorescence anisotropy, and FRET.

Fluorescence polarization or anisotropy is a highly sensitive method for the detection of a species of ubiquitin protein or a species of ubiquitin-like protein according to the present invention. When fluorescent molecules are excited with plane polarized light, they emit a majority of light in the same polarized plane, provided that the molecule remains stationary during the lifetime of the excited state (4 nanoseconds in the case of fluorescein). However, if the molecule rotates or tumbles out of the plane of the exciting polarized light during the excited state, light is emitted in a different plane from that of the initial excitation. The degree to which the fluorescence emission vector moves from, e.g., a vertical to a horizontal plane is directly related to the mobility of the fluorescently labeled molecule. That is, if the fluorescently labeled molecules are large, they move very little and the emitted light remains highly polarized with respect to the excitation plane. By contrast, if the fluorescently labeled molecules are small, they rotate or tumble faster, and the resulting emitted light is depolarized relative to the excitation plane. Because anisotropy is a general property of fluorescent molecules, an advantage of measuring fluorescent anisotropy is that readouts are less dye dependent and less susceptible to environmental interferences such as pH changes than assays based on fluorescence intensity measurements. In some embodiments of the invention, a fluorophore tagged to a chimeric polypeptide sensor or a ubiquitin protein will have a different anisotropy when the chimeric polypeptide sensor is bound to ubiquitin protein as opposed to unbound, and anisotropy can be used as a measurement for the assays of the present invention. Measurement of fluorescence anisotropy can easily be performed by persons skilled in the art. Furthermore, measuring fluorescence anisotropy is particularly suitable for high-throughput applications. For example, commercial instruments exist that can measure polarization of samples present in 96-well microtiter dishes.

FRET is a distance-dependent interaction between the electronic excited states of two dye molecules in which excitation is transferred from a donor molecule to an acceptor molecule without emission of a photon. The efficiency of FRET is dependent on the inverse sixth power of the intermolecular separation, making it useful over distances comparable to the dimensions of biological macromolecules. Thus, FRET is an important technique for investigating a variety of biological phenomena that produce changes in molecular proximity. Some embodiments of the invention comprise the binding of a ubiquitin protein tagged with a first detectable label to a chimeric polypeptide sensor bound with a second detectable label. In some embodiments, one of the labels is a donor dye (e.g., fluorescence donor) and one of the labels is an acceptor dye (e.g., fluorescence quencher). The absorbance spectrum of an acceptor dye overlaps with the emission spectrum of a proximal intramolecular or intermolecular donor dye such that the fluorescence of the donor dye is substantially diminished, or quenched. Acceptor dyes may or may not be fluorescent themselves. Fluorescent acceptor dyes allow for ratio analysis of fluorescence from the donor and acceptor dyes by two-channel detection. In some applications, non-fluorescent acceptor dyes may be advantageous, because they eliminate background fluorescence that results from direct acceptor excitation.

In some embodiments, the present invention includes methods of detecting ubiquitin proteins or ubiquitin-like proteins with chimeric polypeptide sensors in assays that measure fluorescence anisotropy. In some embodiments, the chimeric polypeptide sensors bind a fluorophore-tagged ubiquitin protein or a fluorophore-tagged ubiquitin-like protein (e.g., a competitor protein), wherein the fluorescence anisotropy measured from the fluorophore-tagged ubiquitin protein or fluorophore-tagged ubiquitin-like protein is different when the fluorophore-tagged fluorophore-tagged ubiquitin or ubiquitin-like protein is bound to the chimeric polypeptide as compared to when the fluorophore-tagged ubiquitin protein or fluorophore-tagged ubiquitin-like protein is not bound to the chimeric polypeptide. In some embodiments, binding to the chimeric polypeptide sensor decreases the fluorescence anisotropy measured from the fluorophore-tagged ubiquitin protein or fluorophore-tagged ubiquitin-like protein. In some embodiments, binding to the chimeric polypeptide increases the fluorescence anisotropy measured from the fluorophore-tagged ubiquitin protein or the fluorophore-tagged ubiquitin-like protein. In some embodiments, the dissociation of the binding of the chimeric polypeptide decreases the fluorescence anisotropy measured from the fluorophore-tagged ubiquitin protein or fluorophore-tagged ubiquitin-like protein. In some embodiments, the dissociation of the binding to the chimeric polypeptide increases the fluorescence anisotropy measured from the fluorophore-tagged ubiquitin protein or the fluorophore-tagged ubiquitin-like protein. In other related embodiments, the chimeric polypeptide sensors are fluorophore-tagged, and the fluorescence anisotropy from the fluorophore-tagged chimeric polypeptide sensor is different when bound to a ubiquitin protein or ubiquitin-like protein as compared to when it is not bound to the ubiquitin protein or ubiquitin-like protein. In some embodiments, the binding of the chimeric polypeptide decreases its fluorescence anistropy. In some embodiments, the binding of the chimeric polypeptide increases its fluorescence anisotropy.

Certain embodiments of assays of the present invention utilize competition assays. In some embodiments, a premise of the competition assay is that the binding of the ubiquitin protein being detected to the chimeric polypeptide sensor excludes the binding of a competitor ubiquitin protein tagged with a detectable label to the chimeric polypeptide sensor. When the species of ubiquitin protein to be detected is not present, there is a high degree of binding between the chimeric polypeptide sensor and the detectable label-tagged competitor ubiquitin protein. When concentrations of the ubiquitin protein being detected are present, they compete with the detectable-tagged competitor ubiquitin proteins for binding to the chimeric polypeptide sensor. Thus, the presence of the ubiquitin protein being detected in the sample being assayed results in a lower degree of binding between the chimeric polypeptide and the tagged competitor ubiquitin protein. Since the properties of the detectable label attached to the competitor ubiquitin protein change when the tagged competitor ubiquitin protein is bound to the chimeric polypeptide sensor, the amount of tagged competitor ubiquitin protein bound to the chimeric sensor can be determined by measuring the properties of the detectable label. From this measurement, the amount of the ubiquitin protein being detected can also be determined. In some embodiments, the detectable label is a fluorophore, where in the amount of the ubiquitin protein being detected can be determined by measuring a property of fluorescence emitted by the fluorophore. In some embodiments, the measurement quantifies fluorescent intensity. In some embodiments, the measurement quantifies fluorescent anisotropy. In some embodiments, the chimeric polypeptide is tagged with a detectable label that can be paired with the fluorophore-tagged competitor ubiquitin for FRET. In some embodiments, the measurement of the detectable label can be compared to a designated control to determine a relative amount of the ubiquitin proteins being detected. In some embodiments, the measurement of the detectable label can be compared to values determined from a set of standards with known quantities of the ubiquitin protein being detected to determine the absolute amount of the ubiquitin protein being detected in the sample.

According to various embodiments of the invention, any chimeric polypeptide sensor of the invention can be incorporated into a competition assay as described above. This includes, but it not limited to chimeric polypeptide sensors comprising two or more sequences that bind a target ubiquitin protein; comprising two or more sequences that bind a target ubiquitin-like protein; comprising a sequence that binds ubiquitin C-terminal; comprising a sequence that binds the ubiquitin hydrophobic patch; comprising a sequence that binds to surface near ubiquitin Asp58; comprising a sequence that binds the ubiquitin C-terminal and a sequence that binds the ubiquitin hydrophobic patch; comprising a sequence that binds to the ubiquitin C-terminal and a sequence that binds to the surface near ubiquitin Asp58; comprising a sequence that binds to the ubiquitin hydrophobic patch and a sequence that binds to the surface near ubiquitin Asp58; comprising a sequence that binds the ubiquitin C terminal, a sequence that binds the ubiquitin hydrophobic patch, and a sequence that binds to the surface near ubiquitin Asp58; comprising the ZnF UBP binding domain from Isopeptidase T, comprising the Ruz domain from Rabex-5; comprising the ubiquitin interacting motif from Vps27; comprising the Ruz domain from Rabex-5 and the ubiquitin interacting motif from Vps27; comprising the ZnF UBP domain from Isopeptidase T and the Ruz domain from Rabex5; comprising the ubiquitin interacting motif from Vps27 and the Ruz domain from Rabex5; comprising the ZnF UBP binding domain from Isopeptidase T, the Ruz domain from Rabex-5, and the ubiquitin interacting motif from Vps27; comprising the ubiquitin binding associated domain from Dsk2; comprising the ZnF UBP binding domain from Isopeptidase T and the ubiquitin associated domain from Dsk2; comprising the Ruz domain from Rabex-5 and the ubiquitin associated domain from Dsk2; comprising the ZnF UBP binding domain from Isopeptidase T, the Ruz domain from Rabex-5, and the ubiquitin associated domain from Dsk2; comprising the ubiquitin interacting motif from S5a; or comprising the ZnF UBP binding domain from Isopeptidase T, the Ruz domain from Rabex-5, the ubiquitin interacting motif from S5a. Furthermore, this includes, but it not limited to: tIVR, tIDR, tISR, tSR, and tIV. In some embodiments, the chimeric polypeptide comprises a detectable label. In some embodiments, the competition assays also utilize a ubiquitin protein or ubiquitin-like protein tagged with a detectable label (e.g., a competitor protein). In some embodiments, the include competition assays utilize a ubiquitin or ubiquitin-like protein tagged with a fluorophore. In some embodiments, the competition assays utilize a chimeric polypeptide sensor with a detectable label and a ubiquitin protein or a ubiquitin-like protein tagged with a detectable label. In some embodiments, these include competition assays utilizing FRET imaging techniques.

In some embodiments, the present invention comprises methods of detecting ubiquitin protein or ubiquitin-like protein by detecting chimeric polypeptide sensor tagged with a detectable label. In some embodiments, the detection method comprises a direct titration assay. Direct titration assays are well known in the art, and any such method to perform titration assay is suitable. In some embodiments, the titration assay measures a ubiquitin protein to be determined. In some embodiments, the titration assay measures a ubiquitin-like protein to be determined. In some embodiments of the present invention, competitive assays comprise measuring fluorescence intensity. In some embodiments of the present invention, competitive assays comprise measuring fluorescence anisotropy.

In some embodiments of the present invention, a premise of the titration assay is that the binding of a ubiquitin protein or ubiquitin-like protein by the detectable label-tagged chimeric polypeptide alters the properties of the detectable label. For example, when the ubiquitin protein to be detected is not present, there is no degree of binding between the chimeric polypeptide sensor and the ubiquitin protein. When amounts of the ubiquitin protein being detected are present, they bind to the chimeric polypeptide sensor with a detectable label. Since the binding of the ubiquitin protein with the chimeric polypeptide sensor tagged with a detectable label changes the properties of detectable label, the amount of the ubiquitin protein bound to the chimeric sensor can be determined by measuring the detectable label. From this measurement, the amount of the ubiquitin protein in the sample can also be determined. In some embodiments, the detectable label is a fluorophore, wherein the amount of the ubiquitin protein can be determined by measuring a property of fluorescence emitted by the fluorophore. In some embodiments, the measurement quantifies fluorescent intensity. In some embodiments, the measurement quantifies fluorescent anisotropy. In some embodiments, the measurement of the detectable label can be compared to a designated control to determine a relative amount of the ubiquitin protein being detected. In some embodiments, the measurement of the detectable label can be compared to values determined from a set of standards with known quantities of the ubiquitin protein being detected to determine the absolute amount of the ubiquitin protein being detected in the sample.

According to some embodiments of the invention, any chimeric polypeptide sensor of the invention can be used in a direct titration assay as described above. This includes, but it not limited to chimeric polypeptide sensors comprising two or more sequences that bind ubiquitin protein; comprising two or more sequences that bind ubiquitin-like protein; comprising a sequence that binds ubiquitin C-terminal; comprising a sequence that binds the ubiquitin hydrophobic patch; comprising a sequence that binds to surface near ubiquitin Asp58; comprising a sequence that binds the ubiquitin C-terminal and a sequence that binds the ubiquitin hydrophobic patch; comprising a sequence that binds to the ubiquitin C-terminal and a sequence that binds to the surface near ubiquitin Asp58; comprising a sequence that binds to the ubiquitin hydrophobic patch and a sequence that binds to the surface near ubiquitin Asp58; comprising a sequence that binds the ubiquitin C terminal, a sequence that binds the ubiquitin hydrophobic patch, and a sequence that binds to the surface near ubiquitin Asp58; comprising the ZnF UBP binding domain from Isopeptidase T, comprising the Ruz domain from Rabex-5; comprising the ubiquitin interacting motif from Vps27; comprising the Ruz domain from Rabex-5 and the ubiquitin interacting motif from Vps27; comprising the ZnF UBP domain from Isopeptidase T and the Ruz domain from Rabex5; comprising the ubiquitin interacting motif from Vps27 and the Ruz domain from Rabex5; comprising the ZnF UBP binding domain from Isopeptidase T, the Ruz domain from Rabex-5, and the ubiquitin interacting motif from Vps27; comprising the ubiquitin binding associated domain from Dsk2; comprising the ZnF UBP binding domain from Isopeptidase T and the ubiquitin associated domain from Dsk2; comprising the Ruz domain from Rabex-5 and the ubiquitin associated domain from Dsk2; comprising the ZnF UBP binding domain from Isopeptidase T, the Ruz domain from Rabex-5, and the ubiquitin associated domain from Dsk2; or comprising the ubiquitin interacting motif from S5a; comprising the ZnF UBP binding domain from Isopeptidase T, the Ruz domain from Rabex-5, the ubiquitin interacting motif from S5a. Furthermore, this includes, but it not limited to: tIVR, tIDR, tISR, tSR, and tIV. In some embodiments, the chimeric sensor polypeptide is detectably labeled. In some embodiments, these include direct titration assays that use a chimeric polypeptide sensor tagged with a detectable label. In some embodiments, these include direct titration assays use a chimeric polypeptide sensor tagged with a fluorophore.

In some embodiments of the invention, competition assays and direct titration assays are suitable for determining an amount of a target ubiquitin protein or ubiquitin-like protein in vitro. In some embodiments, the assays described herein are suitable for determining an amount of a target ubiquitin protein or ubiquitin-like protein in a sample, e.g., a biological sample. In some embodiments of the invention, the competition assays and the direct titrations assays are suitable for determining an amount of a target ubiquitin protein or ubiquitin-like protein in extracts. In some embodiments of the invention, the extracts are from cultured cells. In some embodiments of the invention, the extracts are from tissue. The preparation of extracts from cell culture and from tissue for use in experiments as described herein are well known to those of skill in the art.

In certain embodiments, the present invention includes a method of determining the presence of, an amount of, or a concentration of a ubiquitin protein or a ubiquitin-like protein (i.e., target protein) in a sample, comprising: contacting the sample with a chimeric polypeptide sensor described herein for a period of time and directly or indirectly detecting an amount of the ubiquitin protein or ubiquitin-like protein bound to the chimeric polypeptide sensor.

In some embodiments, the ubiquitin protein or ubiquitin-like protein being assayed is the free ubiquitin protein or ubiquitin-like protein, and the chimeric polypeptide sensor preferentially binds to the free ubiquitin protein or ubiquitin-like protein.

In some embodiments, the ubiquitin protein or ubiquitin-like protein being assayed is the total ubiquitin protein or ubiquitin-like protein, including both the free and conjugated ubiquitin protein or ubiquitin-like protein, and the chimeric polypeptide sensor binds to both the free ubiquitin protein or free ubiquitin-like protein and the conjugated ubiquitin protein or conjugated ubiquitin-like protein.

In certain embodiments, the chimeric polypeptide sensor is detectably labeled, e.g., with a fluorophore, wherein the signal emitted by the label is altered upon binding to the target protein, and the amount of target protein bound to the chimeric polypeptide sensor is measured by detecting a change in the signal emitted by the label after contact with the sample or throughout the period of time, e.g., when the signal is detected at regular intervals throughout the period of time.

In other embodiments, the method comprises contacting the sample and the chimeric polypeptide sensor with a detectably labeled competitor ubiquitin protein or competitor ubiquitin-like protein for a period of time, wherein the signal emitted by the label is altered upon binding to the chimeric polypeptide sensor, and the amount of target protein bound to the chimeric polypeptide sensor is indirectly measured by detecting a change in the signal emitted by the label after contact between the labeled competitor protein and the chimeric polypeptide sensor in the presence of the sample. In certain embodiments, the competitor protein is pre-incubated with the chimeric polypeptide sensor before both are contacted by the sample, and a change in the signal emitted reflects competition by the target protein in the sample for binding to the chimeric polypeptide sensor.

In other embodiments, the method comprises contacting the sample and a detectably labeled chimeric polypeptide sensor with a detectably labeled competitor ubiquitin protein or competitor ubiquitin-like protein for a period of time, wherein the signal emitted by the labels is altered upon binding of the competitor protein to the chimeric polypeptide sensor, and the amount of target protein bound to the chimeric polypeptide sensor is indirectly measured by detecting a change in the signal emitted by the labels after contact between the labeled competitor protein and the labeled chimeric polypeptide sensor in the presence of the sample. In certain embodiments, either the chimeric polypeptide sensor or the competitor protein is labeled with a fluorescence emitter, and the other of the two is labeled with a quencher, wherein the pair of labels may be used in FRET. In certain embodiments, the competitor protein is pre-incubated with the chimeric polypeptide sensor before both are contacted by the sample, and a change in the signal emitted reflects competition by the target protein in the sample for binding to the chimeric polypeptide sensor.

In particular embodiments of any of the methods described herein, the sample is incubated with the chimeric polypeptide sensor and, optionally, the competitor protein, under conditions and for a duration of time sufficient to allow binding of the chimeric polypeptide sensor to the target ubiquitin protein or target ubiquitin-like protein in the same and/or the competitor protein. In certain embodiments, the conditions are any of those described in the accompanying Examples. In certain embodiments, the duration of time is at least 1 minute, at least 10 minutes, at least 30 minutes, at least one hour, at least two hours, or at least four hours. In certain embodiments, the assays are conducted in a solution approximating or having physiological conditions, including use of phosphate-buffered saline (25 mM Na phosphate pH 7.4, 150 mM NaCl) at a pH of 7.4, or Na HEPES or Na phosphate buffer at a pH of about 7.0, about 7.4, or about 7.5. In particular embodiments, assay mixtures additionally contain 0.1 mM tris-(carboxyethyl)phosphine hydrochloride to protect proteins from oxidation and 0.05% (w/v) Brij35 plus 0.2 mg/ml ovalbumin to reduce non-specific adsorption of proteins to surfaces (e.g., to quartz cuvette walls or plastic pipet tips). In particular embodiments, the binding step of the assays is performed at about 25 degrees C. or, for real-time deubiquitinase assays, at about 25 degrees C., or at about 30 degrees C., or at about 37 degrees C.

In particular embodiments of any of the methods described herein, the amount of target ubiquitin protein or target ubiquitin-like protein in the sample is determined by comparing the amount of detected signal to a predetermined value or set of values, or to a control value. In some embodiments, the predetermined control values are determined by performing the same assay using various known amounts of target protein instead of a test sample, to generate a set of known values. In some embodiments, a control value is determined by performing an assay concurrent with the test assay, but using a negative control instead of a test sample. In certain embodiments, a negative control is a sample that does not include the target ubiquitin protein or ubiquitin-like protein. In certain embodiments, a negative control is a protein that is not bound by the chimeric polypeptide sensor.

In particular embodiments of any of the methods described herein, the protein being detected is human ubiquitin protein, and the chimeric polypeptide sensor is a tIVR, tIVR L1 Cys, tIVR (R218C), tIDR, tISR, or tSR chimeric polypeptide sensor.

In particular embodiments of any of the methods described herein, the protein being detected is Nedd8, and the chimeric polypeptide is a tIV chimeric polypeptide sensor.

In some embodiments, the present invention includes a method to determine the presence of deubiquitinase activity or an amount of deubiquitinase activity. In some embodiments of the invention, the deubiquitinase assay is an in vitro assay to determine the deubiquitinase activity present in a sample or the deubiquitinase activity of a known, putative, or candidate deubiquitinase. In certain embodiments, the assay is used to screen a library comprising a plurality of compounds to identify a compound having deubiquitinase assay or a compound that activates or inhibits activity of a deubiquitinase enzyme. In particular embodiments, the library comprises a plurality of peptides or polypeptides.

In other embodiments, a deubiquitinase assay of the present invention may be used to assess the substrate promiscuity of a known, putative or candidate deubiquitinase by determining its activity using a plurality of different conjugated ubiquitin proteins and/or conjugated ubiquitin-like proteins. For example, the assay may be performed to determine the deubiquitinase activity of the known, putative or candidate deubiquitinase against ubiquitin proteins conjugated to a plurality of different substrate polypeptides, e.g., to determine whether the known, putative or candidate deubiquitinase specifically targets only one or a subset of ubiquitin-conjugated polypeptides. In certain instances, the assay is performed in multi-well dishes, e.g., 96-well plates, wherein each of the plurality of different ubiquitin-conjugated polypeptides is present in a discrete well.

In some embodiments, a deubiquitinase is defined as a protein with protease activity that removes ubiquitin and polyubiquitin chains from ubiquitinated proteins. Thus, provided a source of conjugated ubiquitin, a deubiquitinase will deconjugate the conjugated ubiquitin, and thereby increase the amount of free ubiquitin. In some embodiments of the invention, deubiquitinase activity is detected by a chimeric polypeptide sensor with preferential binding to free ubiquitin protein or free ubiquitin-like protein as compared to the conjugated ubiquitin protein or conjugated ubiquitin-like protein. In some embodiments, the deubiquitin assay is performed with any of the techniques or assays described, include competition assays and direct titration assays to detect free ubiquitin. In some embodiments, the deubiquitinase assay uses a chimeric polypeptide sensor tagged with a detectable label. In some embodiments, a competitor ubiquitin protein is tagged with a detectable label. In some embodiments, the deubiquitinase assay comprises the measurement of fluorescence properties. In some embodiments, the deubiquitinase assay comprises the measurement of fluorescence anisotropy. In some embodiments, the deubiquitinase assay comprises FRET.

A deubiquitinase assay detects deubiquitinase activity, which is the activity that breaks the covalent bonds between ubiquitin proteins and non-ubiquitin proteins. In a given sample, deubiquitinase activity increases the amount of free ubiquitin in the sample. In essence, a deubiquitinase assay determines if an amount of free ubiquitin is generated from a source of conjugated ubiquitin by a known or candidate deubiquitinase. Thus, any methods of the present invention that can detect free ubiquitin can be purposed towards detecting deubiquitinase activity. One strategy to detect deubiquitinase activity is to measure the amount of free ubiquitin in a sample containing a known or candidate deubiquitinase, and comparing it the amount of free ubiquitin in a negative control sample that does not contain the known or candidate deubiquitinase, whereby a greater amount of free ubiquitin in the presence of the known or candidate deubiquitinase compared to the negative control would confirm that the known or candidate is a deubiquitinase. Such a strategy could be employed by methods from multiple embodiments of the invention, including direct titration and competition assays. A second strategy is to measure the amount of free ubiquitin at two or more time periods in a mixture containing a known or candidate deubiquitinase, a source of conjugated ubiquitin, and the chimeric polypeptide sensor that preferentially binds to free ubiquitin as compared to conjugated ubiquitin. In some embodiments of the invention, two or more time points are monitored over a period of time. In some embodiments, the methods comprise taking measurements of free ubiquitin in a mixture at regular intervals over a period of time. If greater amounts of free ubiquitin are measured at later time points compared to earlier time points, it indicates the presence of deubiquitinase activity. In some embodiments, the measurements of free ubiquitin are performed before the known or candidate deubiquitinase contacts the mixture. In other embodiments, measurements are taken after the known or candidate deubiquitinase contacts the mixture. In some embodiments, the measurements are take both before and after the known or candidate deubiquitinase contacts the mixture.

In some embodiments of the invention, the methods comprise a series of steps, in any order, comprising contacting a chimeric polypeptide sensor that preferentially binds to free ubiquitin to a mixture, contacting a source of conjugated ubiquitin to the mixture, contacting a known or candidate deubiquitinase to the mixture for a period of time, and measuring the amount of free ubiquitin. In some embodiments, the methods comprise contacting a mixture first with a chimeric polypeptide sensor tagged with a detectable label and contacting the mixture with a source of conjugated ubiquitin, and next contacting the mixture with the known or candidate deubiquitinase. In other embodiments, the chimeric sensor contacts the mixture after the known or candidate deubiquitinase contacts the mixture. In some embodiments, the amount of ubiquitin is determined is determined through direct titration experiments, wherein the chimeric polypeptide sensor is tagged with a detectable label. In some embodiments, the amount of free ubiquitin is determined with a competition assay, wherein a competitor ubiquitin protein or ubiquitin-like protein tagged with a detectable label contacts the mixture. In some embodiments, the amount of free ubiquitin is measured with FRET, wherein the chimeric polypeptide sensor is tagged with a detectable label and the competitor ubiquitin protein or competitor ubiquitin-like protein.

In some embodiments of the invention, the term candidate deubiquitinase refers to an enzyme suspected to possess deubiquitinase activity. In some embodiments, candidate deubiquitinase refers to an agent being tested for or suspected to modify the deubiquitinase activitiy of the known dequibquitinase. In some embodiments, such agents can include, but are not limited to: small molecules and pharmaceutical compounds, proteasome inhibitiors, RNA or DNA oligonucleotides, antibodies, or other proteins. In such experiments, negative controls would include a group with no deubiquitinase, and a control with the known deubiquitinase but not the agent. If a presence of the agent in the mixture results in a different amount of free ubiquitin, either a greater or lower amount of free ubiquitin, then it can be conluced that the agent modifies the activity of the deubiquitinase. As indicated, methods of the present invnetion may also be practiced using known deubiquitinases, e.g., to measure their activity, e.g., in the presence of another compound, or to determine their substrate specificity.

In one particular embodiment, a deubiquitinase assay of the present invention comprises bringing into contact: (i) a chimeric polypeptide sensor that preferentially binds to a free ubiquitin protein or a free ubiquitin-like protein as compared to the conjugated ubiquitin protein or conjugated ubiquitin-like protein; (ii) one or more conjugated ubiquitin proteins or conjugated ubiquitin-like proteins; and (iii) one or more known or candidate ubiquitinases, for a period of time, e.g., a period of time sufficient to allow binding of the chimeric polypeptide sensor to free ubiquitin protein or free ubiquitin-like protein and deconjugation of ubiquitin. In particular embodiments, the chimeric polypeptide sensor is detectably labeled, and the signal generated by the label changes when the sensor is bound by free ubiquitin. In other embodiments, the ubiquitin protein or ubiquitin-like protein is labeled, and the signal generated by the label changes when the protein is bound by the chimeric polypeptide sensor. In other embodiments that utilize an indirect measurement, a labeled competitor free ubiquitin or competitor free ubiquitin-like protein is also brought into contact with (i)-(iii), wherein the signal generated by the label changes when the competitor protein is bound by the sensor as compared to when it is not bound by the sensor.

In some embodiments of the invention, a deubiquitinase assay is preformed using a conjugated ubiquitin protein with a detectable label tagged on the ubiquitin protein. In some embodiments, the detectable label is a fluorophore. In some embodiments, the deubiquitinase assay comprises contacting the tagged conjugated ubiquitin protein with a chimeric polypeptide sensor that preferentially binds free ubiquitin protein compared to conjugated ubiquitin protein, and contacting tagged conjugated ubiquitin protein with the tagged conjugated ubiquitin protein, and contacting the tagged the conjugated ubiquitin with a known or candidate deubiquitinase. In this deubiquitinase assay, deubiquitinase activity converts the tagged conjugated ubiquitin into tagged free ubiquitin. The newly free tagged ubiquitin binds to the chimeric polypeptide sensor, resulting in a detectable change in a signal from the detectable label. Increased binding of tagged free ubiquitin to the chimeric polypeptide sensors is a positive indicator of deubiquitinase activity in this dequbiquitinase assay.

In each of these assays, the amount of free ubiquitin may be determined by measuring the amount of detectable label. In certain embodiments, the presence of or amount of free ubiquitin is determined by measuring the change in the amount of label (e.g., fluorescence intensity, anisotropy, or FRET) detected at two or more different time points during the assay. In certain embodiments, the presence of or amount of free ubiquitin is determined by comparing the amount of label detected to a predetermined value or to a control value. Generally, an increase in the amount of free ubiquitin protein or free ubiquitin-like protein detected indicates the presence of deubiquitinase activity and, thus, identifies a compound as being a deubiquitinase.

According to some embodiments of the invention, any chimeric polypeptide sensor of the invention can be incorporated into a deubiquitinase assay as described above. This includes, but it not limited to chimeric polypeptide sensors: comprising two or more sequences that bind ubiquitin protein; comprising a detectable label; comprising two or more sequences that bind ubiquitin-like protein; comprising a sequence that binds ubiquitin C-terminal; comprising a sequence that binds the ubiquitin hydrophobic patch; comprising a sequence that binds to surface near ubiquitin Asp58; comprising a sequence that binds the ubiquitin C-terminal and a sequence that binds the ubiquitin hydrophobic patch; comprising a sequence that binds to the ubiquitin C-terminal and a sequence that binds to the surface near ubiquitin Asp58; comprising a sequence that binds to the ubiquitin hydrophobic patch and a sequence that binds to the surface near ubiquitin Asp58; comprising a sequence that binds the ubiquitin C terminal, a sequence that binds the ubiquitin hydrophobic patch, and a sequence that binds to the surface near ubiquitin Asp58; comprising the ZnF UBP binding domain from Isopeptidase T, comprising the Ruz domain from Rabex-5; comprising the ubiquitin interacting motif from Vps27; comprising the Ruz domain from Rabex-5 and the ubiquitin interacting motif from Vps27; comprising the ZnF UBP domain from Isopeptidase T and the Ruz domain from Rabex5; comprising the ubiquitin interacting motif from Vps27 and the Ruz domain from Rabex5; comprising the ZnF UBP binding domain from Isopeptidase T, the Ruz domain from Rabex-5, and the ubiquitin interacting motif from Vps27; comprising the ubiquitin binding associated domain from Dsk2; comprising the ZnF UBP binding domain from Isopeptidase T and the ubiquitin associated domain from Dsk2; comprising the Ruz domain from Rabex-5 and the ubiquitin associated domain from Dsk2; comprising the ZnF UBP binding domain from Isopeptidase T, the Ruz domain from Rabex-5, and the ubiquitin associated domain from Dsk2; comprising the ubiquitin interacting motif from S5a; comprising the ZnF UBP binding domain from Isopeptidase T, the Ruz domain from Rabex-5, the ubiquitin interacting motif from S5a; further, this includes, but it not limited to: tIVR, tIDR, tISR, tSR, and tIV. In some embodiments, these include deubiquitinase assays that comprise a ubiquitin protein or ubiquitin like protein tagged with a detectable label. In some embodiments, these include deubiquitinase assays that comprise a ubiquitin or ubiquitin-like protein tagged with a fluorophore. In some embodiments, these include deubiquitinase assays that comprise a chimeric polypeptide sensor with a detectable label and a ubiquitin protein or a ubiquitin like protein tagged with a detectable label. In some embodiments, these include deubiquitinase assays comprising FRET imaging techniques.

In some embodiments of the invention, competition, direct titration, and deubiquitinase assays can be incorporated into high throughput screens to detect novel compounds or agents that influence ubiquitin proteins or ubiquitin-like proteins. In some embodiments, the invention includes any of the methods to detect free ubiquitin protein or free ubiquitin-like protein described herein in concert with screens to evaluate the effects of different agents or compounds on pools, e.g., amounts, of free ubiquitin. In particular embodiments, a library of compounds or agents is screened to identify a compound or agent that either increases or decreases ubiquitination or deubiquitination of a substrate polypeptide. In some embodiments, the agents or compounds are small molecules, and in some embodiments, the agents or compounds are peptides or polypeptides.

Any methods of the present invention that can detect free ubiquitin or ubiquitin-like protein can be purposed towards a high throughput screen to detect agents that influence conjugation or deconjugation of ubiquitin or ubiquitin-like proteins. One strategy to detect modifiers of conjugation or deconjugation of ubiquitin or ubiquitin-like proteins is to measure the amount of free ubiquitin in a sample containing a candidate agent, and compare it the amount of free ubiquitin in a negative control sample that does not contain the candidate agent, whereby a greater or lesser amount of free ubiquitin in the presence of the candidate agent compared to the negative control would confirm that the candidate influences conjugation or deconjugation. Such a strategy is employed according to certain embodiments of any of the methods of the invention, including direct titration and competition assays.

In some embodiments of the invention, a candidate agent is tested prior to detecting free ubiquitin. In some embodiments, agents can include, but are not limited to, small molecules and pharmaceutical compounds, DNA or RNA oligonucleotides, methods of gene silencing, proteins, or antibodies. In some embodiments, the candidate agent is contacted to an organism or a tissue before a tissue sample from the organism or the tissue is collected. In such cases, the agent can be administered to an experimental organism, including, but not limited to, nematoads, fruitflies, mice, rats, or plants. In some embodiments, the agent can be tested in cultured cells prior to preparing the cells as an extract. In some embodiments the agent contacts an extract prepared from a cell culture or tissue before the chimeric sensor contacts the extract. In some of these embodiments, the agent is tested on biological processes that occur without the presence of a chimeric polypeptide sensor and, optionally, a competitor protein. In such screens, the chimeric sensor is employed to determine the effect of the agent by detecting an amount of free ubiquitin present in extracts after biological processes or activities the agent is suspected to influence have taken place. Chimeric polypeptide sensors tagged with a detectable label, or chimeric polypeptide sensors and competitor ubiquitin protein or competitor ubiquitin-like protein tagged with a detectable label, or chimeric polypeptide sensors tagged with a detectable label and competitor ubiquitin protein or ubiquitin-like protein tagged with a detectable label, are then contacted to the extract to determine the amount of free ubiquitin in the extract though direct titration, competition assay, or FRET methods, respectively.

According to some embodiments of the invention, one strategy to determine if an agent influences ubiquitin protein or ubiquitin-like protein conjugation or deubiquitinase activity is to measure the amount of free ubiquitin or free ubiquitin-like protein in a sample comprising an agent, and comparing it the amount of free ubiquitin in a negative control sample that does not contain the agent, whereby a change in the amount of free ubiquitin in the presence of the agent as compared to the negative control confirms that the agent alters ubiquitin protein or ubiquitin-like protein conjugation or deconjugation. In this strategy, the agent is contacted to a mixture with a known entity that acts to conjugate or deconjugate ubiquitin to a substrate. For example such entities can include, but are not limited to, proteins such as deubiquitinases or ubiquitin E1, E2, or E3 ligases. In various embodiments, such a strategy employs methods from various embodiments of the invention, including direct titration and competition assays. A second strategy is to measure the amount of free ubiquitin at two or more time periods in a mixture comprising the agent, the entities that conjugate or deconjugate ubiquitin or ubiquitin-like proteins, and a chimeric polypeptide sensor. In some embodiments of the invention, two or more time points are monitored over a period of time. In some embodiments, the methods comprise taking measurements of free ubiquitin in a mixture at regular intervals over a period of time. If the presence of the agent reduces the change in free ubiquitin protein or free ubiquitin-like protein observed across the measurements, then the agent can be concluded to inhibit the entity. If a larger change in the amount of free ubiquitin is observed, the agent can be concluded to enhance the conjugation or deconjugation activity of the entity.

In some embodiments of the invention, the methods comprise a series of steps, in any order, comprising contacting a chimeric polypeptide sensor that preferentially binds to free ubiquitin to a mixture, contacting a source of conjugated ubiquitin to the mixture, contacting a candidate agent to the mixture comprising a known ubiquitin conjugating enzyme or deubiquitinase for a period of time, and measuring the amount of free ubiquitin. In some embodiments, the methods comprise contacting a mixture first with a chimeric polypeptide sensor tagged with a detectable label, contacting the mixture with a source of conjugated ubiquitin, and next contacting the mixture with the candidate deubiquitinase. In other embodiments, the chimeric sensor contacts the mixture after the agent contacts the mixture. In some embodiments, the amount of ubiquitin is determined through direct titration experiments, wherein the chimeric polypeptide sensor is tagged with a detectable label. In some embodiments, the amount of free ubiquitin is determined with a competition assay, wherein a competitor ubiquitin protein or ubiquitin-like protein tagged with a detectable label is also contacted to the mixture. In some embodiments, the amount of free ubiquitin is measured with FRET, wherein the chimeric polypeptide sensor is tagged with a detectable label and the competitor ubiquitin protein or competitor ubiquitin-like protein is also tagged with a detectable label.

Competition assays and direct titration assays utilizing a chimeric polypeptide sensor to detect free ubiquitin, including any of those described herein, can be modified into a high throughput screen to test candidate agents for their abilities to modify pools of free ubiquitin. Such agents may include but are not limited to small molecules such as, pharmaceutical compounds, known or putative proteasome inhibitors; antibodies; proteins; nucleotides include DNA expression constructs, antisense oligonucleotides, RNAi, shRNA, siRNA. In certain embodiments, the amount of detected free ubiquitin in the presence of a candidate agent is compared to a designated negative control, wherein a greater amount of free ubiquitin associated with the presence of the candidate agent indicates that the candidate agent decreases conjugation of the ubiquitin protein or acts as a deubiquitinase, and a lesser amount of free ubiquitin associated with the presence of the agent indicates that the agent increases the conjugation of the ubiquitin protein or decreases ubiquitination, e.g., inhibits a deubiquitinase. In some embodiments of the present invention, the screens are competition assays that utilize fluorescence intensity or anisotropy detection. In some embodiments, the screens utilize FRET detection. In some embodiments, measurements of free ubiquitin are made using a real-time assay, wherein a change in the amount of free ubiquitin over time indicates the presence of an agent that modulates ubiquitination. In some embodiments of the invention, the amount of free ubiquitin-like protein is determined.

In certain embodiments, the screens are performed in a high throughput assay, e.g. wherein discrete wells of a multi-well plate include a chimeric polypeptide sensor that preferentially binds to a free ubiquitin protein or a free ubiquitin-like protein and one or more conjugated ubiquitin protein or conjugated ubiquitin-like protein, which serves as a substrate of a candidate agent that modulates ubiquitination or deubiquitination. Alternatively to, or in addition to, the conjugated ubiquitin protein or conjugated ubiquitin-like protein, the wells may include a free ubiquitin protein and a ubiquitin protein substrate, or a free ubiquitin-like protein and a ubiquitin-like protein substrate, which may be conjugated by the free ubiquitin protein or the free ubiquitin-like protein. Different candidate agents are added to different wells, and their effect on the amount of free ubiquitin protein or free ubiquitin-like protein. The assay may employ a detectably labeled chimeric polypeptide sensor that emits differently when bound or unbound to ubiquitin or a ubiquitin-like protein, and/or a detectably labeled competitor ubiquitin protein or competitor ubiquitin-like protein that emits differently when bound or unbound to the sensor.

According to some embodiments of the invention, any chimeric polypeptide sensor of the invention can be incorporated into a screen as described above. This includes, but it not limited to chimeric polypeptide sensors: comprising two or more sequences that bind ubiquitin protein; comprising a detectable label; comprising two or more sequences that bind ubiquitin-like protein; comprising a sequence that binds ubiquitin C-terminal; comprising a sequence that binds the ubiquitin hydrophobic patch; comprising a sequence that binds to surface near ubiquitin Asp58; comprising a sequence that binds the ubiquitin C-terminal and a sequence that binds the ubiquitin hydrophobic patch; comprising a sequence that binds to the ubiquitin C-terminal and a sequence that binds to the surface near ubiquitin Asp58; comprising a sequence that binds to the ubiquitin hydrophobic patch and a sequence that binds to the surface near ubiquitin Asp58; comprising a sequence that binds the ubiquitin C terminal, a sequence that binds the ubiquitin hydrophobic patch, and a sequence that binds to the surface near ubiquitin Asp58; comprising the ZnF UBP binding domain from Isopeptidase T, comprising the Ruz domain from Rabex-5; comprising the ubiquitin interacting motif from Vps27; comprising the Ruz domain from Rabex-5 and the ubiquitin interacting motif from Vps27; comprising the ZnF UBP domain from Isopeptidase T and the Ruz domain from Rabex5; comprising the ubiquitin interacting motif from Vps27 and the Ruz domain from Rabex5; comprising the ZnF UBP binding domain from Isopeptidase T, the Ruz domain from Rabex-5, and the ubiquitin interacting motif from Vps27; comprising the ubiquitin binding associated domain from Dsk2; comprising the ZnF UBP binding domain from Isopeptidase T and the ubiquitin associated domain from Dsk2; comprising the Ruz domain from Rabex-5 and the ubiquitin associated domain from Dsk2; comprising the ZnF UBP binding domain from Isopeptidase T, the Ruz domain from Rabex-5, and the ubiquitin associated domain from Dsk2; comprising the ubiquitin interacting motif from S5a; comprising the ZnF UBP binding domain from Isopeptidase T, the Ruz domain from Rabex-5, the ubiquitin interacting motif from S5a; further, this includes, but it not limited to: tIVR, tIDR, tISR, tSR, and tIV. In some embodiments, these include screens that comprise a ubiquitin protein or ubiquitin like protein tagged with a detectable label. In some embodiments, these include screens that comprise a ubiquitin or ubiquitin-like protein tagged with a fluorophore. In some embodiments, these include screens that comprise a chimeric polypeptide sensor with a detectable label and a ubiquitin protein or a ubiquitin like protein tagged with a detectable label. In some embodiments, these include screens comprising FRET imaging techniques.

In some embodiments, the present invention contains methods to determine the level of ubiquitin proteins (e.g., total or free) that are present in the serum of a patient. Stress or trauma can increase levels of extracellular ubiquitin proteins present in serum. Furthermore, there are extracellular ubiquitin receptors that can bind to the extracellular ubiquitin receptors. An example of an extracellular ubiquitin receptor is CXCR4. CXCR4 is a G-protein coupled receptor that can bind to extracellular ubiquitin protein. Upon binding the extracellular ubiquitin protein, CXCR4 becomes activated and can influence cellular processes. However, CXCR4 is only activated by ubiquitin proteins that are intact. Extracellular ubiquitin proteins can be partially degraded in serum, and partially degraded ubiquitin proteins do not activate CXCR4. Of particular importance may be the presence of the C-terminal domain on the ubiquitin proteins; an intact C-terminus of an extracellular ubiquitin is required to activate the CXCR4.

In some embodiments, the present invention includes methods to detect the presence of free ubiquitin in serum. In some embodiments, the method utilizes a chimeric polypeptide sensor comprising a polypeptide sequence that binds to ubiquitin C-terminus. In some embodiments, the method utilizes a chimeric polypeptide sensor wherein the chimeric polypeptide sensor has a selective binding affinity for free ubiquitin comprising an intact C-terminal as compared to partially degraded free ubiquitin or ubiquitin-like proteins. In certain embodiments, the chimeric polypeptide sensor comprises a sequence that binds to the C-terminus of a free ubiquitin protein. In some embodiments, the chimeric polypeptide sensor can be used in any of the assays of the invention described herein. In some embodiments, these assays are competition assays. In some embodiments, these assays comprise direct titration assays. In some embodiments, the chimeric polypeptide comprises a detectable label. In some embodiments, the method utilizes a competitor ubiquitin protein tagged with a detectable label. In some embodiments, the detectable label is a fluorophore. In some embodiments, the method comprises detecting fluorescence intensity. In some embodiments, the method comprises detecting fluorescence anisotropy. In some methods, the method comprises FRET.

EXAMPLES

The present invention will be described in greater detail by way of specific examples. The following examples are offered for illustrative purposes, and are not intended to limit the invention in any manner. Those of skill in the art will readily recognize a variety of noncritical parameters that can be changed or modified to yield essentially the same results.

Example 1

Design and Construction of Chimeric Polypeptides

This example demonstrates the design and subsequent generation of chimeric polypeptides that bind to free ubiquitin proteins. Ubiquitin proteins can simultaneously interact with ubiquitin binding domains that bind to non-overlapping regions of ubiquitin (see FIG. 1). Chimeric polypeptides were designed that comprise a domain that could bind to the ubiquitin C terminus, a domain that binds the ubiquitin hydrophobic surface patch, and a domain that binds to the surface of ubiquitin near Asp58. These three binding domains were connected by two linker peptides to generate chimeric polypeptides that act as sensors for free ubiquitin proteins (see FIG. 2). These three ubiquitin binding domains can be connected by two linkers, resulting in a chimeric polypeptide that simultaneously binds the ubiquitin protein in three non-overlapping regions.

Using this strategy, two prototype chimeric polypeptide sensors were constructed. Both prototype chimeric polypeptides contain a domain that binds the ubiquitin C terminus, a domain that binds the ubiquitin hydrophobic patch, and a domain that binds to the surface of ubiquitin near Asp58 that are connected by polypeptide linkers (see FIG. 3). In the first prototype (tIVR), the domain that binds to the C terminus of ubiquitin is the ZnF UBP domain of Isopeptidase T (IsoT$^{ZnF}$), the domain that binds to the ubiquitin hydrophobic patch is the ubiquitin-interaction motif from the Vps27 protein (Vps27$^{UIM}$), and the domain that binds to the surface of ubiquitin near Asp58 is the Rabex-5 ubiquitin binding zinc finger (Ruz). In the second prototype (tIDR), the IsoT$^{ZnF}$ and Ruz domains are linked to the ubiquitin associated (UBA) domain of the Dsk2 protein (Dsk2$^{UBA}$) which binds to the ubiquitin hydrophobic patch. Amino acid sequences of the chimeric polypeptides are provided.

The amino acid sequences were as follows:

tIVR:
MGSSHHHHHHSSGLVPRGSHHMKQEVQAWDGEVRQVSKHAFSLKQLDNPAR

IPPSGWKCSKCDMRENLWLNLTDGSILCGRRYFDGSGGNNHAVEHYRETG

YPLAVKLGTITPDGADVYSYDEDDMVLDPSLAEHLSHFGIDMLKMQK<u>GSA</u>

<u>AAEEAELDLKAAIQESLREA</u><u>GGGS</u>DLLCKKGCGYYGNPAWQGFCSKCWRE

EYHKARQK (Underline shows each linker; SEQ ID NO: 1)

tIDR:
MGSSHHHHHHSSGLVPRGSHHMKQEVQAWDGEVRQVSKHAFSLKQLDNPA

RIPPSGWKCSKCDMRENLWLNLTDGSILCGRRYFDGSGGNNHAVEHYRET

GYPLAVKLGTITPDGADVYSYDEDDMVLDPSLAEHLSHFGIDMLKMQKT<u>G</u>

<u>GSGGSGSGGSG</u>PPEERYEHQLRQLNDMGFFDFDRNVAALRRSGGSVQGAL

DSLLN<u>GGGGGSSGGGS</u>DLLCKKGCGYYGNPAWQGFCSKCWREEYHKARQK (Underline shows each linker; SEQ ID NO: 4)

Structural models of the prototype chimeric polypeptide sensors binding to the ubiquitin protein have been provided (see FIG. 4). The tIVR sensor is depicted with the IsoT$^{ZnF}$, the Vps27$^{UIM}$, and the Ruz domains bound to the ubiquitin C terminus, the ubiquitin hydrophobic patch, and the ubiquitin surface near Asp58, respectively. The tIDR sensor is depicted with the IsoT$^{ZnF}$, the Dsk2$^{UBA}$, and the Ruz domains bound to the ubiquitin C terminus, the ubiquitin hydrophobic patch, and the ubiquitin surface near Asp58, respectively.

The binding affinities of tIVR and tIDR to fluorophore-tagged ubiquitin were determined. The values were calculated from assays incorporating fluorophore-labeled ubiquitin. Experiments were performed with fluorescein, Atto532, and Alexa488-tagged ubiquitin in which maleimide derivatives of the fluorophores were attached to residue Cys20 (see FIG. 5). The affinity of tIVR for free fluorophore-tagged ubiquitin proteins was measured by detecting changes in fluorescence intensity or fluorescence anisotropy. These experiments took advantage of the fact that the fluorescent properties of fluorophore-tagged ubiquitin protein changes when it is bound to tIVR. Different concentrations of tIRV were added to fluorescein-tagged ubiquitin proteins. The affinity between tIVR and Alexa488-tagged ubiquitin or Atto532-tagged ubiquitin was measured by detecting change in fluorescence intensity. Different concentrations of tIVR were added to 50 pM Atto532-tagged ubiquitin or 100 pM Alexa488-tagged tagged ubiquitin. Adding tIVR to the fluorophore-tagged ubiquitin increased the amounts of fluorophore-tagged ubiquitin bound to tIVR, and thus decreased the fluorescence intensity (see FIG. 6, left). Affinity between fluorescein-tagged ubiquitin and tIDR was measured as the ratio of association and dissociation rates. Time-dependent changes in fluorescence anisotropy of 50 nM fluorescein-tagged ubiquitin were measured with and without 26 nM tIDR to measure association rates. Dissociation of 50 nM tIDR from its complex with 50 nM fluorescein-tagged ubiquitin was measured by detecting change in fluorescence anisotropy upon addition of a 100-fold excess of non-fluorescent ubiquitin (see FIG. 6, right).

The binding affinities of chimeric polypeptide sensors were compared to chimeric polypeptide sensors with different ubiquitin binding domains. The chimeric polypeptides were tagged with an Atto532 label. When the Atto532-tagged chimeric polypeptide is bound to a ubiquitin protein, the fluorescence intensity is altered. This allows for the fluorescent detection of interactions between ubiquitin proteins and Atto532-tagged chimeric polypeptides. The affinities of Atto532-tagged chimeric polypeptides comprising three (tIVR L1 Cys), two (tIV L1 Cys), or one (IsoT$^{ZnF}$ (S227C)) ubiquitin binding domains were determined (see figure7). Their amino acid sequences are as follows:

tIVR L1 Cys
(SEQ ID NO: 2)
MGSSHHHHHHSSGLVPRGSHMKQEVQAWDGEVRQVSKHAFSLKQLDNPAR

IPPSGWKCSKCDMRENLWLNLTDGSILCGRRYFDGSGGNNHAVEHYRETG

YPLAVKLGTITPDGADVYSYDEDDMVLDPSLAEHLSHFGIDMLKMQKGSC

AAAEEAELDLKAAIQESLREAGGGSDLLCKKGCGYYGNPAWQGFCSKCWR

EEYHKARQK tIV L1 Cys
(SEQ ID NO: 5)
MGSSHHHHHHSSGLVPRGSHMKQEVQAWDGEVRQVSKHAFSLKQLDNPAR

IPPSGWKCSKCDMRENLWLNLTDGSILCGRRYFDGSGGNNHAVEHYRETG

YPLAVKLGTITPDGADVWSYDEDDMVLDPSLAEHLSHFGIDMLKMQKGSC

AAAEEAELDLKAAIQESLREA

IsoT$^{ZnF}$ (S227C)
(SEQ ID NO: 31)
MPSSHHHHHHSSGLVPRGSHMKQEVQAWDGEVRQVSKHAFSLKQLDNPAR

IPPSGWKCSKCDMRENLWLNLTDGSILCGRRYFDGCGGNNHAVEHYRETG

YPLAVKLGTITPDGADVYSYDEDDMVLDPSLAEHLSHFGIDMLKMQK

The bold "C" represents the fluorophore attachment site for each chimeric polypeptide.

The determined $K_d$ for each construct (see FIG. 7) demonstrate the strong binding achieved by linking 3 non-overlapping ubiquitin binding domains.

This example shows that a chimeric peptide with strong affinity to ubiquitin proteins has been constructed by linking more than one binding domain that can simultaneously bind to ubiquitin in non-overlapping regions.

Example 2

Binding Specificities of the Chimeric Polypeptides

The specificity of the chimeric polypeptide sensor for free ubiquitin was demonstrated by comparing the binding affinities of the chimeric polypeptide sensors to free ubiquitin with the binding affinities to conjugated ubiquitin proteins or ubiquitin-like proteins (see FIG. 8). A competition assay was performed to determine the binding affinity of tIVR to free ubiquitin, conjugated ubiquitin, or nedd8, a ubiquitin-like protein. When bound to tIVR, the Atto532-tagged ubiquitin display reduced fluorescent intensity when stimulated compared to Atto532-tagged ubiquitin that is unbound to tIVR. The competitor proteins, free ubiquitin, conjugated ubiquitin (UB-GB1), or Nedd8 were added to a 10 nM tIVR and 10 nM Atto532-tagged ubiquitin mixture. Their amino acid sequences are as follows:

Ubiquitin
(SEQ ID NO: 22)
MQIFVKTLTGKTITLEVEPSDTIENVKAKIQDKEGIPPDQQRLIFAGKQL
EDGRTLSDYNIQKESTLHLVLRLRGG Nedd8
(SEQ ID NO: 23)
MLIKVKTLTGKEIEIDIEPTDKVERIKERVEEKEGIPPQQQRLIYSGKQM
NDEKTAADYKILGGSVLHLVLALRGG UB-GB1
(SEQ ID NO: 32)
MGSSHHHHHHSSGLVPRGSHMQIFVKTLTGKTITLEVEPSDTIENVKAKI
QDKEGIPPDQQRLIFAGKQLEDGRTLSDYNIQKESTLHLVLRLRGGQYKL
ALNGKTLKGETTTEAVDAATAEKVFKQYANDNGVDGEWTYDDATKTFTVT Since Atto532-tagged ubiquitin displaced from tIVR has enhanced fluorescence emission, increased fluorescence intensity indicates binding of competitor proteins to tIVR. These data indicated that the tIVR polypeptide has an approximately 3000-fold higher affinity for free ubiquitin than for conjugated ubiquitin or Nedd8.

While tIVR shows a higher affinity to free ubiquitin than to conjugated ubiquitin, it has similar binding affinities for different kinds of free polyubiquitin. A competition assay was performed testing 0.8 nM Atto532-tagged ubiquitin and 6 nM tIVR. Fluorescence intensity was measured as different concentrations of different linkage types of polyubiquitin proteins were added. The binding affinities of each linkage-type polyubiquitin are listed in a table, and all $K_d$ values fell within a range of 27-48 nM (see FIG. 9). This demonstrates that tIVR can provide a readout of free polyubiquitin without bias regarding linkage type.

In addition to the binding domains, the linkers of the chimeric polypeptide can also influence the binding specificity of the chimeric polypeptide. Reducing the length of linker 1 (SEQ ID NO: 30) connecting the domain that binds the ubiquitin C terminus with the domain that binds the ubiquitin hydrophobic patch increases the binding of tIVR to free ubiquitin compared to a ubiquitin-protein conjugate (see FIG. 10). Further analysis showed that a minimal length for linker 1 helps the chimeric polypeptide sensors achieve more selectivity for free ubiquitin over conjugated ubiquitin (see FIG. 11). While tIVR with different length linker 1 regions could bind free ubiquitin with high affinity, tIVR with a short linker 1 (SEQ ID NO: 13) showed less affinity for a conjugated ubiquitin (Ub-GB1) than tIVR with a long linker 1 (SEQ ID NO: 28; see FIG. 12).

Example 3

Use of Fluorescence Intensity as a Readout

The chimeric polypeptide sensors can be used with assays that measure fluorescence intensity to detect free ubiquitin. When chimeric polypeptide sensors bind a fluorophore-tagged ubiquitin protein, the fluorescence intensity is reduced compared to when the fluorophore-tagged ubiquitin is unbound. Alternatively, when a fluorophore-tagged chimeric polypeptide sensor is bound to a ubiquitin protein, the fluorescence intensity is increased compared to when the chimeric polypeptide is unbound (see FIG. 13).

Fluorophore-tagged ubiquitins have altered fluorescence intensity when they are bound totIVR (see FIG. 14). The fluorescence intensity of fluorescein, Alexa488, or Atto532-tagged ubiquitin in the presence of tIVR compared to the absence of tIVR was experimentally determined. Fluorescence intensities of fluorescein, Alexa488, or Atto532-tagged ubiquitin in the presence or absence of tIVR is graphed; complex formation with tIVR results in decreased fluorescence. Conversely, fluorescence of Atto465, Atto532, and Alexa488-tagged tIVR exhibited greater fluorescence intensity when bound to ubiquitin.

Another chimeric polypeptide sensor, Atto532-tISRL1 Cys2, was constructed. This chimeric polypeptide comprises three binding domains. Atto532-tISRL1 Cys2 shows a large fluorescence intensity change upon binding to free ubiquitin proteins. In this chimeric polypeptide sensor, L1 Cys2 is the linker between the IsoT$^{ZnF}$ and the UIM and has a Cys residue conjugated with the fluorophore. Relative fluorescence intensity of Atto532-tISR L1 Cys2 was measured following the addition of different concentrations of free ubiquitin proteins or conjugated ubiquitin proteins. Atto532-tISRL1 Cys2 showed an 8-fold increase in fluorescence intensity when bound to free ubiquitin protein over a range of 0-1000 nM free ubiquitin (see FIG. 15). There was little change in fluorescence intensity across the same concentrations of conjugated ubiquitin. These experiments demonstrate that Atto532-tISRL1 Cys2 has a large fluorescence change and a broad dynamic range for free ubiquitin detection.

The changes in fluorescence intensity measured during a competition assay with fluorophore-tagged ubiquitin protein and tIVR were further examined. Fluorescence intensity of emissions across 500 nm to 550 nm wavelengths of 3 nM fluorescein-tagged ubiquitin with 3 nM tIVR was measured. Concentrations ranging from 0 to 3000 nM of untagged free ubiquitin were added to the mixture. Fluorescence intensity increased with higher concentrations of free ubiquitin. Further, there was no shift observed in the fluorescence emission wavelength due to additions of the free ubiquitin (see FIG. 16). These results demonstrate that fluorescence intensity is a reliable readout for assays involving chimeric polypeptide sensors.

Example 4

Use of Anisotropy as a Readout

Anisotropy is another aspect of fluorescence signaling that can be used with chimeric polypeptide sensors as a signal to detect free ubiquitin proteins or ubiquitin-like proteins. As is the case with fluorescence intensity, changes in anisotropy can be detected from the fluorophore when the chimeric polypeptide sensor and ubiquitin change between bound and unbound states.

Increased anisotropy can be detected from fluorophore-tagged ubiquitin protein when it binds to chimeric polypeptide sensor (see FIG. 17). Concentrations of tIVR (0-10 nM) were added to mixtures with 150 pM fluorescein-tagged ubiquitin proteins and fluorescence anisotropy was measured. Fluorescence was stimulated with polarized light at a 492 nm wavelength and polarized light emission was measured at 518 nm. Increasing the concentration of tIVR increased the anisotropy measured in the mixtures as the fluorescein-tagged ubiquitin proteins were bound by tIVR.

Anisotropy can be measured to determine free ubiquitin in competitive binding assays. Free ubiquitin protein was added to a mixture of 20 nM fluorescein-tagged ubiquitin proteins and 20 nM tIVR and anisotropy was measured. Adding the free ubiquitin proteins to the mixture displaced fluorophore-tagged ubiquitin proteins from the complex with tIVR and reduced the anisotropy measured from the mixture (see FIG. 18). The curve generated from this experiment can be used as a calibration standard in assays to measure free ubiquitin proteins in experimental samples.

Example 5

Use of Fluorescence Resonance Energy Transfer (Fret) as a Readout

The chimeric polypeptide sensors can be used with fluorescence resonance energy transfer (FRET) to detect free ubiquitin proteins. A competition assay was designed incorporating fluorescein-tagged ubiquitin protein with a modified tIVR tagged with a quencher. The amino acid sequence of the modified tIVR is as follows:

```
tIVR (R218C)
MGSSHHHHHHSSGLVPRGSHMKQEVQAWDGEVRQVSKHAFSLKQLDNPAR

IPPSGWKCSKCDMRENLWLNLTDGSILCGRRYFDGSGGNNHAVEHYRETG

YPLAVKLGTITPDGADVYSYDEDDMVLDPSLAEHLSHFGIDMLKMQKTGG

SGGSGSAAAEEAELDLKAAIQESLREAGGGSSGGGSDLLCKKGCGYYGNP

AWQGFCSKCWREEYHKACQK (Bold indicates the attachment site of the quencher; SEQ ID NO: 3)
```

The tIVR polypeptide can utilize fluorescence resonance energy transfer (FRET) to detect free ubiquitin proteins in a competition assay. Fluorescein-tagged ubiquitin proteins were combined in a mixture with the tIVR conjugated the quencher. When the fluorescein-tagged ubiquitin proteins are bound to the tIVR (left), the fluorescence intensity of the fluorophore-tagged ubiquitin proteins is reduced by the quencher conjugated to the tIVR. Additionally, the tIVR itself also contributes to the reduction of the fluorescence. Adding free ubiquitin proteins displaces bound fluorophore-tagged ubiquitin proteins, thus increasing the fluorescence intensity of the mixture (see FIG. 19). This experiment demonstrates that FRET is a feasible method to detect free ubiquitin proteins in conjunction with the chimeric polypeptide sensors. The curve generated from this experiment can be used as a calibration standard in assays to measure free ubiquitin proteins in complex biological samples.

Example 6

Deubiquitinase Assays with the Chimeric Polypeptides

The chimeric polypeptide sensors can be used to perform a deubiquitinase assay in real-time. This was validated by an experiment monitoring the deubiquitinase enzyme activity of YUH1 protein. The deubiquitinase enzyme activity was measured in a real-time assay (see FIG. 20). Release of ubiquitin by YUH1, a deubiquitinase enzyme, was measured as a fluorescence intensity change. Fluorescence intensity of a mixture containing YUH1, 500 nM of ubiquitin-D77, 10 nM fluorescein-tagged ubiquitin, and 10 nM tIVR was measured over time. Activity of YUH1 released ubiquitin proteins from conjugation to aspartic acid (i.e., the D77 residue), and thus increased the concentration of free ubiquitin protein. The free ubiquitin proteins displaced bound fluorescein-tagged ubiquitin, resulting in increased fluorescence intensity that was detected over time. This experiment demonstrates that real-time deubiquitinase assays can be performed with the chimeric polypeptide sensors.

This was further demonstrated in a second experiment (see FIG. 21). A real-time deubiquitinase assay using Atto532-tagged ubiquitin proteins and tIVR was performed. A mimic of polyubiquitinated-protein substrates was digested with 25 nM Usp2cc or 3 µM OTUB1, two deubiquitinase enzymes, with or without UbcH5c in the presence of 1 nM Atto532-tagged ubiquitin protein and 1 nM tIVR to detect free ubiquitin released by the deubiquitinases. OTUB1 activity is upregulated by UbcH5c, and this was detected by the experiment (see FIG. 21). The amino acid sequences for the polypeptides used in the experiment are as follows:
Ub5-Ovomucoid sequence is same as the one used in Yao et al. (2002) Nature vol. 419

OTUB1
(SEQ ID NO: 29)
MAAEEPQQQKQEPLGSDSEGVNCLAYDEAIMAQQDRIQQEIAVQNPLVSE

RLELSVLYKEYAEDDNIYQQKIKDLHKKYSYIRKTRPDGNCFYRAFGFSH

LEALLDDSKELQRFKAVSAKSKEDLVSQGFTEFTIEDFHNTFMDLIEQVE

KQTSVADLLASFNDQSTSDYLVVYLRLLTSGYLQRESKFFEHFIEGGRTV

KEFCQQEVEPMCKESDHIHIIALAQALSVSIQVEYMDRGEGGTTNPHIFP

EGSEPKVYLLYRPGHYDILYK

UBCH5C
(SEQ ID NO: 33)
MALKRINKELSDLARDPPAQCSAGPVGDDMFHWQATIMGPNDSPYQGGVF

FLTIHFPTDYPFKPPKVAFTTRIYHPNINSNGSICLDILRSQWSPALTIS

KVLLSICSLLCDPNPDDPLVPEIARIYKTDRDKYNRISREWTQKYAM

Usp2cc sequence is same as the one used in Catanzariti et al., Protein Sci. (2004) 13:1331

Example 7

Chimeric Polypeptides and Ubiquitin-Like Proteins

This example shows that chimeric polypeptides can preferentially bind free ubiquitin-like proteins. A chimeric protein (tIV) containing two ubiquitin binding domains, IsoT$^{ZnF}$ and Vps27$^{UIM}$, binds to Nedd8 with a $K_D$ of 9.4 µM. Increasing concentrations of free Nedd8 protein were added to Atto532-tIV, and the fluorescence intensity was measured (see FIG. 22). Based on the binding interactions of Vps27UIM and Nedd8, tIV is predicted to have a greater binding affinity for free Nedd8 protein than for conjugated Nedd8 protein. This experiment demonstrates that chimeric polypeptides can be constructed to detect free ubiquitin-like protein.

Example 8

Design and Construction of Chimeric Polypeptides

This example demonstrates the design and subsequent generation of chimeric polypeptides that bind to conjugated and free ubiquitin proteins. A single ubiquitin protein can simultaneously interact with multiple ubiquitin binding domains that bind to non-overlapping regions of ubiquitin (see FIG. 1). Chimeric polypeptides were designed that comprise a domain that binds the ubiquitin hydrophobic patch and a domain that binds to the surface of ubiquitin near Asp58 that are connected by a linker. These binding domains were linked to generate chimeric polypeptides that act as sensors for conjugated or free ubiquitin proteins (see FIG. 23). These result in a chimeric polypeptide that simultaneously binds ubiquitin proteins in two non-overlapping regions (see FIG. 24).

Using this strategy, a prototype chimeric polypeptide sensor was constructed (see FIG. 25). In the prototype (tSR), the domain that binds to the ubiquitin hydrophobic patch is the ubiquitin-interaction motif from the SSA protein (S5a$^{UIM}$) and the domain that binds to the surface of ubiquitin near Asp58 is the Rabex-5 ubiquitin binding zinc finger (Ruz).

The amino acid sequence is as follows:

tSR:
(SEQ ID NO: 7)
MPSSHHHHHHSSGLVPRGSHMTEEEQIAYAMQMSLREAGGGSDLLCKKGC
GYYGNPAWQGFCSKCWREEAHKCAAERAAAE

Structural models of the prototype chimeric polypeptide sensor binding to the ubiquitin protein have been provided. The tSR sensor is depicted with the S5a$^{UIM}$ and the Ruz domains bound to the ubiquitin hydrophobic patch and the ubiquitin surface near Asp58, respectively.

The binding affinities of tSR were determined (see FIG. 25). A competition assay was performed where free ubiquitin proteins, different kinds of conjugated free ubiquitin proteins, and Nedd8 were added to mixtures of 5 nM Atto532-tagged ubiquitin protein and 600 nM tSR. The relative fluorescence was measured. While tSR had similar binding affinities for unconjugated ubiquitin proteins and conjugated ubiquitin proteins, tSR had specificity against Nedd8. The Ki values for unconjugated ubiquitin proteins and the different kinds of conjugated free ubiquitin proteins are provided in a table (see FIG. 25). These results indicate that the tSR chimeric peptide universal sensor does not discriminate among free ubiquitin or polyubiquitins conjugated at different linkages.

The tSR can be used for direct titration experiments (see FIG. 26). The relative fluorescence intensity changes of Alexa488-tagged tSR when ubiquitin is added at varying concentrations. The relative fluorescence of 10 nM Alexa488 tSR was measured with different concentrations of unconjugated ubiquitin protein, conjugated ubiquitin protein, or Nedd8. Binding of unconjugated ubiquitin protein and conjugated ubiquitin protein, but not Nedd8 protein, to Alexa488-tagged tSR was detected. These results demonstrate that the tSR chimeric polypeptide shows selective binding to ubiquitin proteins over ubiquitin-like proteins.

All of the U.S. patents, U.S. patent application publications, U.S. patent applications, foreign patents, foreign patent applications and non-patent publications referred to in this specification and/or listed in any Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. A method of determining an amount of a free ubiquitin protein in a sample, said method comprising:
   (a) contacting said sample for a period of time with a chimeric polypeptide that preferentially binds to said free ubiquitin protein as compared to a conjugated ubiquitin protein, wherein said chimeric polypeptide comprises:
      (i) a first polypeptide that binds a ubiquitin protein monomer and a second polypeptide that binds said ubiquitin protein monomer, wherein said first and second polypeptides bind non-overlapping regions of said ubiquitin protein monomer; and
      (ii) a first linker, wherein said first linker connects said first and second polypeptides,
      wherein said first polypeptide binds to the ubiquitin hydrophobic patch of said ubiquitin protein monomer and comprises a ubiquitin binding domain selected from the group consisting of: Ubiquitin Associated domain (UBA), Ubiquitin Interacting Motif (UIM), double-sided ubiquitin-interacting motif (DUIM), Motif Interacting with Ubiquitin (MIU), coupling of ubiquitin conjugation to ER degradation (CUE), Golgi localized, Gamma-ear-containing, Arf-binding (GAT), Jun kinase activation domain binding/Mpr1p and Pad1p N-termini (Jab1/MPN), Np14 zinc finger (NZF), ubiquitin-binding zinc finger (UBZ), Ubiquitin binding surface (UBS), and Ubiquitin binding motif (UBM);
      wherein said second polypeptide binds to the surface of said ubiquitin protein monomer near Asp58 and comprises the Ruz domain of Rabex-5; and
   (b) determining:
      (i) an amount of said free ubiquitin protein bound to said chimeric polypeptide; or
      (ii) an amount of a free competitor ubiquitin protein bound to said chimeric polypeptide, wherein if step (b) (ii) is performed, said method further comprises step (c);
   (c) contacting said sample with said free competitor ubiquitin protein prior to step (b); wherein (i) said chimeric polypeptide, (ii) said free competitor ubiquitin protein, or (iii) each of said chimeric polypeptide and said free competitor ubiquitin protein further comprises a detectable label;
   thereby determining the amount of said free ubiquitin protein in said sample.

2. The method of claim 1, wherein said chimeric polypeptide comprises an amino acid sequence selected from the group consisting of the amino acid sequence set forth in SEQ ID NO: 1, SEQ ID NO: 2, SEQ ID NO: 3, SEQ ID NO: 4, SEQ ID NO: 5, SEQ ID NO: 6, and SEQ ID NO: 7, wherein said chimeric polypeptide binds a ubiquitin protein monomer in non-overlapping regions of said ubiquitin protein monomer.

3. The method of claim 1, wherein said chimeric polypeptide comprises an amino acid sequence selected from the group consisting of the amino acid sequence set forth in SEQ ID NO: 9, SEQ ID NO: 11, SEQ ID NO: 12, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, and SEQ ID NO: 42, and said second polypeptide comprises the amino acid sequence of SEQ ID NO: 10.

4. The method of claim 3, wherein said chimeric polypeptide further comprises:
   (c) a third polypeptide that binds to said ubiquitin protein monomer, wherein said first, second, and third polypeptides bind to non-overlapping regions of said ubiquitin protein monomer; and
   (d) a second linker, wherein said second linker connects said third and said first polypeptides,
   wherein said third polypeptide comprises the zinc finger binding domain of Isopeptidase T.

5. The method of claim 4, wherein said third polypeptide comprises an amino acid sequence selected from the group consisting of: the amino acid sequence of SEQ ID NO: 31, amino acid residues 1-147 of the amino acid sequence of SEQ ID NO: 1, and amino acid residues 1-148 of the amino acid sequence of SEQ ID NO: 2.

6. The method of claim 1, wherein said detectable label is a fluorophore and the detecting comprises measuring fluorescence intensity or fluorescence anisotropy.

7. The method of claim 1, further comprising:
(d) comparing the amount of the bound free ubiquitin protein to a predetermined value or to a control value.

8. The method of claim 1, wherein step (b) comprises determining the amount of the free ubiquitin competitor protein bound to said chimeric polypeptide at two or more time points during said period of time.

9. The method of claim 8, further comprising:
(d) comparing the amount of said bound free ubiquitin protein to a predetermined value or to a control value at two or more time points during the period of time.

10. The method of claim 1, comprising:
(a) contacting said sample for said period of time with said chimeric polypeptide that preferentially binds to said free ubiquitin protein protein as compared said conjugated ubiquitin protein;
(b) contacting said sample with said free competitor ubiquitin protein; and
(c) determining the amount of said free competitor ubiquitin protein bound to said chimeric polypeptide.

11. The method of claim 10, further comprising:
(d) comparing the amount of the free competitor ubiquitin protein bound to said chimeric polypeptide to a predetermined value or to a control value.

12. The method of claim 10, wherein step (c) comprises determining the amount of said ubiquitin competitor protein bound to said chimeric polypeptide at two or more time points during said period of time.

13. The method of claim 12, further comprising:
(d) comparing the amount of said ubiquitin competitor protein to said chimeric polypeptide to a predetermined value or a control value at two or more time points during said period of time.

14. The method of claim 1, wherein said sample is a biological sample derived from
(a) biological tissue that optionally comprises eukaryotic cells or
(b) cultured cells that optionally comprises eukaryotic cells.

15. The method of claim 1, wherein (i) said chimeric polypeptide comprises said detectable label; or (ii) said free competitor ubiquitin protein comprises said detectable label.

16. The method of claim 10, wherein said free ubiquitin competitor protein is tagged with a first detectable label, and said chimeric polypeptide is tagged with a second detectable label.

17. The method of claim 16, wherein said first detectable label and said second detectable label are suitable for performing fluorescence resonance energy transfer (FRET), and wherein
(a) said first detectable label is a quencher and said second detectable label is a fluorophore; or
(b) said first detectable label is a fluorophore and said second detectable label is a quencher.

18. A method of determining a total amount of a free ubiquitin protein or a conjugated ubiquitin protein in a sample, said method comprising:
(a) contacting said sample for a period of time with a chimeric polypeptide that preferentially binds to both said free and conjugated ubiquitin protein, wherein said chimeric polypeptide comprises:
(i) a first polypeptide that binds a ubiquitin protein monomer and a second polypeptide that binds said ubiquitin protein monomer, wherein said first and second polypeptides bind non-overlapping regions of said ubiquitin protein monomer; and
(ii) a first linker, wherein said first linker connects said first and second polypeptides,
wherein said first polypeptide binds to the ubiquitin hydrophobic patch of said ubiquitin protein monomer and comprises a ubiquitin binding domain selected from the group consisting of: Ubiquitin Associated domain (UBA), Ubiquitin Interacting Motif (UIM), double-sided ubiquitin-interacting motif (DUIM), Motif Interacting with Ubiquitin (MIU), coupling of ubiquitin conjugation to ER degradation (CUE), Golgi localized, Gamma-ear-containing, Arf-binding (GAT), Jun kinase activation domain binding/Mpr1p and Pad1p N-termini (Jab1/MPN), Np14 zinc finger (NZF), ubiquitin-binding zinc finger (UBZ), Ubiquitin binding surface (UBS), and Ubiquitin binding motif (UBM);
wherein said second polypeptide binds to the surface of said ubiquitin protein monomer near Asp58 and comprises the Ruz domain of Rabex-5; and
(b) determining:
(i) an amount of said ubiquitin protein bound to said chimeric polypeptide; or
(ii) an amount of a competitor ubiquitin protein bound to said chimeric polypeptide, wherein if step (b) (ii) is performed, said method further comprises step (c);
(c) contacting said chimeric polypeptide or said sample with said competitor ubiquitin protein prior to step (b);
thereby determining the total amount of said conjugated ubiquitin protein in said sample.

19. A method of determining an amount of an intact extracellular ubiquitin protein in a sample containing serum, said method comprising:
(a) contacting said sample for a period of time with a chimeric polypeptide that preferentially binds to said intact extracellular ubiquitin protein, wherein said chimeric polypeptide comprises:
(i) a first polypeptide that binds a ubiquitin protein monomer and a second polypeptide that binds said ubiquitin protein monomer, wherein said polypeptides bind non-overlapping regions of said ubiquitin protein monomer; and
(ii) a first linker, wherein said first linker connects said first and second polypeptides,
wherein said first polypeptide binds to the ubiquitin C-terminus and comprises the zinc finger binding domain of Isopeptidase T and wherein said second polypeptide binds to the ubiquitin hydrophobic patch of said ubiquitin protein monomer and comprises a ubiquitin binding domain selected from the group consisting of: Ubiquitin Associated domain (UBA), Ubiquitin Interacting Motif (UIM), double-sided ubiquitin-interacting motif (DUIM), Motif Interacting with Ubiquitin (MIU), coupling of ubiquitin conjugation to ER degradation (CUE), Golgi localized, Gamma-ear-containing, Arf-binding (GAT), Jun kinase activation domain binding/Mpr1p and Pad1p N-termini (Jab1/MPN), Np14 zinc finger (NZF), ubiquitin-binding zinc finger (UBZ), Ubiquitin binding surface (UBS), and Ubiquitin binding motif (UBM) or wherein said second polypeptide binds to the surface of said ubiquitin protein monomer near Asp58 and comprises the Ruz domain of Rabex-5; and
(b) determining:
(i) an amount of said intact extracellular ubiquitin bound to said chimeric polypeptide; or (ii) an amount of a competitor ubiquitin protein bound to said chimeric polypeptide, wherein if step (b) (ii) is performed, said method further comprises step (c);
(c) contacting said sample with said competitor ubiquitin protein prior to step (b);
thereby determining the total amount of said intact extracellular ubiquitin protein in said sample.

* * * * *